(12) United States Patent
Takashima et al.

(10) Patent No.: US 11,399,161 B2
(45) Date of Patent: Jul. 26, 2022

(54) SIGNAL PROCESSING DEVICE, SIGNAL PROCESSING METHOD, IMAGE CAPTURE DEVICE, AND MEDICAL IMAGE CAPTURE DEVICE

(71) Applicant: Sony Group Corporation, Tokyo (JP)

(72) Inventors: Masatoshi Takashima, Tokyo (JP); Tetsu Ogawa, Tokyo (JP); Takayoshi Oomori, Kanagawa (JP); Hiroshi Mori, Tokyo (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 16/981,572

(22) PCT Filed: Jan. 16, 2019

(86) PCT No.: PCT/JP2019/000997
§ 371 (c)(1),
(2) Date: Sep. 16, 2020

(87) PCT Pub. No.: WO2019/181154
PCT Pub. Date: Sep. 26, 2019

(65) Prior Publication Data
US 2021/0058591 A1    Feb. 25, 2021

(30) Foreign Application Priority Data
Mar. 23, 2018    (JP) .............................. JP2018-055815

(51) Int. Cl.
*A61B 1/00*    (2006.01)
*A61B 1/04*    (2006.01)
*A61B 1/045*    (2006.01)
*A61B 90/20*    (2016.01)
(Continued)

(52) U.S. Cl.
CPC ....... *H04N 9/04563* (2018.08); *A61B 90/361* (2016.02); *H04N 5/2353* (2013.01);
(Continued)

(58) Field of Classification Search
None
See application file for complete search history.

(56) References Cited

U.S. PATENT DOCUMENTS

| 2007/0153099 A1 | 7/2007 | Ohki et al. |
| 2016/0006914 A1* | 1/2016 | Neumann ............. G01S 7/4817 348/78 |

(Continued)

FOREIGN PATENT DOCUMENTS

| CN | 101742103 A | 6/2010 |
| CN | 106455942 A | 2/2017 |

(Continued)

OTHER PUBLICATIONS

Extended European Search Report dated Apr. 6, 2021 for corresponding European Application 19770867.0.

(Continued)

*Primary Examiner* — Patricia I Young
(74) *Attorney, Agent, or Firm* — Michael Best & Friedrich LLP

(57) ABSTRACT

A signal processing device has tunable wavelength extraction and detection of a narrow band, while maintaining resolution. The signal processing device includes an acquisition unit that acquires a signal of a first wavelength band in which wavelength extraction is possible in a tunable manner by means of postprocessing and a signal of a second wavelength band to be used for a special purpose; and a signal processing unit that performs signal processing using the signal of the first wavelength band and the signal of the second wavelength band.

2 Claims, 48 Drawing Sheets

(51) Int. Cl.
- *G01J 3/00* (2006.01)
- *G02B 21/00* (2006.01)
- *G02B 23/24* (2006.01)
- *H04N 5/225* (2006.01)
- *H04N 5/232* (2006.01)
- *H04N 5/235* (2006.01)
- *H04N 5/33* (2006.01)
- *H04N 9/07* (2006.01)
- *H04N 9/04* (2006.01)
- *A61B 90/00* (2016.01)

(52) U.S. Cl.
CPC ............. *A61B 1/04* (2013.01); *A61B 90/20* (2016.02); *A61B 2090/373* (2016.02); *H04N 9/04515* (2018.08); *H04N 2209/047* (2013.01)

(56) References Cited

U.S. PATENT DOCUMENTS

| | | | |
|---|---|---|---|
| 2018/0067296 A1* | 3/2018 | Sugie | H04N 5/23293 |
| 2018/0136116 A1* | 5/2018 | Takashima | G01N 33/0098 |
| 2019/0189696 A1 | 6/2019 | Yamaguchi et al. | |
| 2019/0369609 A1* | 12/2019 | Takashima | G05B 23/0216 |

FOREIGN PATENT DOCUMENTS

| | | |
|---|---|---|
| EP | 3504959 A1 | 7/2019 |
| JP | 2008-136251 A | 6/2008 |
| JP | 2011053361 A | 3/2011 |
| JP | 2017011459 A | 1/2017 |
| JP | 2017208496 A | 11/2017 |
| KR | 20120114895 A | 10/2012 |
| WO | 2015156153 A1 | 10/2015 |
| WO | 2016/208415 A1 | 12/2016 |
| WO | 2016208415 A1 | 12/2016 |

OTHER PUBLICATIONS

Chinese Office Action dated Dec. 1, 2021 for corresponding Chinese Application No. 201980026574.7.

* cited by examiner

EXPOSURE TIME

EXPOSURE TIME

▦ TUNABLE FILTER (A)

▢ PRI-DEDICATED FILTER (B1)

▢ PRI-DEDICATED FILTER (B2)

▨ SIF-DEDICATED FILTER (C1)

▧ SIF-DEDICATED FILTER (C2)

FIG. 21
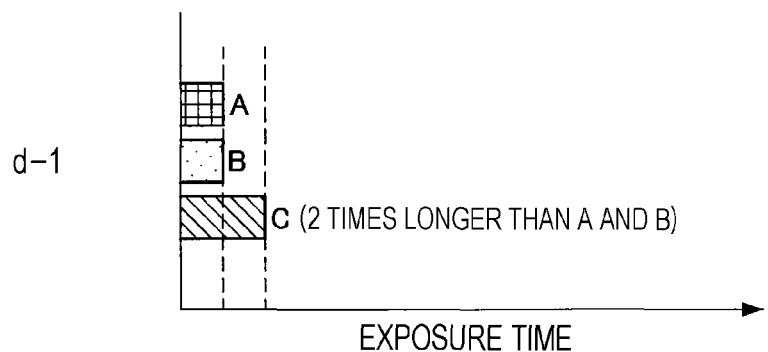
d-1
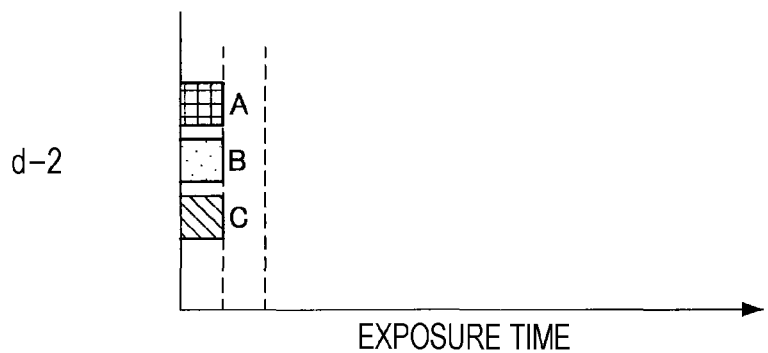
d-2
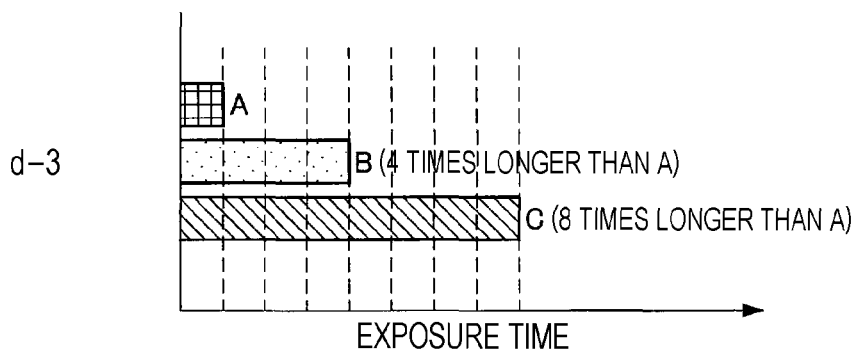
d-3

FIG. 26
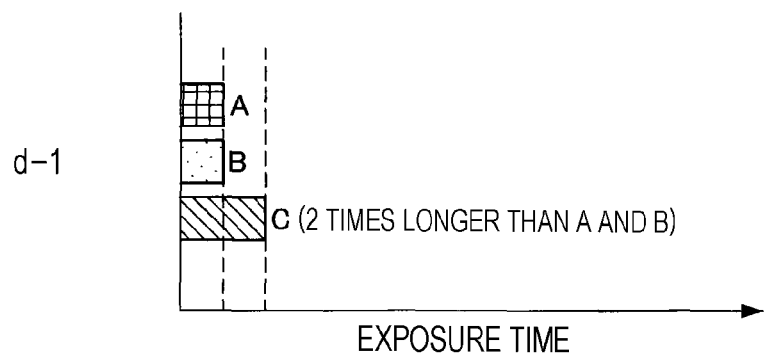
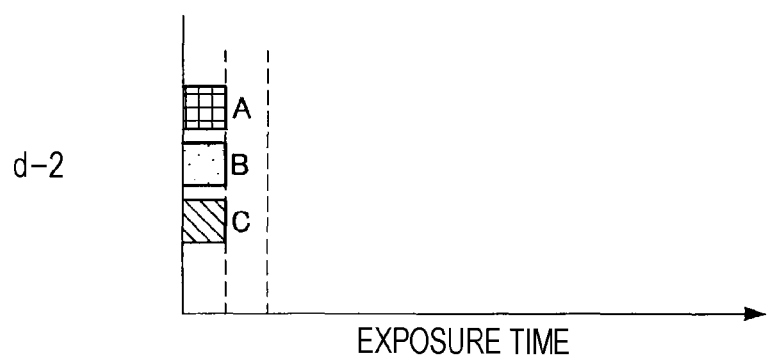
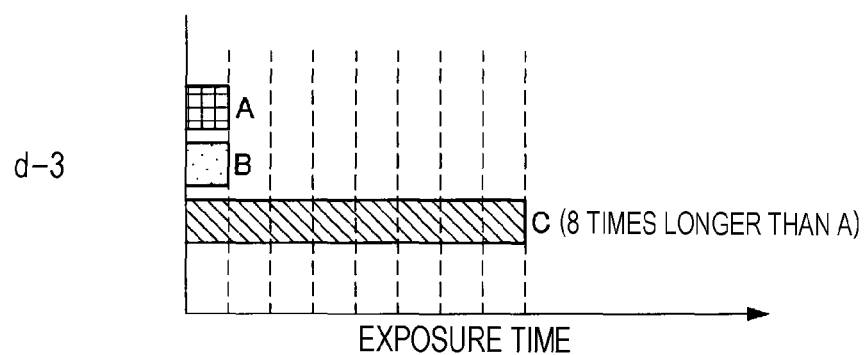

EXPOSURE TIME

SIGNAL PROCESSING DEVICE, SIGNAL PROCESSING METHOD, IMAGE CAPTURE DEVICE, AND MEDICAL IMAGE CAPTURE DEVICE

TECHNICAL FIELD

The present disclosure relates to a signal processing device, a signal processing method, an image capture device, and a medical image capture device.

BACKGROUND ART

In recent years, devices or systems capable of acquiring multi-band images in more than three RGB bands have been developed. For example, Patent Document 1 discloses a multispectral camera capable of acquiring a multi-band image with resolution and sensitivity comparable to those of a conventional RGB 3-band camera and improving color reproducibility.

CITATION LIST

Patent Document

Patent Document 1: Japanese Patent Application Laid-Open No. 2008-136251

SUMMARY OF THE INVENTION

Problems to be Solved by the Invention

However, according to the conventional multispectral camera as disclosed in Patent Document 1, it is difficult to enable extraction of an image of a desired wavelength band (hereinafter, the feature of enabling extraction of an image of a desired wavelength band is referred to as "being tunable") and to enable detection of a narrow band, while maintaining resolution.

The present disclosure has been made in view of the above problems, and an object of the present disclosure is to provide a novel and improved signal processing device, signal processing method, image capture device, and medical image capture device enabling wavelength extraction in a tunable manner and detection of a narrow band, while maintaining resolution.

Solutions to Problems

The present disclosure provides a signal processing device including: an acquisition unit that acquires a signal of a first wavelength band in which wavelength extraction is possible in a tunable manner by means of postprocessing and a signal of a second wavelength band to be used for a special purpose; and a signal processing unit that performs signal processing using the signal of the first wavelength band and the signal of the second wavelength band.

In addition, the present disclosure provides a signal processing method executed by a computer, the method including: acquiring a signal of a first wavelength band in which wavelength extraction is possible in a tunable manner by means of postprocessing and a signal of a second wavelength band to be used for a special purpose; and performing signal processing using the signal of the first wavelength band and the signal of the second wavelength band.

Further, the present disclosure provides an image capture device including: a first detection unit that detects a signal of a first wavelength band in which wavelength extraction is possible in a tunable manner by means of postprocessing; and a second detection unit that detects a signal of a second wavelength band to be used for a special purpose.

Further, the present disclosure provides a medical image capture device including: a first detection unit that detects a signal of a first wavelength band in which wavelength extraction is possible in a tunable manner by means of postprocessing; and a second detection unit that detects a signal of a second wavelength band to be used for a special purpose.

Effects of the Invention

As described above, the present disclosure enables wavelength extraction in a tunable manner and detection of a narrow band, while maintaining resolution.

It should be noted that the above effects are not necessarily restrictive, and any of the effects described in the present specification or other effects that can be grasped from the present specification may be provided together with or in place of the above effects.

BRIEF DESCRIPTION OF DRAWINGS

FIG. 21 is a diagram showing exposure times of filters in the fourth example.

FIG. 26 is a diagram showing exposure times of filters in a case where the fifth example is achieved by the image capture device 100 including three image capture mechanisms.

MODE FOR CARRYING OUT THE INVENTION

Figure 1:
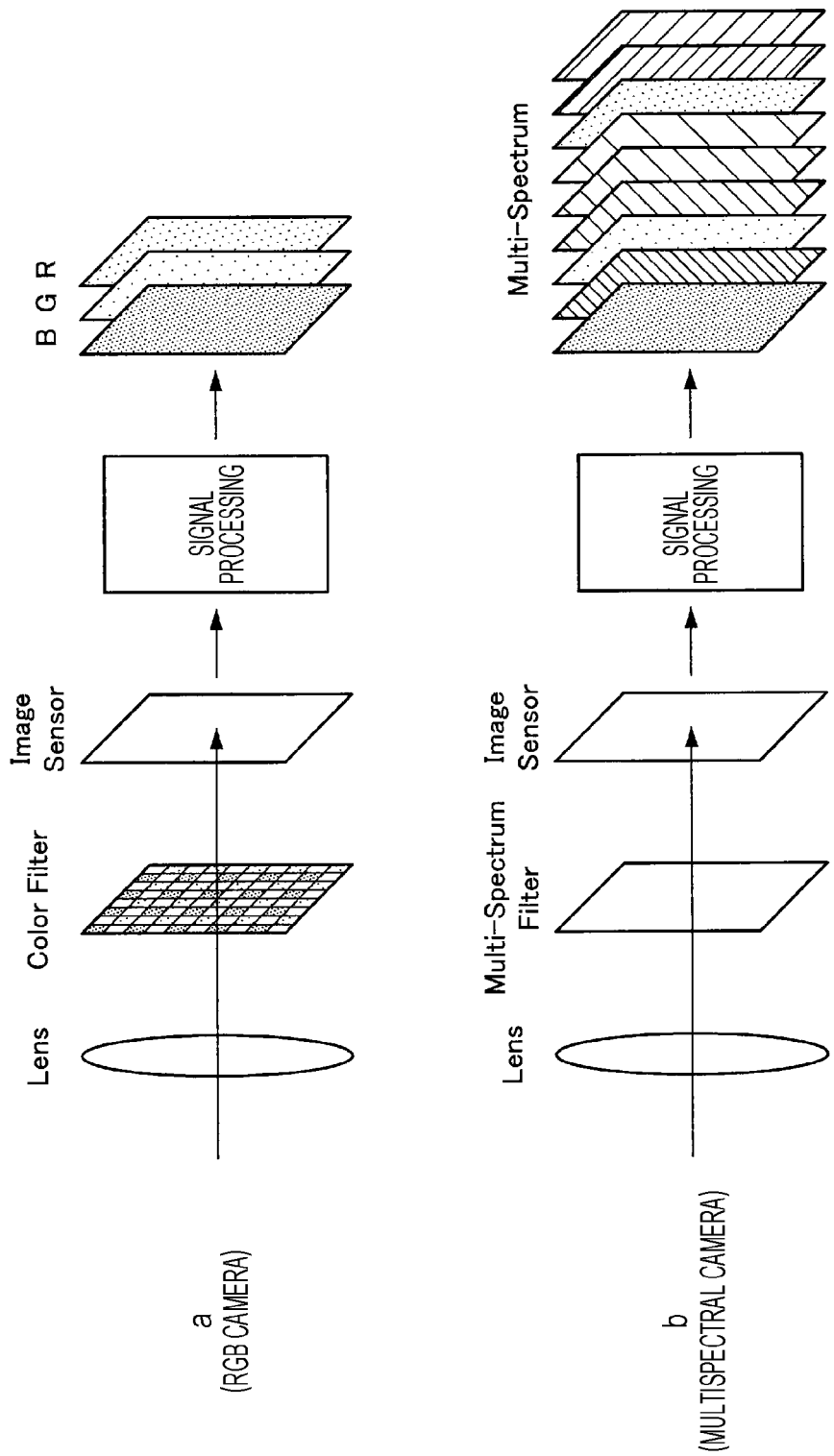
FIG. 1 is a diagram showing a difference between a conventional RGB camera and a multispectral camera.

Preferred embodiments of the present disclosure will now be described in detail with reference to the accompanying drawings. It should be noted that, in the present specification and the drawings, constituent elements having substantially the same functional configuration are designated by the same reference numerals, and a redundant description will be omitted.

Note that the description will be given in the following order.

1. Background
2. Embodiment
2.1 Overview
2.2. Configuration example
2.3. Signal processing flow
3. Example
3.1. First example
3.2. Second example
3.3. Third example
3.4. Fourth example
3.5. Fifth example
3.6. Sixth example
3.7. Seventh example
3.8. Eighth example
3.9. Ninth example
3.10. Tenth example
4. Application example
4.1. Example of application to medical image capture device
4.2. Example of application to operating room system 1. Background In recent years, devices or systems capable of acquiring multi-band images in more than three RGB bands have been developed. For example, Patent Document 1 discloses a multispectral camera capable of acquiring a multi-band image with resolution and sensitivity comparable to those of a conventional RGB 3-band camera and improving color reproducibility.

Here, the difference between the conventional RGB camera and the multispectral camera will be described with reference to FIG. 1. a of FIG. 1 schematically shows the configuration of the conventional RGB camera. In the RGB camera, light sequentially enters a lens, a color filter (for example, a Bayer color filter), and an image sensor in this order, and an RGB image is acquired by subsequent signal processing (or development processing).

b of FIG. 1 schematically shows the configuration of the multispectral camera. The multispectral camera is provided with a multi-spectrum filter instead of the color filter in the RGB camera, so that the incident light is separated into more wavelength bands than RGB, and a multispectral image is acquired by subsequent signal processing.

There are roughly two types of methods for acquiring multispectral images. More specifically, there is a method for acquiring a multispectral image by collecting pixel data generated by transmission of incident light through multi-spectrum filters in a case where each of the multi-spectrum filters has a spectral characteristic of transmitting light in a narrow band. More specifically, an image sensor has been already developed which includes multi-spectrum filters, each having narrow-band (with a half bandwidth of about 10 to 20 [nm]) spectral characteristics, due to formation of resonant paths having different heights for each pixel at the upper portion of the image sensor. For example, an image sensor with 2048×1088 pixels including 16 types of narrow-band multi-spectrum filters in 4×4 pixel array has been developed, and a multispectral image is acquired by performing demosaicing (collecting pixels, spatial filtering, etc.) on raw data acquired from the image sensor.

As another method, in a case where the multi-spectrum filter has a spectral characteristic of transmitting light in a wide band, an inverse matrix calculation is performed on a pixel after light has passed through each multi-spectrum filter, by which an image of a desired wavelength band is acquired. For example, a technique has been developed in which 32×32 (1024) filters of different types are formed on an image sensor, and an inverse matrix calculation is performed on raw data acquired from the image sensor after the raw data is subjected to demosaicing, by which an image of an ultra narrow band (with a half bandwidth of several nanometers) is obtained. In this technique, multi-spectrum filters that utilize plasmon resonance induced by incident light can be used.

Here, as described above, according to conventional multispectral cameras including the one disclosed in Patent Document 1, it is difficult to enable wavelength extraction in a tunable manner and detection of a narrow band, while maintaining resolution.

More specifically described, in a case where a wavelength is extracted in a tunable manner, as the number of types of filters to be used increases, narrower band can be detected, but the spatial resolution decreases. On the other hand, as the number of filters to be used is decreased, the spatial resolution is increased as compared to the above case, but it becomes difficult to detect a narrower band over a broad wavelength band (in other words, the wavelength resolution decreases). Therefore, it is difficult to enable wavelength extraction in a tunable manner and detection of a narrow band while maintaining resolution.

Therefore, in view of the above circumstances, the discloser of the present invention has devised the technology of the present disclosure. An image capture device 100 according to the present disclosure includes: a first detection unit that detects a signal of a first wavelength band in which wavelength extraction is possible in a tunable manner by means of postprocessing; and a second detection unit that detects a signal of a second wavelength band to be used for a special purpose. Thus, the image capture device 100 can address the abovementioned problems. The present disclosure will be described below in detail.

2. Embodiment

2.1. Overview

First, an overview of an embodiment of the present disclosure will be described. An image capture device 100 according to the present embodiment is provided with, in a stage preceding an image sensor and for each pixel, a filter (hereinafter sometimes referred to as a "tunable filter" for convenience) that can transmit light of a first wavelength band in which wavelength extraction is possible in a tunable manner, and a filter (hereinafter sometimes referred to as a "special purpose filter" for convenience) that can transmit light of a second wavelength band to be used for a special purpose. It should be noted that "being used for a special purpose" refers to being used for acquiring (for example, generating) spectral information (for example, an image) corresponding to the wavelength of a (special purpose) filter. For example, "being used for a special purpose" refers to being used to obtain spectral information corresponding to a wavelength suitable for an observation target in special light observation, or a wavelength used for calculation of a vegetation index.

Here, a filter included in the image capture device 100 will be described with reference to FIG. 2. As shown in a of FIG. 2, a plurality of tunable filters and a plurality of special purpose filters (special purpose filters 1 and special purpose filters 2 in this figure) are periodically arranged on pixels 10 in M×N (4×4 in this figure) array in the image capture device 100. More specifically, the tunable filters are arranged on twelve pixels, while the special purpose filters 1 are arranged on two pixels, and the special purpose filters 2 are arranged on two pixels.

Figure 2:
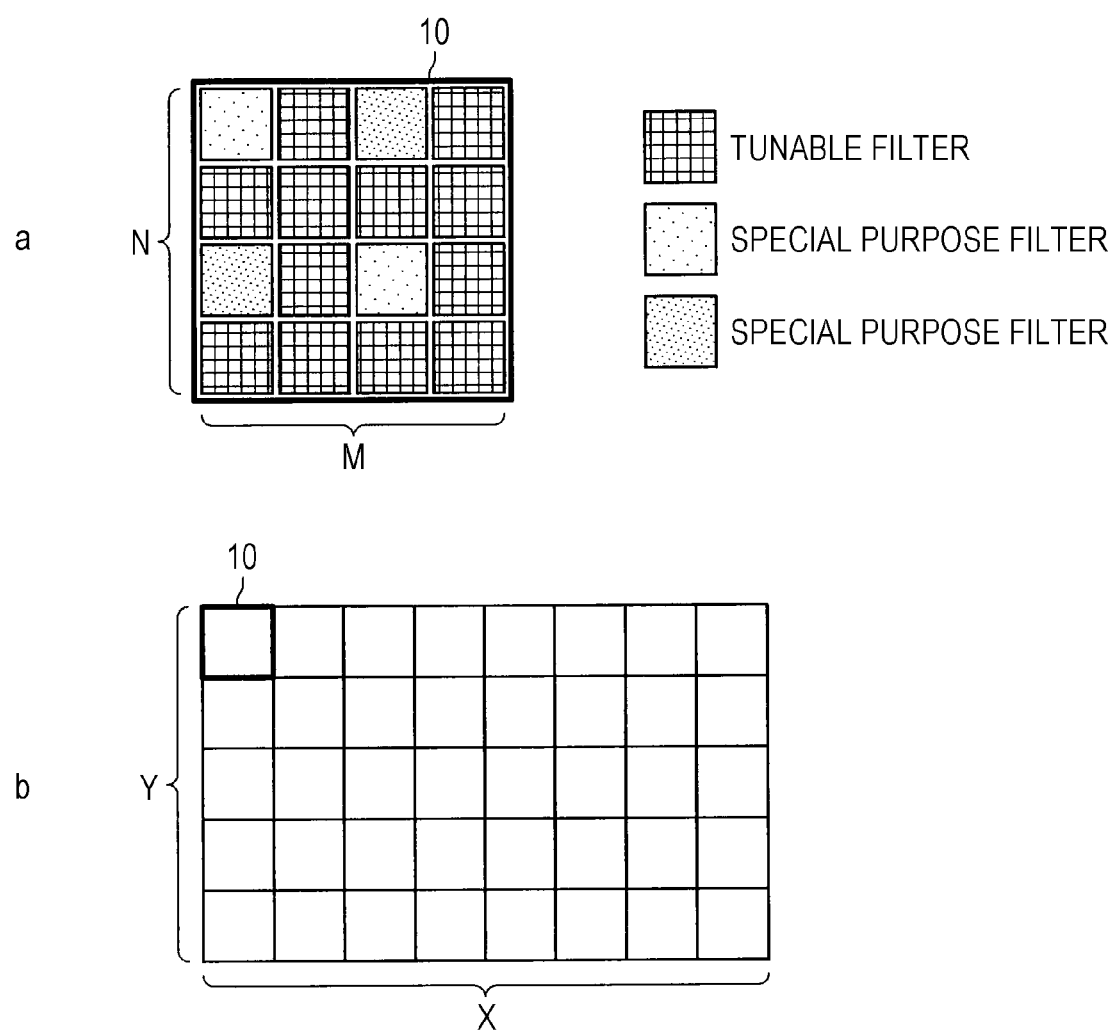
FIG. 2 is a diagram showing a filter included in an image capture device 100.

Then, as shown in b of FIG. 2, one filter is constructed by arranging the M×N pixels 10 in X×Y array. Therefore, the image capture device 100 can capture M×X (horizontal) and N×Y (vertical) pixels. Note that the filter included in the image capture device 100 is not limited to that in the example of FIG. 2. For example, in a of FIG. 2, the number of types of tunable filters or special purpose filters is not particularly limited. Further, the periodical arrangement of the tunable filters or the special purpose filters may be appropriately changed, or they may not be periodically arranged.

Here, the tunable filter has a spectral characteristic of transmitting light in a wide band, and in a case where it is combined with the image sensor in the following stage, the sensing sensitivity tends to be increased. On the other hand, the special purpose filter is required to have a spectral characteristic of transmitting light in a narrow band, or a spectral characteristic of transmitting light in a wide band, depending on a target to be detected. Further, in a case where a plurality of types of special purpose filters is used, their spectral characteristics may differ greatly from each other.

As described above, since the output sensitivity of each pixel differs depending on the transmittance of each filter, the sensitivity of the image sensor, or the like, the image capture device 100 according to the present embodiment more appropriately acquires signals of wavelength bands by modifying filters or exposure control.

Figure 3:
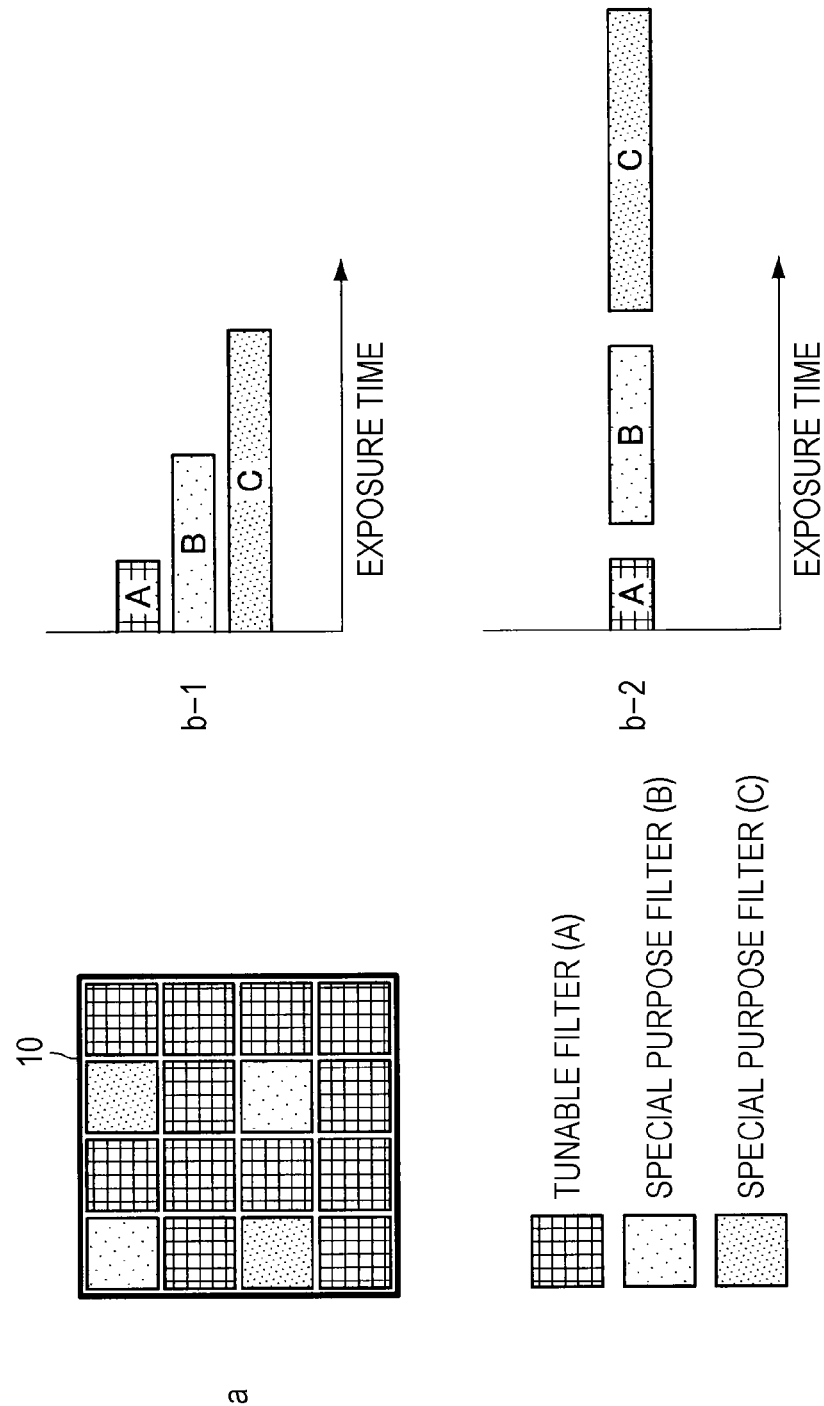
FIG. 3 is a diagram showing a relationship between a filter configuration and an exposure time.

For example, suppose the case where, in pixels in a 4×4 array as shown in a of FIG. 3, the output sensitivities of the pixels having tunable filters (A) is the highest, followed by the output sensitivities of the pixels having special purpose filters 1(B), then, the output sensitivities of the pixels having special purpose filters 2(C). In this case, as shown in b-1 of FIG. 3, the image capture device 100 adjusts the exposure times of the respective pixels such that the exposure times are sequentially decreased in the order of the pixels having the tunable filters (A), the pixels having the special purpose filters 1(B), and the pixels having the special purpose filters 2(C) according to the output sensitivities of the respective pixels. In this way, the image capture device 100 can acquire an appropriate image by controlling the exposure time of each pixel.

Note that, in a case where the exposure time suitable for each pixel is different as shown in b-2 of FIG. 3, the image capture device 100 may perform an image capturing process for each exposure time. More specifically, the image capture device 100 may perform a first image capturing process after performing an exposure suitable for the tunable filters (A), then, perform a second image capturing process after performing an exposure suitable for the special purpose filters 1(B), and lastly, perform a third image capturing process after performing an exposure suitable for the special purpose filters 2(C).

Figure 4:
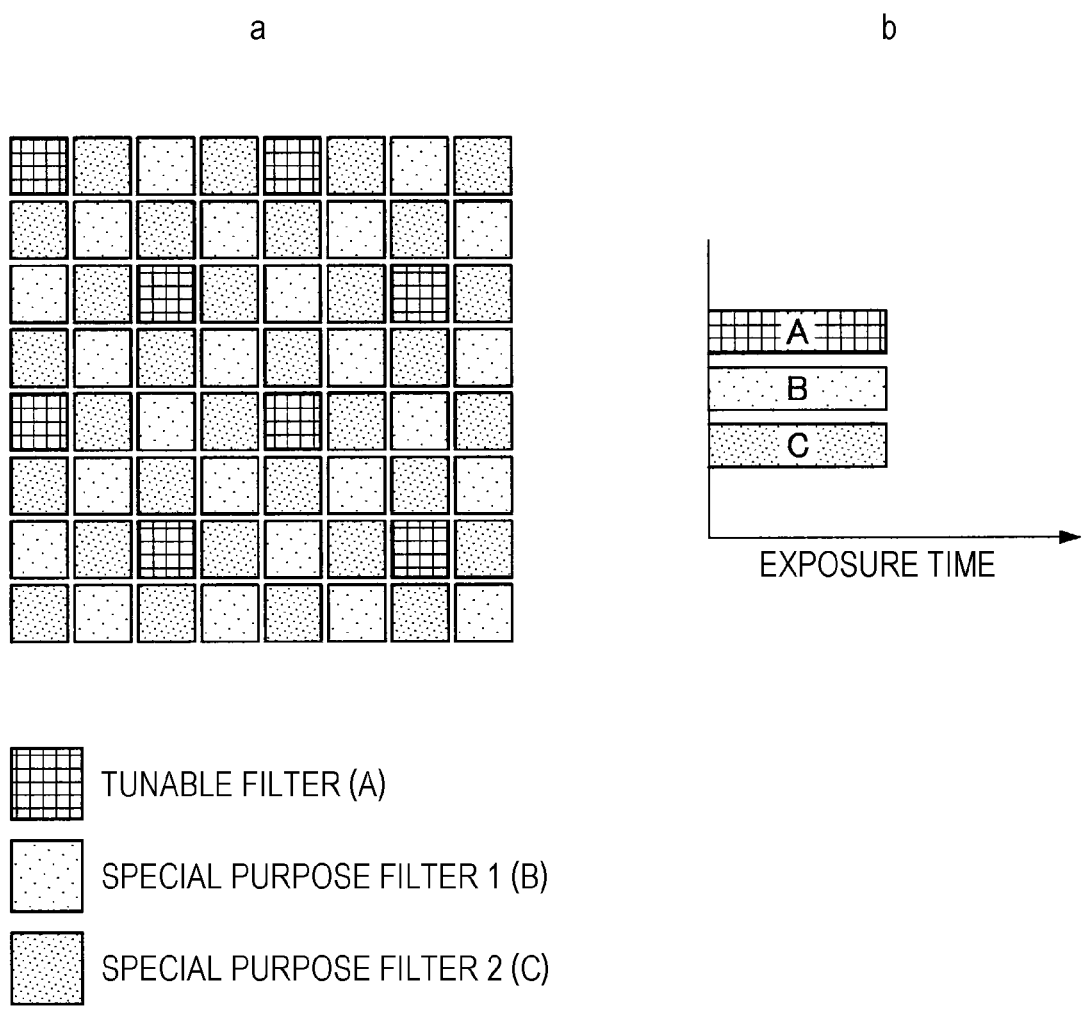
FIG. 4 is a diagram showing a relationship between a filter configuration and an exposure time.

Further, a of FIG. 4 shows an example in which the number of pixels of the special purpose filters 1(B) and the number of pixels of the special purpose filters 2(C) are increased. In this example, exposure times of pixels having the tunable filters (A), the pixels having the special purpose filters 1(B), and the pixels having the special purpose filters 2(C) are adjusted to be substantially equal to each other as shown in b of FIG. 4.

Figure 5:
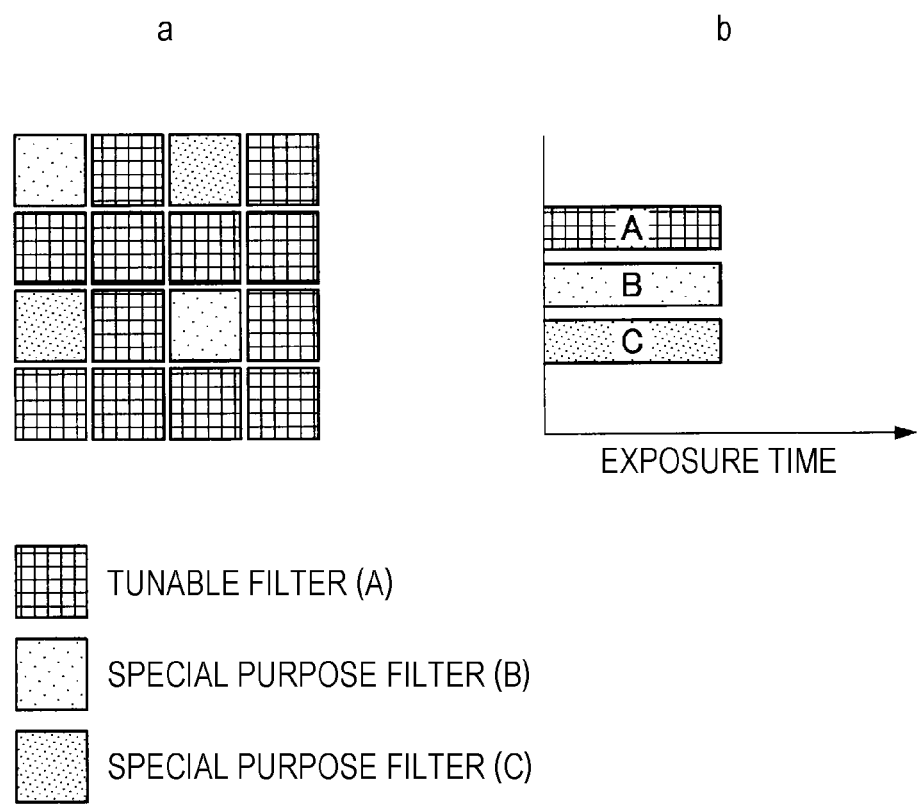
FIG. 5 is a diagram showing a relationship between a filter configuration and an exposure time.

Further, a of FIG. 5 shows an example in which the transmittance of each filter is adjusted such that pixels having the tunable filters (A), pixels having the special purpose filters 1(B), and pixels having the special purpose filters 2(C) have substantially the same output sensitivity. As a result, the image capture device 100 can set the exposure times of the pixels of the tunable filters (A), the pixels of the special purpose filters 1(B), and the pixels of the special purpose filters 2(C) to be substantially the same as shown in b of FIG. 5.

Note that, in the above examples, both the tunable filters and the special purpose filters are arranged on one image sensor. However, it is not limited thereto. For example, in a case where the image capture device 100 includes a plurality of image capture mechanisms like a compound eye camera, the tunable filters and the special purpose filters may be arranged on different image sensors 150. In this case, the image capture device 100 can acquire an appropriate image by controlling the exposure time for each image sensor. Further, the transmittances of filters arranged on the respective image sensors may be adjusted so that the exposure times of the image sensors are substantially the same as in the example shown in FIG. 5.

Here, it is assumed that the image capture device 100 according to the present embodiment is mounted on an unmanned aerial vehicle (UAV) including a drone and the like, and captures an image of the ground from the sky. Then, the image captured by the image capture device 100 is used to calculate a predetermined vegetation index indicating a vegetation state such as the distribution condition and activity of vegetation on the ground.

In this case, the type of vegetation index to be analyzed differs depending on the type of plant and the growth stage. For example, for a dark green plant, analysis of a vegetation index called normalized difference vegetation index (NDVI) is effective in order to accurately recognize a change in the growth stage. In order to calculate NDVI, it is necessary to acquire an image in a wavelength band of red light and an image in a near-infrared (NIR) wavelength band. Further, in order to accurately recognize a change after the plant has grown to some extent, it is effective to analyze a vegetation index called green normalized difference vegetation index (GNDVI). In order to calculate GNDVI, it is necessary to acquire an image in a wavelength band of green light and an image in the NIR wavelength band. Furthermore, for rice, wheat, etc., NDVI analysis is again effective in order to accurately recognize their changes during harvesting.

As described above, the type of vegetation index to be analyzed differs depending on the type of plant and the growth stage. Therefore, when data analysis is performed after image capture, the image capture device 100 that enables wavelength extraction in a tunable manner according to the present embodiment is effective. Since the half bandwidth of the signal used for the above vegetation index analysis is relatively great such as about 50 to 100 [nm], the image capture device 100 can perform processing using several to several tens of types of tunable filters, thereby being capable of extracting wavelengths in a tunable manner while maintaining resolution.

Further, the half bandwidth of a signal used for the analysis of a vegetation index such as photochemical reflectance index (PRI) (index indicating heat dissipation of photosynthesis) and solar-induced fluorescence (SIF) (index indicating chlorophyll fluorescence) for detecting the photosynthesis state of plants (for example, photosynthetic speed of plants, etc.) is relatively narrow such as about 1 to 20 [nm]. As described above, the image capture device 100 includes not only the tunable filters but also the special purpose filters, thereby being capable of also measuring the PRI or SIF using the special purpose filters. That is, the image capture device 100 can simultaneously achieve the measurement of NDVI or GNDVI described above and the measurement of PRI or SIF.

Note that the embodiment of the present disclosure is not limited to the above. For example, the image capture device 100 may not be mounted on an UAV. Further, the target to which the image capturing process by the image capture device 100 is to be performed is not limited to vegetation. For example, the image capture device 100 may be mounted on an artificial satellite or a vehicle such as a tractor. Further, the target to which the image capturing process by the image capture device 100 may be, for example, a structure such as a building or a bridge which is an infrastructure to be inspected, or an object to be inspected in factory automation (FA).

2.2. Configuration Example

The overview of the embodiment of the present disclosure has been described above. Subsequently, a configuration example of the image capture device 100 according to the present embodiment will be described.

Figure 6:
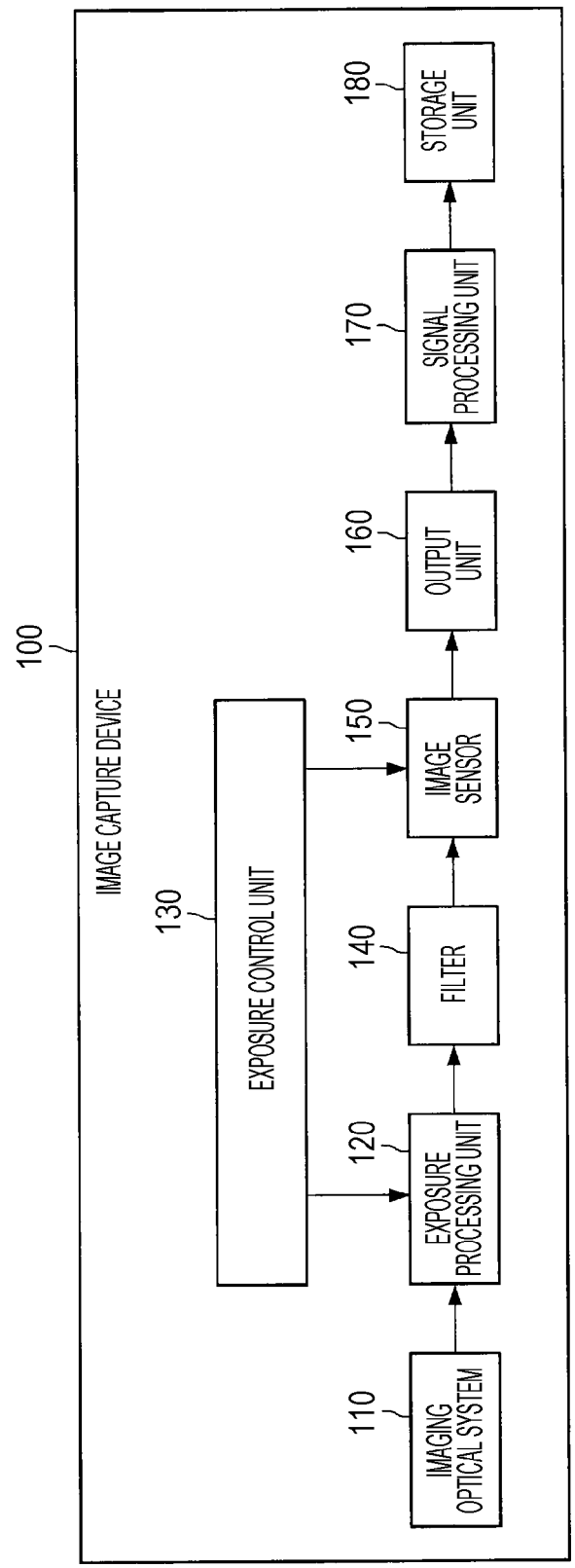
FIG. 6 is a block diagram showing a configuration example of the image capture device 100.

As shown in FIG. 6, the image capture device 100 includes an imaging optical system 110, an exposure processing unit 120, an exposure control unit 130, a filter 140, an image sensor 150, an output unit 160, a signal processing unit 170, and a storage unit 180.

The imaging optical system 110 includes optical elements such as a plurality of lenses used during image capture. Light from a subject passes through the imaging optical system 110, and enters the subsequent exposure processing unit 120. Note that the type, arrangement, or the like of the optical elements included in the imaging optical system 110 are not particularly limited.

The exposure processing unit 120 performs processing related to exposure. More specifically, the exposure processing unit 120 starts and stops exposure by controlling opening and closing of a shutter or an iris (IRIS) on the basis of a control signal from the exposure control unit 130. It should be noted that a mechanism for the exposure processing provided in the exposure processing unit 120 is not particularly limited.

The exposure control unit 130 controls the exposure processing by the exposure processing unit 120. More specifically, the exposure control unit 130 performs exposure control for each pixel according to spectral sensitivities of the filter 140 and the image sensor 150, the configuration of the filter 140 (the configuration of a tunable filter and a special purpose filter), the transmittance of the filter 140, the reflectance of the subject, and the like. The exposure control unit 130 controls the exposure processing by the exposure processing unit 120 by generating a control signal including information such as an exposure time or exposure timing and providing the control signal to the exposure processing unit 120. The exposure control unit 130 may also control the sensitivity of the image sensor 150. Note that, in a case where the transmittance and the like of the filter 140 are adjusted so that the exposure times of the respective pixels are substantially the same as described above, the exposure control unit 130 may not control the exposure time. Note that the exposure control method by the exposure control unit 130 is not limited to that described above.

The filter 140 is, as described above, a filter in which a plurality of tunable filters and a plurality of special purpose filters are periodically arranged in an array. Here, it is supposed that the filter 140 includes a special purpose filter that transmits light of a wavelength of approximately 531 [nm] and a special purpose filter that transmits light of a wavelength of approximately 570 [nm] for the calculation of PRI, and a special purpose filter that transmits light of a wavelength of approximately 761 [nm] and a special purpose filter that transmits light of a wavelength of approximately 758 [nm] for the calculation of SIF.

The image sensor 150 is, for example, an imaging element such as a charge-coupled device (CCD) sensor or a complementary metal oxide semiconductor (CMOS) sensor. The image sensor 150 outputs a signal having an intensity according to an amount of received light for each pixel constituting a light-receiving surface, thereby acquiring image data according to the incident light on the light-receiving surface. The image sensor 150 and the filter 140 in the preceding stage constitute a first detection unit that detects a signal of a first wavelength band in which wavelength extraction is possible in a tunable manner and a second detection unit that detects a signal of a second wavelength band to be used for a special purpose. Note that the type of the image sensor 150 is not particularly limited. Further, although the present embodiment mainly describes a case where the image sensor 150 acquires image data, the present disclosure is not necessarily limited thereto. For example, the image sensor 150 may acquire data that can be generally obtained by the image sensor 150, such as spectral information.

The output unit 160 has a functional configuration for outputting the image data (raw data) acquired by the image sensor 150 and providing the acquired image data to the signal processing unit 170.

The signal processing unit 170 acquires the image data (raw data) output by the output unit 160 (in other words, the signal processing unit 170 also functions as an acquisition unit), and performs various kinds of signal processing on the image data. For example, the signal processing unit 170 performs demosaicing, inverse matrix calculation process, etc. on the image data output from the output unit 160, and thus generates a multispectral image (or various kinds of data such as multispectral information). Here, the demosaicing may simply mean collecting image data of each pixel, or may mean interpolating a defective pixel using surrounding pixels. The signal processing unit 170 can render the multispectral image smoother by performing the latter type of demosaicing. Further, the signal processing unit 170 can reduce the load of signal processing by performing the former type of demosaicing (simply collecting image data of each pixel). Note that the demosaicing is not always necessary and may be appropriately omitted depending on the acquired image data.

The signal processing unit 170 also calculates a vegetation index such as NDVI, GNDVI, PRI, or SIF using the generated multispectral image. More specifically, the signal processing unit 170 calculates NDVI by the following (Equation 1) and calculates GNDVI by (Equation 2), using the image data of pixels having the tunable filters. Note that "RED" in (Equation 1) indicates image data in the wavelength band of red light, "GRN" in (Equation 2) indicates image data in the wavelength band of green light, and "NIR" in (Equation 1) and (Equation 2) indicates image data in the NIR wavelength band.

[Equation 1]

$$NDVI = \frac{RED - NIR}{RED + NIR} \quad \text{(Equation 1)}$$

[Equation 2]

$$GNDVI = \frac{GRN - NIR}{GRN + NIR} \quad \text{(Equation 2)}$$

Further, the signal processing unit 170 calculates PRI by (Equation 3) below and SIF by (Equation 4), using the image data of the pixels having the special purpose filters. Note that "$\lambda_{531}$" in (Equation 3) indicates an image of a wavelength of about 531 [nm], and "$\lambda_{570}$" indicates an image of a wavelength of about 570 [nm]. Further, "$\lambda_{761}$" in (Equation 4) indicates an image of a wavelength of about 761 [nm], "$\lambda_{758}$" indicates an image of a wavelength of about 758 [nm], and "k" is a predetermined coefficient due to dark line.

[Equation 3]

$$PRI = \frac{\lambda_{531} - \lambda_{570}}{\lambda_{531} + \lambda_{570}} \quad \text{(Equation 3)}$$

[Equation 4]

$$SIF = \frac{\lambda_{761} - k * \lambda_{758}}{1 - k} \quad \text{(Equation 4)}$$

Furthermore, the signal processing unit 170 can diagnose the state of vegetation on the basis of the various vegetation indexes calculated as described above. More specifically, the signal processing unit 170 can diagnose the chlorophyll state of vegetation on the basis of NDVI and GNDVI. Further, the signal processing unit 170 can diagnose the photosynthesis state on the basis of PRI and SIF. In a case where the chlorophyll state of vegetation is good and the photosynthesis state is bad, leaving the vegetation under such condition adversely affects plants. Therefore, the signal processing unit 170 can diagnose that prompt action is required. Further, if the chlorophyll state of the vegetation is bad and the photosynthesis condition is also bad, it is considered that the plant is already dead and it is too late. Therefore, the signal processing unit 170 can diagnose that no action is required. Further, if the chlorophyll state is worse than those of surrounding plants, but the photosynthesis condition is good, the signal processing unit 170 can diagnose that the condition of the plant has been recovered due to some actions being taken.

Note that the method for diagnosing the condition of vegetation by the signal processing unit 170 is not limited to those described above. Further, the signal processing unit 170 may also perform a predetermined process on the basis of the diagnosis result. For example, the signal processing unit 170 may notify a user of the diagnosis result by displaying the diagnosis result on a predetermined display or the like or by outputting the diagnosis result by voice. Further, the processing content by the signal processing unit 170 is not limited to those described above, and the processing content by the signal processing unit 170 may be appropriately changed according to the application of the image capture device 100, the target to be captured, and the like.

The storage unit 180 stores various kinds of information. For example, the storage unit 180 can store the multispectral image generated by the signal processing unit 170, various calculated vegetation indexes, the diagnosis result of the vegetation state, or the like. Note that the information stored in the storage unit 180 is not limited to those described above. For example, the storage unit 180 can also store programs, parameters, or the like used by each component of the image capture device 100.

The configuration example of the image capture device 100 has been described above. Note that the functional configuration described above with reference to FIG. 6 is merely an example, and the configuration of the image capture device 100 is not limited to this example. For example, although the processes from the image capturing process to the signal processing are completed in the image capture device 100 in the example shown in FIG. 6, a part of these processes may be achieved by an external device.

Figure 7:
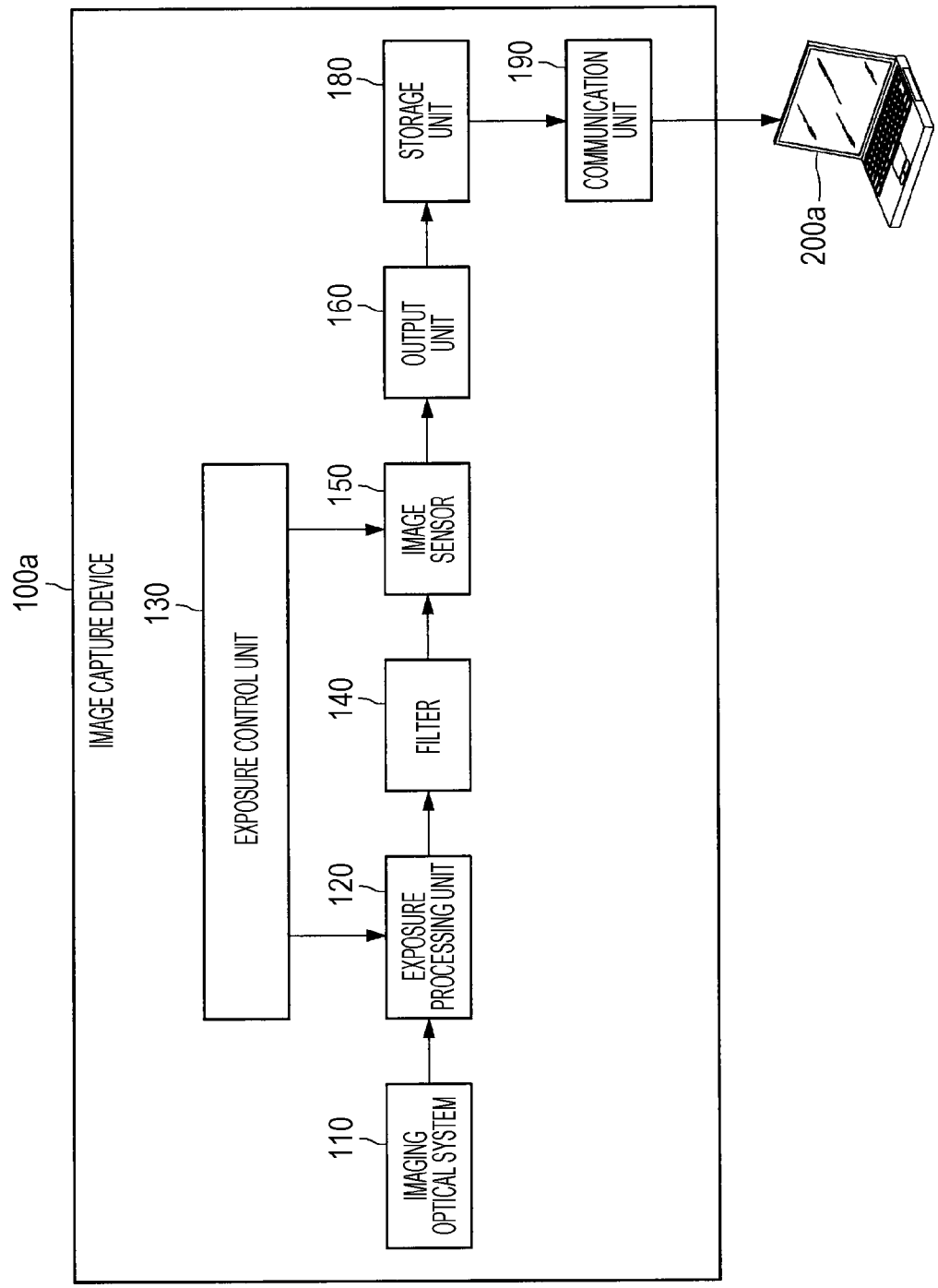
FIG. 7 is a block diagram showing a configuration example of the image capture device 100.

For example, some or all of the functions of the signal processing unit 170 may be achieved by an external device. More specifically, as shown in FIG. 7, the function of the signal processing unit 170 may be achieved by an information processing device 200a (for example, a personal computer (PC) or the like) capable of communicating with an image capture device 100a. In this case, the storage unit 180 stores image data (raw data) output by the output unit 160. Then, the image capture device 100a further includes a communication unit 190 that communicates with the information processing device 200a, and the communication unit 190 transmits the image data stored in the storage unit 180 to the information processing device 200a. Note that the communication method between the communication unit 190 and the information processing device 200a, the type of line, and the like are not particularly limited. Moreover, in order to ensure a communication band, the communication unit 190 may transmit the image data compressed by a predetermined lossless compression method to the information processing device 200a. In this case, the information processing device 200a restores the compressed image data and uses the restored image data in the process.

Then, the information processing device 200a performs various types of signal processing such as demosaicing and inverse matrix calculation on the image data received from the image capture device 100a, thereby generating a multispectral image, and diagnoses the vegetation state by calculating the vegetation index such as NDVI using the generated multispectral image. The processing capability of the image capture device 100a may be lower than that of the information processing device 200a due to a demand for reduction in size or the like. Therefore, due to the information processing device 200a achieving signal processing with a higher processing load, the speed or efficiency of the processing can be entirely improved. Note that the processing contents of the image capture device 100a and the information processing device 200a are not limited to those described above. For example, the image capture device 100a may be provided with a signal processing unit 170 (like the image capture device 100 in FIG. 6), the signal processing unit 170 may perform processes up to generation of a multispectral image, and the information processing device 200a may calculate the vegetation index and diagnose the vegetation state. Alternatively, the signal processing unit 170 of the image capture device 100a may perform processes up to the calculation of the vegetation index, and the information processing device 200a may diagnose the vegetation state.

Figure 8:
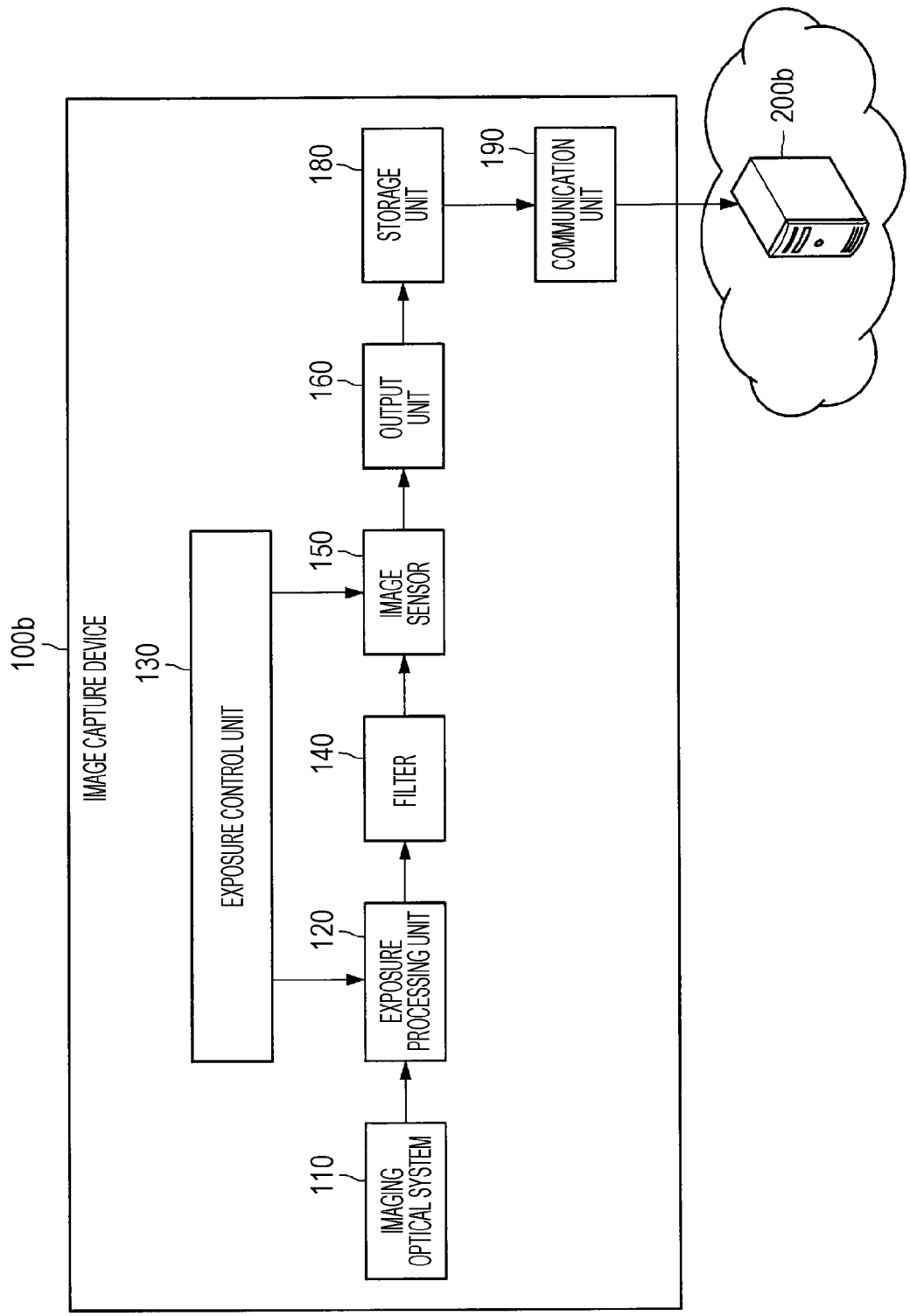
FIG. 8 is a block diagram showing a configuration example of the image capture device 100.

Further, as shown in FIG. 8, a communication unit 190 of an image capture device 100b may communicate with a cloud server 200b installed on a cloud network, instead of the information processing device 200a. With this configuration, the function of the signal processing unit 170 may be achieved by the cloud server 200b. This configuration can further improve the speed or efficiency of the overall process. Note that the cloud server 200b may acquire image data and the like via another information processing device that communicates with the image capture device 100b, without communicating with the image capture device 100b.

Figure 9:
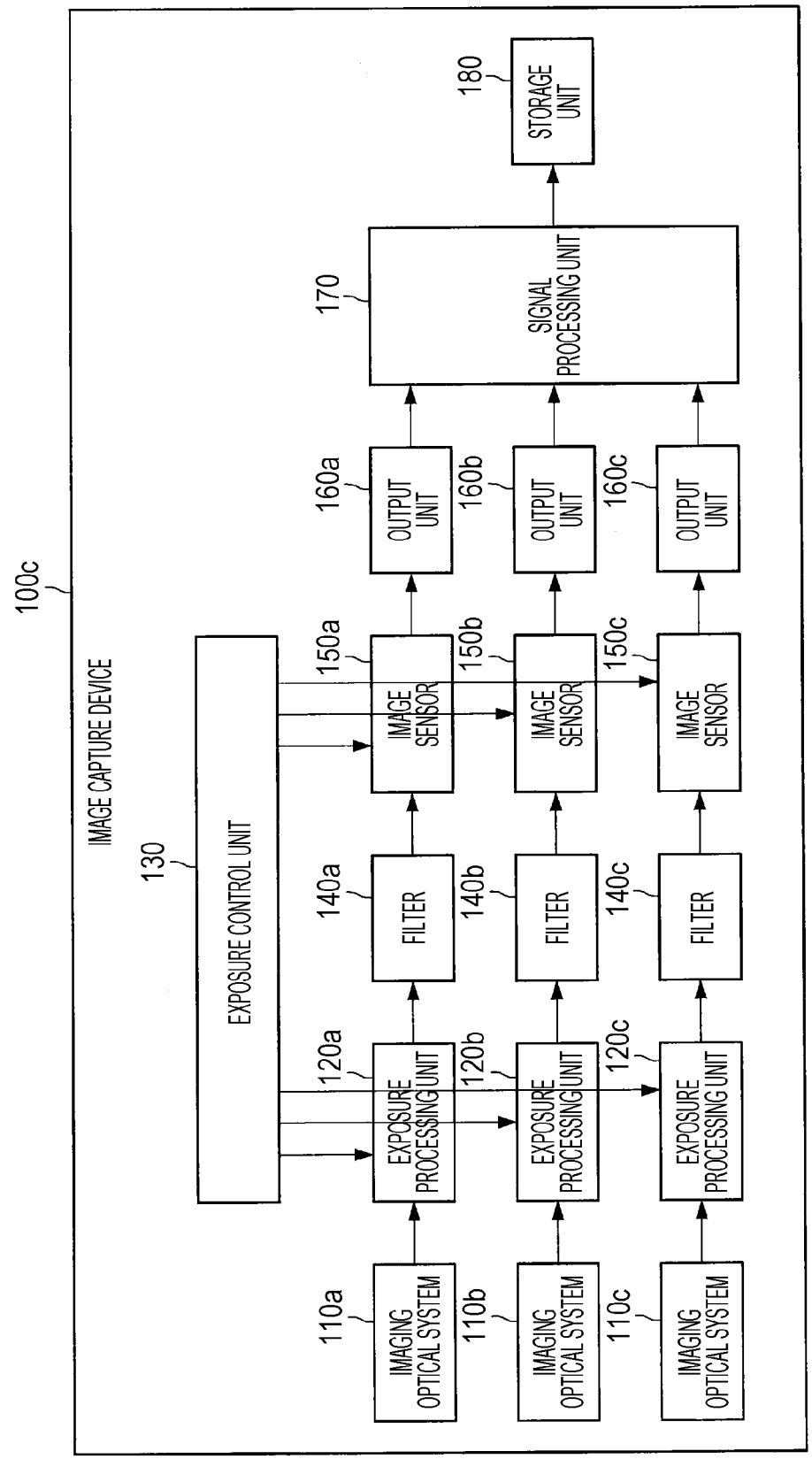
FIG. 9 is a block diagram showing a configuration example of an image capture device 100 including a plurality of image capture mechanisms.

Furthermore, the image capture device 100 can include a plurality of image capture mechanisms like a compound eye camera, as described above. If the image capture device 100 includes three image capture mechanisms, an image capture device 100c may include imaging optical systems 110a to 110c, exposure processing units 120a to 120c, filters 140a to 140c, image sensors 150a to 150c, output units 160a to 160c, a common signal processing unit 170, and a common storage unit 180, as shown in FIG. 9.

Note that, in this case, tunable filters and special purpose filters may be arranged on different image sensors 150. Since the outputs from the image sensors 150a to 150c are processed by the common signal processing unit 170 as shown in FIG. 9, the image capture device 100c can achieve an effect similar to the effect obtained in the case where tunable filters and special purpose filters are arranged on one image sensor 150. Note that the functional configuration described above with reference to FIG. 9 is merely an example, and the configuration of the image capture device 100c including a plurality of image capture mechanisms is not limited to this example.

2.3. Signal Processing Flow

The configuration example of the image capture device 100 according to the present embodiment has been described above. Next, an example of a flow of signal processing according to the present embodiment will be described with reference to FIG. 10. Although the information processing device 200a or the cloud server 200b which is an external device can achieve the function of the signal processing unit 170 of the image capture device 100 as described above, a case where the signal processing unit 170 of the image capture device 100 achieves all of the signal processing will be described below as one example. Further, it is supposed as a premise that pixels arranged in a 4×4 array are used for the processing, twelve pixels of the pixels in 4×4 array are equipped with tunable filters, two pixels of the remaining pixels are equipped with special purpose filters for PRI, and the remaining two pixels are equipped with special purpose filters for SIF. Further, the higher the resolution of the special purpose filter is (the narrower the half bandwidth is), the more preferable it is. However, a filter having a half bandwidth of several [nm] within a range including at least the target wavelength (for example, about 531 [nm] and about 570 [nm] for the special purpose filters for PRI, etc.) can be used.

In step S1000, the signal processing unit 170 of the image capture device 100 acquires raw data generated by the image sensor 150 via the output unit 160. It is assumed that the raw data includes data of pixels in which wavelength extraction is possible in a tunable manner and data of pixels for detecting a specific wavelength band used for a special purpose.

In step S1004, the signal processing unit 170 separates the acquired raw data for each filter, and thus, twelve tunable images, two images for PRI (an image of a wavelength of about 531 [nm] and an image of a wavelength of about 570 [nm]), and two images for SIF (an image of a wavelength of about 761 [nm] and an image of a wavelength of about 758 [nm]) are obtained. In step S1008, the user selects a vegetation index to be calculated. Note that the selector that selects the vegetation index may be other than the user (for example, a predetermined device, or the like).

When the user selects NDVI or GNDVI as the vegetation index to be calculated, the signal processing unit 170 performs demosaicing on twelve tunable images in step S1012. Note that the demosaicing is not always necessary and may be appropriately omitted depending on the acquired image data.

In step S1016, the signal processing unit 170 acquires an image of the NIR wavelength band (wavelength: about 800 [nm]). Then, when the user selects NDVI as the vegetation index to be calculated, the signal processing unit 170 acquires an image of the wavelength band of red light (RED) (wavelength: about 650 [nm]) in step S1020, and calculates NDVI through calculation of (Equation 1) described above using the image of the NIR wavelength band and the image of the wavelength band of red light in step S1024.

On the other hand, when the user selects GNDVI as the vegetation index to be calculated, the signal processing unit 170 acquires an image of the wavelength band of green light (wavelength: about 550 [nm]) in step S1028, and calculates GNDVI through calculation of (Equation 2) described above using the image of the NIR wavelength band and the image of the wavelength band of green light in step S1032.

When the user selects PRI as the vegetation index to be calculated in step S1008, the signal processing unit 170 performs demosaicing on the two images for PRI (the image of a wavelength of about 531 [nm] and the image of a wavelength of about 570 [nm]) in step S1036, and calculates PRI through calculation of (Equation 3) described above in step S1040. Further, when the user selects SIF as the vegetation index to be calculated in step S1008, the signal processing unit 170 performs demosaicing on the two images for SIF (the image of a wavelength of about 761 [nm] and the image of a wavelength of about 758 [nm]) in step S1044, and calculates SIF through calculation of (Equation 4) described above in step S1048. Note that, similarly to step S1012, the demosaicing is also not always necessary and may be appropriately omitted according to the acquired image data in steps S1036 and S1044.

In step S1052, the signal processing unit 170 diagnoses the vegetation state on the basis of the various vegetation indexes calculated in the previous stage. Thus, a series of processing is ended. A specific example of the method of diagnosing the vegetation state based on the vegetation index has been described above, and therefore, the description thereof will be omitted. Note that, as described above, the signal processing unit 170 may appropriately perform processing such as displaying the diagnosis result on a predetermined display.

Figure 10:
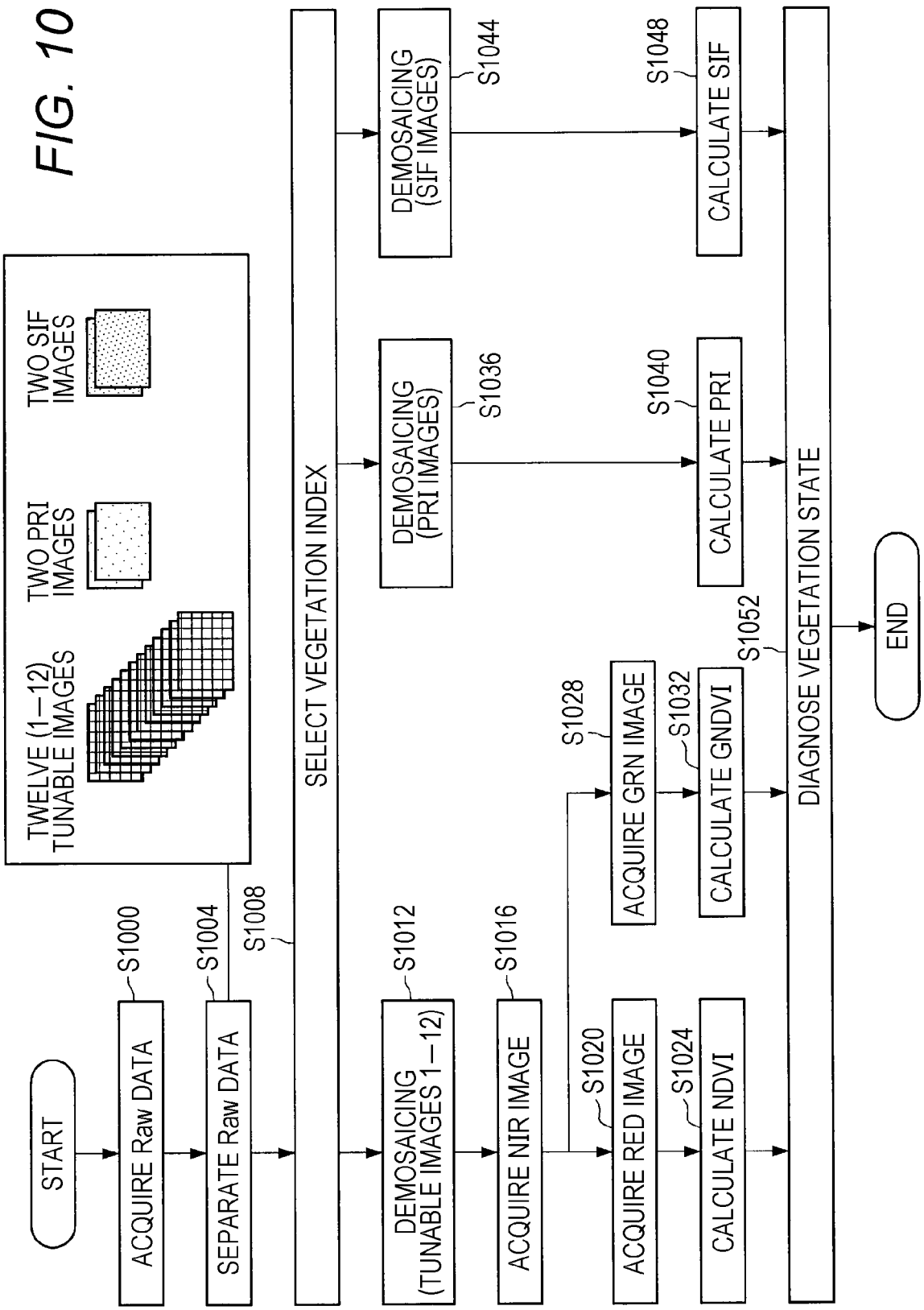
FIG. 10 is a flowchart showing an example of a flow of signal processing according to the present embodiment.

Note that the processes of steps in the flowchart shown in FIG. 10 are not necessarily performed in time series in the described order. That is, the processes of the respective steps in the flowchart may be performed in an order different from the described order, or may be performed in parallel.

3. Examples

An example of the flow of the signal processing according to the present embodiment has been described above. The embodiment of the present disclosure described above are applicable to various examples. Therefore, various examples to which the embodiment of the present disclosure is applied will be described below.

3.1. First Example

Figure 11:
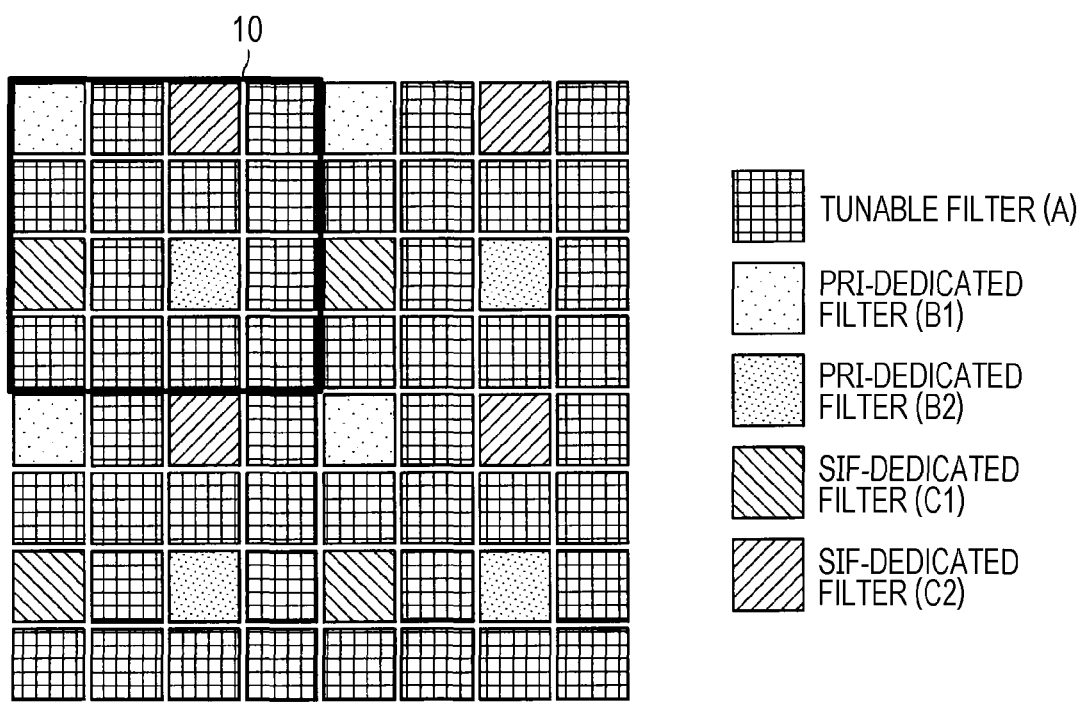
FIG. 11 is a diagram showing a configuration of a filter according to a first example.

First, a first example will be described. As shown in FIG. 11, in the present example, an optical low-pass filter is inserted in a stage preceding the filter 140 so that the pixels 10 arranged in a 4×4 array correspond to one pixel for sensing. In addition, in the pixels arrayed in a 4×4 array, two types of special purpose filters used for calculating PRI (a PRI-dedicated filter (B1) having a transmission spectral characteristic of transmitting light of a wavelength of about 531 [nm] and a PRI-dedicated filter (B2) having a transmission spectral characteristic of transmitting light of a wavelength of about 570 [nm]) are arranged on two pixels, respectively (two pixels in total), and two types of special purpose filters used for calculating SIF (a SIF-dedicated filter (C1) having a transmission spectral characteristic of transmitting light of a wavelength of about 761 [nm] and a SIF-dedicated filter (C2) having a transmission spectral characteristic of transmitting light of a wavelength of about 758 [nm]) are arranged on two pixels, respectively (two pixels in total). Then, the tunable filters (A) having a transmission spectral characteristic of transmitting light of a wide band (about 200 to 600 [nm]) are arranged on the remaining twelve pixels.

Figure 12:
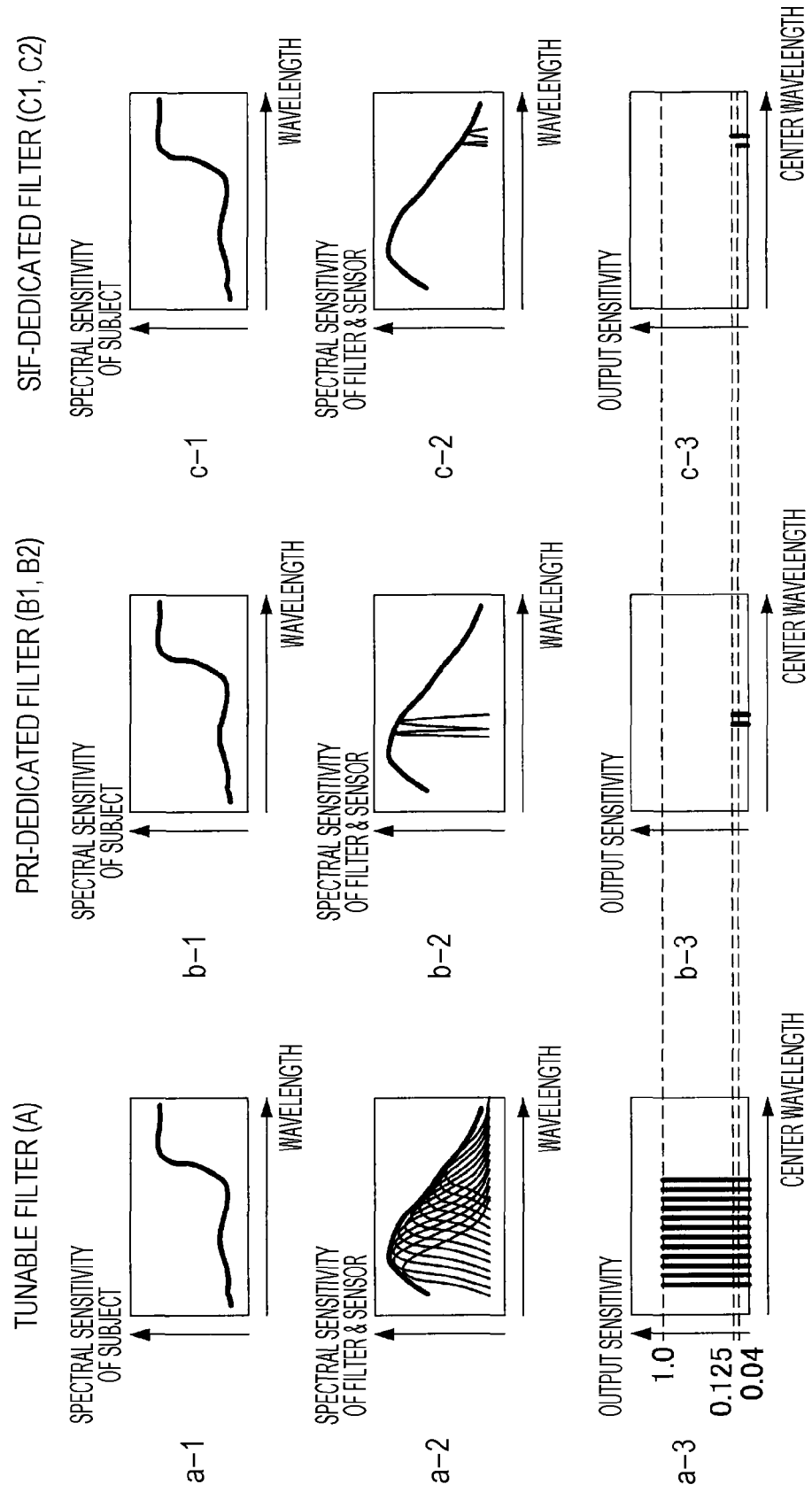
FIG. 12 is a diagram showing output sensitivities, etc. of pixels in the first example.

Then, consider a case where the reflected light from vegetation, which is the subject, has a spectral characteristic as shown in a-1 of FIG. 12, and the image sensor 150 receives the reflected light via the filter 140. The twelve pixels on which the tunable filters (A) are arranged have different spectral characteristics in a wide band (about 200 to 600 [nm]) as shown in a-2. It is assumed that, in a case where the twelve pixels having the tunable filters (A) arranged thereon receive the reflected light as shown in a-1, the output sensitivities of the respective pixels are the same at about 1.0 as shown in a-3.

On the other hand, it is assumed that the output sensitivities of the pixels on which two types of special purpose filters used for PRI calculation are arranged are about 0.125 (in other words, about ⅛ of the output sensitivities of the pixels having the tunable filters (A)) as shown in b-3. In addition, it is assumed that the output sensitivity of the pixel having the SIF-dedicated filter (C1) having transmission spectral characteristics of about 761 [nm] arranged thereon out of two types of the special purpose filters used for SIF calculation is still smaller, that is, about 0.04 (in other words, about 1/24 of the output sensitivities of the pixels having the tunable filters (A)) as shown in c-3, because the wavelength of about 761 [nm] corresponds to the dark lines in the solar spectrum. In addition, it is assumed that the output sensitivity of the pixel having the SIF-dedicated filter (C2) having transmission spectral characteristics of about 758 [nm] arranged thereon out of the two types of special purpose filters used for SIF calculation is about 0.125 (in other words, about ⅛ of the output sensitivities of the pixels having the tunable filters (A)) as shown in c-3.

Figure 13:
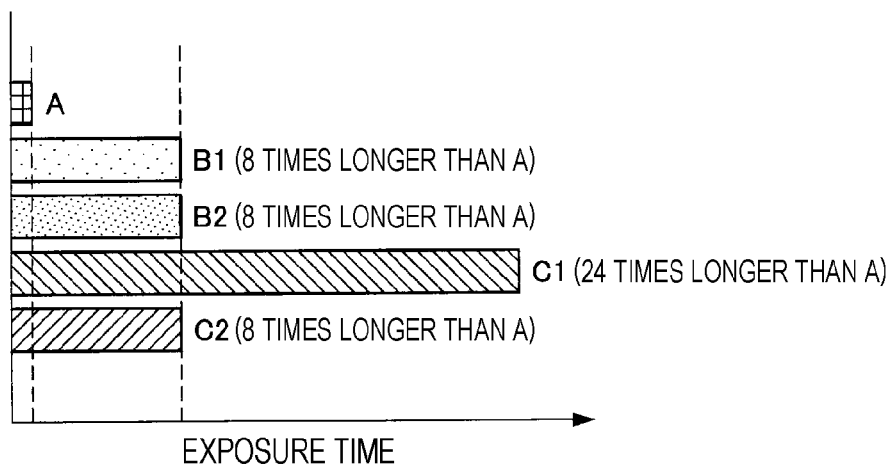
FIG. 13 is a diagram showing exposure times of filters in the first example.

In a case where vegetation is imaged with such output sensitivities, the exposure control unit 130 determines exposure times of the respective pixels according to the output sensitivities of the respective pixels. More specifically, for the pixels having the PRI-dedicated filter (B1), the PRI-dedicated filter (B2), and the SIF-dedicated filter (C2) which have output sensitivities about ⅛ of those of the pixels having the tunable filters (A), the exposure control unit 130 sets the exposure times of these pixels to be about eight times longer than the exposure times of the pixels having the tunable filters (A), as shown in FIG. 13. Further, for the pixel having the SIF-dedicated filter (C1) whose output sensitivity is about 1/24 of those of the pixels having the tunable filters (A), the exposure control unit 130 sets the exposure time of this pixel to be about 24 times longer than the exposure times of the pixels having the tunable filters (A).

Figure 14:
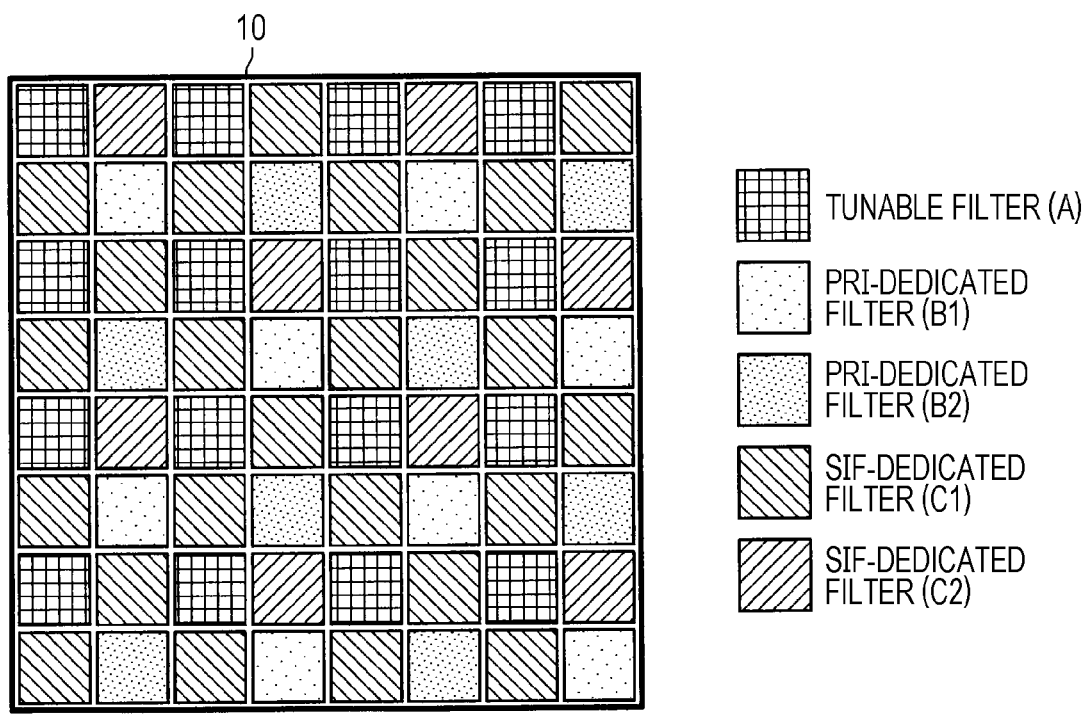
FIG. 14 is a diagram showing a configuration of a filter according to a second example.

(3.2. Second example) Subsequently, a second example will be described. The present example describes a case where the number of pixels on which the respective filters are arranged is adjusted according to output sensitivities. More specifically, the PRI-dedicated filters (B1), the PRI-dedicated filters (B2), and the SIF-dedicated filters (C2) which have output sensitivities about ⅛ of those of the pixels having the tunable filters (A) are each arranged on eight pixels which are eight times those in the first example, as shown in FIG. 14. Further, the SIF-dedicated filters (C1) having output sensitivities about 1/24 of those of the pixels having the tunable filters (A) are arranged on twenty-four pixels which are twenty-four times those in the first example.

Figure 15:
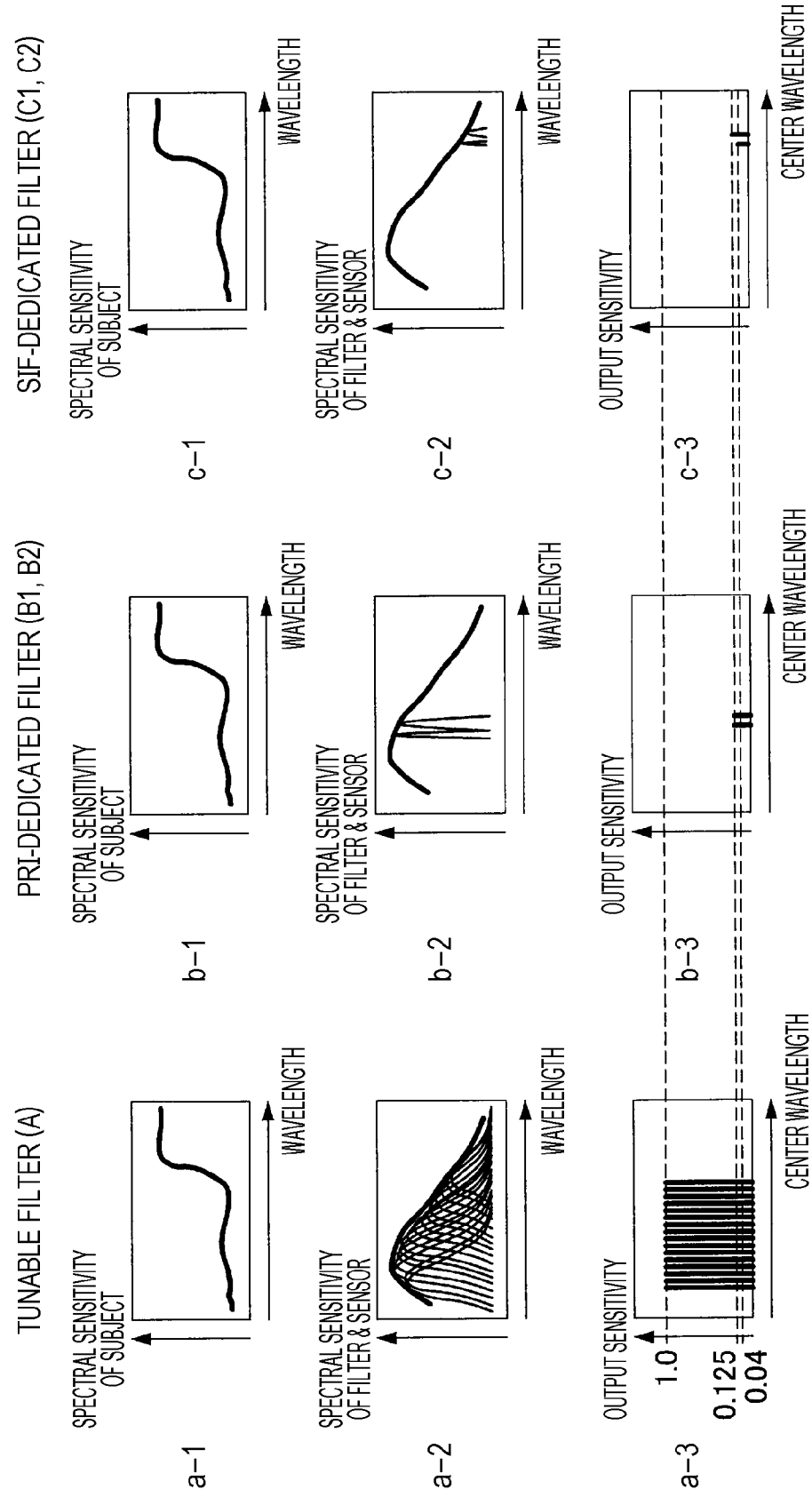
FIG. 15 is a diagram showing output sensitivities, etc. of pixels in the second example.

On the other hand, the tunable filters (A) are arranged on more pixels than twelve pixels in the first example, that is, on sixteen pixels. Due to an increase in the number of pixels having the tunable filters (A), the image capture device 100 can detect light in more wavelength bands as compared with the first example as shown in a-2 and a-3 of FIG. 15, thereby being capable of improving calculation accuracy in tunable wavelength extraction and SNR. Thus, the half bandwidth can be narrowed. The other graphs in FIG. 15 are similar to those in the first example, so that the description thereof will be omitted.

Figure 16:
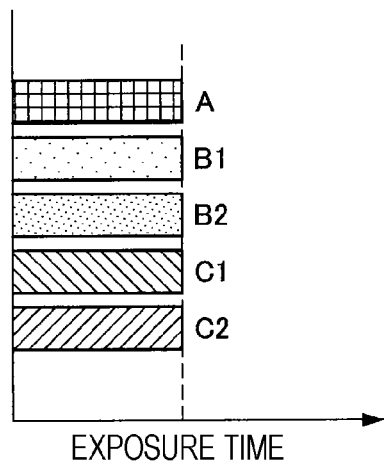
FIG. 16 is a diagram showing exposure times of filters in the second example.

Due to adjusting the number of pixels on which the respective filters are arranged according to output sensitivities as in the present example, the exposure times of the respective pixels are substantially the same as shown in FIG. 16. Thus, the image capture device 100 can perform image capture for all pixels at a time.

Note that, in the first example, the pixels 10 arranged in a 4×4 array correspond to one pixel for sensing, whereas in the present example, an optical low-pass filter is inserted in the stage preceding the filter 140 so that the pixels 10 arranged in an 8×8 array correspond to one pixel for sensing. Therefore, the resolution in the present example is half that in the first example in the vertical and horizontal directions.

3.3. Third Example

Figure 17:
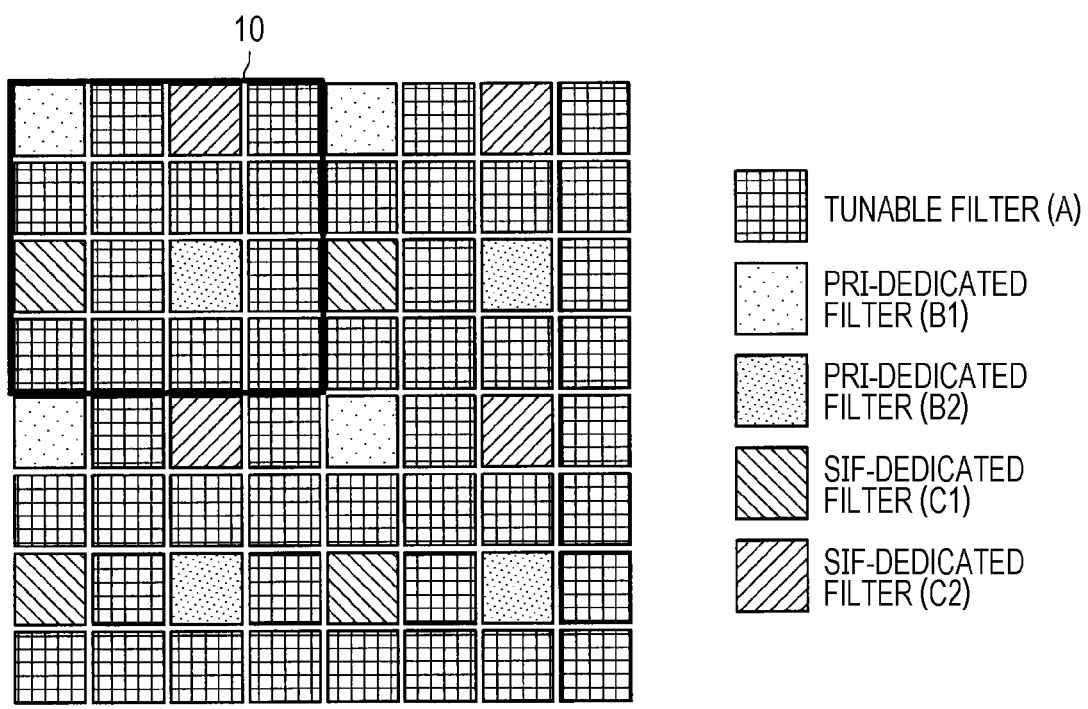
FIG. 17 is a diagram showing a configuration of a filter according to a third example.

Subsequently, a third example will be described. The present example describes a case where the transmittance of each filter is adjusted so that the output sensitivities of the respective pixels are substantially the same. As shown in FIG. 17, in the present example, an optical low-pass filter is inserted in the stage preceding the filter 140 so that the pixels 10 arranged in a 4×4 array correspond to one pixel for sensing, as in the first example. The configurations of the tunable filters (A), the PRI-dedicated filters (B1, B2), and the SIF-dedicated filters (C1, C2) are also similar to those in the first example, and therefore, the description thereof will be omitted.

Figure 18:
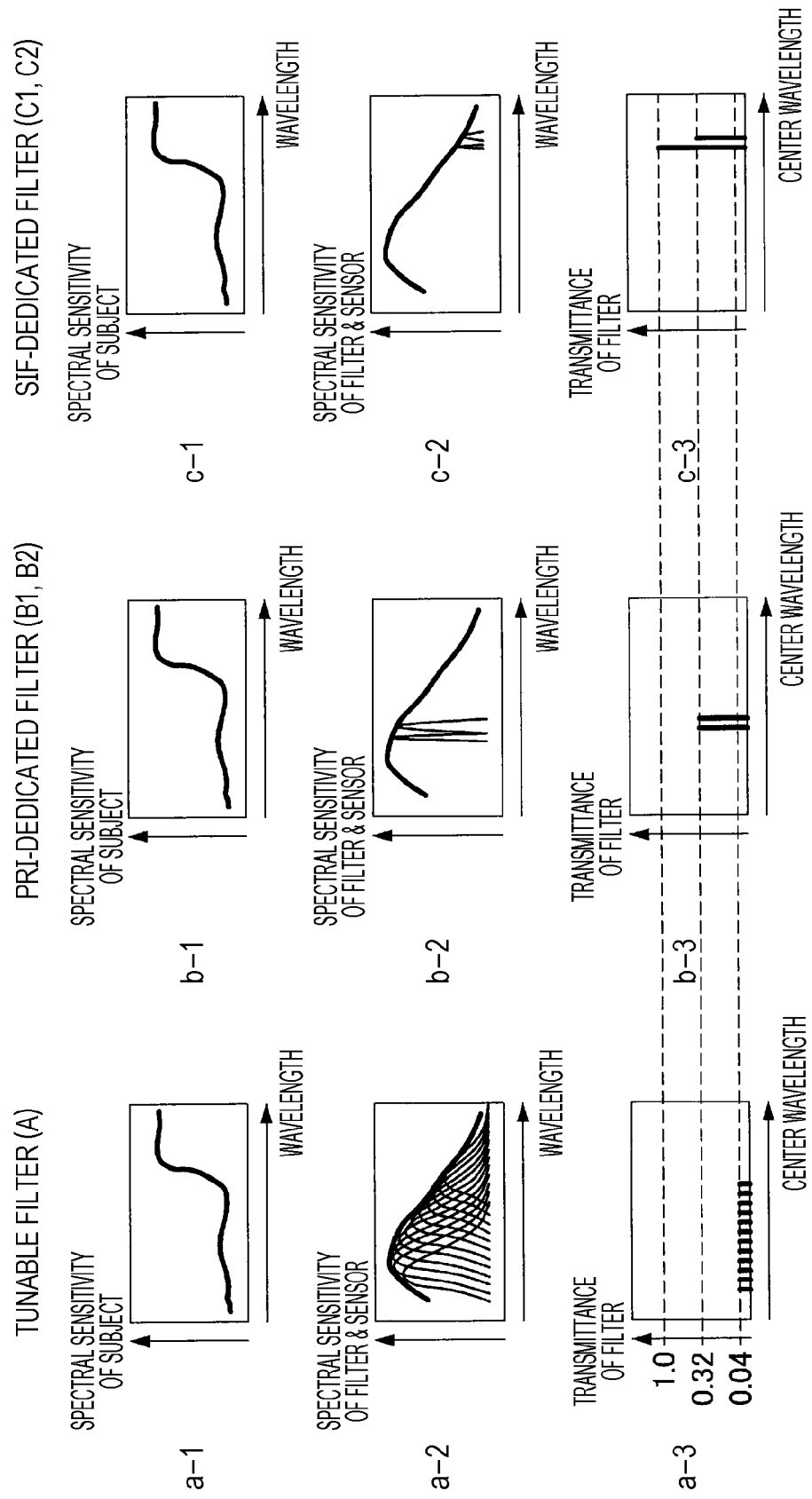
FIG. 18 is a diagram showing output sensitivities, etc. of pixels in the third example.
Figure 19:
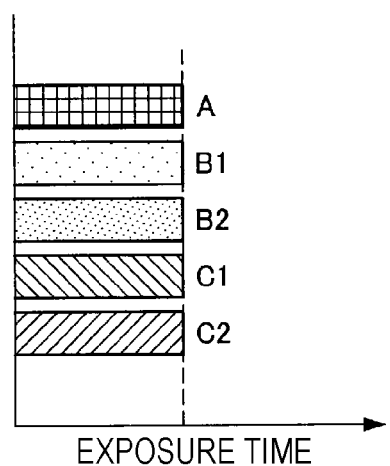
FIG. 19 is a diagram showing exposure times of filters in the third example.

In the present example, it is assumed that the transmittance of the SIF-dedicated filter (C1) having the lowest pixel output sensitivity is adjusted to 1.0, the transmittances of the PRI-dedicated filter (B1), the PRI-dedicated filter (B2), and the SIF-dedicated filter (C2) are adjusted to 0.32, and the transmittance of each tunable filter (A) is adjusted to 0.04, as shown in a-3, b-3, and c-3 of FIG. 18. Note that the other graphs in FIG. 18 are similar to those in the first example, so that the description thereof will be omitted. With this configuration, the exposure times of the respective pixels are substantially the same as shown in FIG. 19, whereby the image capture device 100 can perform image capture for all pixels at a time.

Note that, in the present example, the pixels 10 arranged in a 4×4 array correspond to one pixel for sensing as in the first example, and therefore, the resolution in the present example is substantially the same as that of the first example. Further, since the transmittance of each filter is adjusted with the transmittance of the SIF-dedicated filter (C1) having the lowest pixel output sensitivity being used as a reference, the exposure time of the entire pixel becomes longer than that in the first example. Therefore, the present example is more suitable for a case where the subject is a still object or the like that requires a relatively high resolution, and the illuminance is relatively high.

3.4. Fourth Example

Subsequently, a fourth example will be described. The present example describes a case where the image capture device 100 includes three image capture mechanisms, and the tunable filters (A), the PRI-dedicated filters (B1, B2), and the SIF-dedicated filters (C1, C2) are arranged on different image sensors 150.

In this case, various combinations of the configuration of one pixel for sensing and the exposure times can be considered. For example, regarding the tunable filters (A), sixteen types of pixels arranged in a 4×4 array are set as one pixel for sensing as shown in d-1 of FIG. 20. Further, regarding the PRI-dedicated filter (B1) and the PRI-dedicated filter (B2), pixels in a 4×4 array including eight pixels having the PRI-dedicated filters (B1) and eight pixels having the PRI-dedicated filters (B2) are set as one pixel for sensing. Furthermore, regarding the SIF-dedicated filter (C1) and the SIF-dedicated filter (C2), pixels in a 4×4 array including twelve pixels having the SIF-dedicated filters (C1) and four pixels having the SIF-dedicated filters (C2) are set as one pixel for sensing.

In this configuration, the output sensitivity of one pixel for sensing is substantially the same between the tunable filters (A) and the PRI-dedicated filters (B1, B2), whereas the output sensitivity of one pixel for sensing regarding the SIF-dedicated filters (C1, C2) is about a half of the output sensitivities of the tunable filters (A) and the PRI-dedicated filters (B1, B2). Therefore, as shown in d-1 of FIG. 21, the exposure control unit 130 sets the exposure times of the pixels having the tunable filters (A) and pixels having the PRI-dedicated filters (B1, B2) to be substantially the same, and sets the exposure times of the pixels having the SIF-dedicated filters (C1, C2) to be two times longer than the exposure times of the pixels having the tunable filters (A) and the PRI-dedicated filters (B1, B2).

Figure 20:
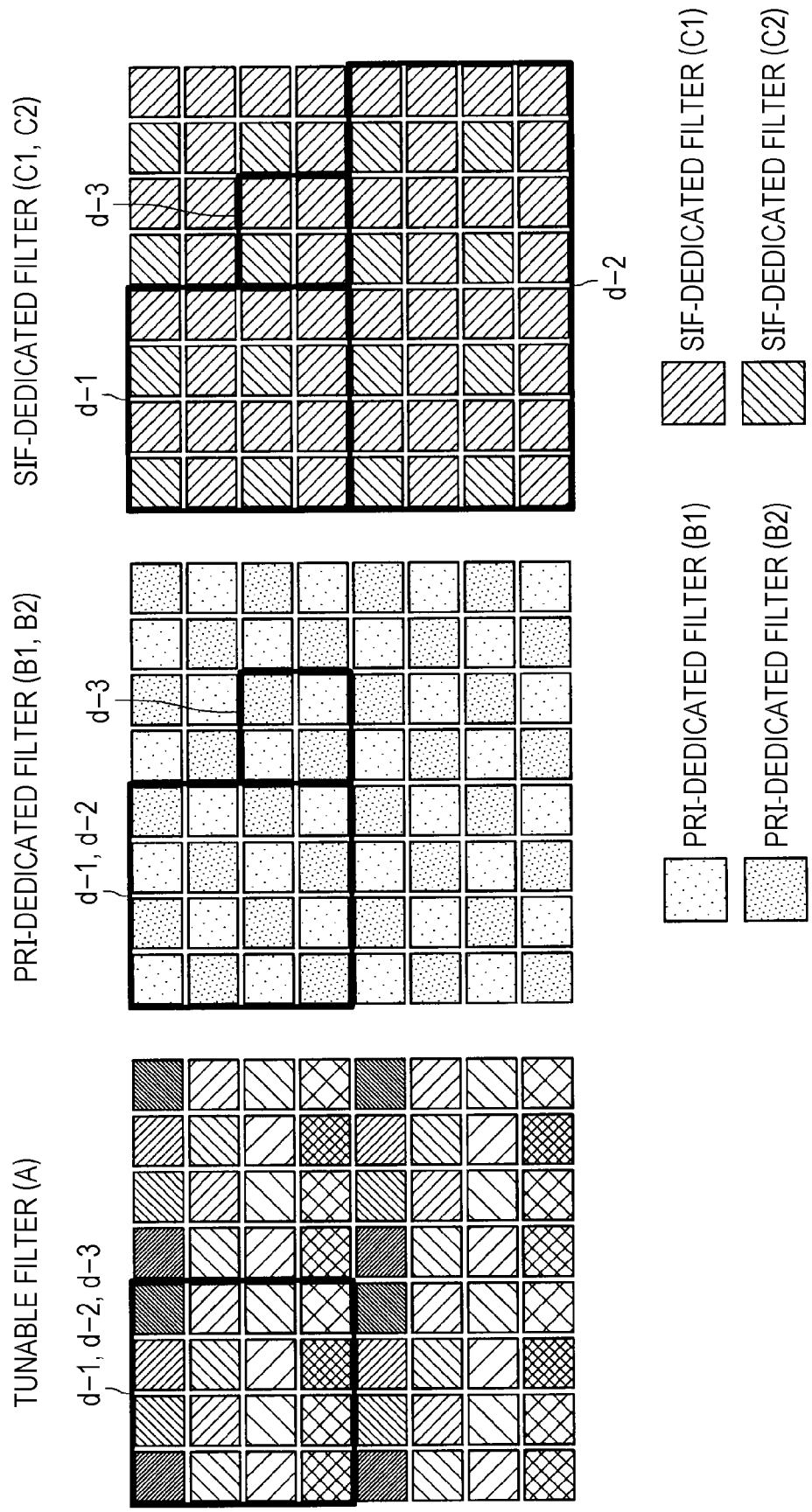
FIG. 20 is a diagram showing a configuration of a filter according to a fourth example.

Further, consider the case where, regarding the SIF-dedicated filters (C1, C2), pixels in a 4×8 (or 8×4) array including twenty-four pixels having the SIF-dedicated filters (C1) and eight pixels having the SIF-dedicated filters (C2) are set as one pixel for sensing as shown in d-2 of FIG. 20 (notably, the configurations of the tunable filters (A) and the PRI-dedicated filters (B1, B2) are similar to those shown in d-1 of FIG. 20). In this configuration, the exposure control unit 130 sets the exposure times of the pixels having the tunable filters (A), the PRI-dedicated filters (B1, B2), and the SIF-dedicated filters (C1, C2) to be substantially the same as shown in d-2 of FIG. 21.

Further, consider the case where, regarding the PRI-dedicated filters (B1, B2), pixels in a 2×2 array including two pixels having the PRI-dedicated filters B1 and two pixels having the PRI-dedicated filters B2 are set as one pixel for sensing in order to place a priority on resolution, and regarding the SIF-dedicated filters (C1, C2), pixels in a 2×2 array including three pixels having the SIF-dedicated filters (C1) and one pixel having the SIF-dedicated filter (C2) are similarly set as one pixel for sensing in order to place a priority on resolution as shown in d-3 of FIG. 20 (notably, the configurations of the tunable filters (A) are similar to those in d-1 of FIG. 20). In this configuration, as shown in d-3 of FIG. 21, the exposure control unit 130 sets the exposure times of the pixels having the PRI-dedicated filters (B1, B2) to be about four times longer than the exposure times of the pixels having the tunable filters (A), and sets the exposure times of the pixels having the SIF-dedicated filters (C1, C2) to be about eight times longer than the exposure times of the pixels having the tunable filters (A).

Note that optical low-pass filters are assumed to be inserted in a stage preceding the respective filters according to the size of one pixel for sensing as in the abovementioned examples.

3.5. Fifth Example

Figure 22:
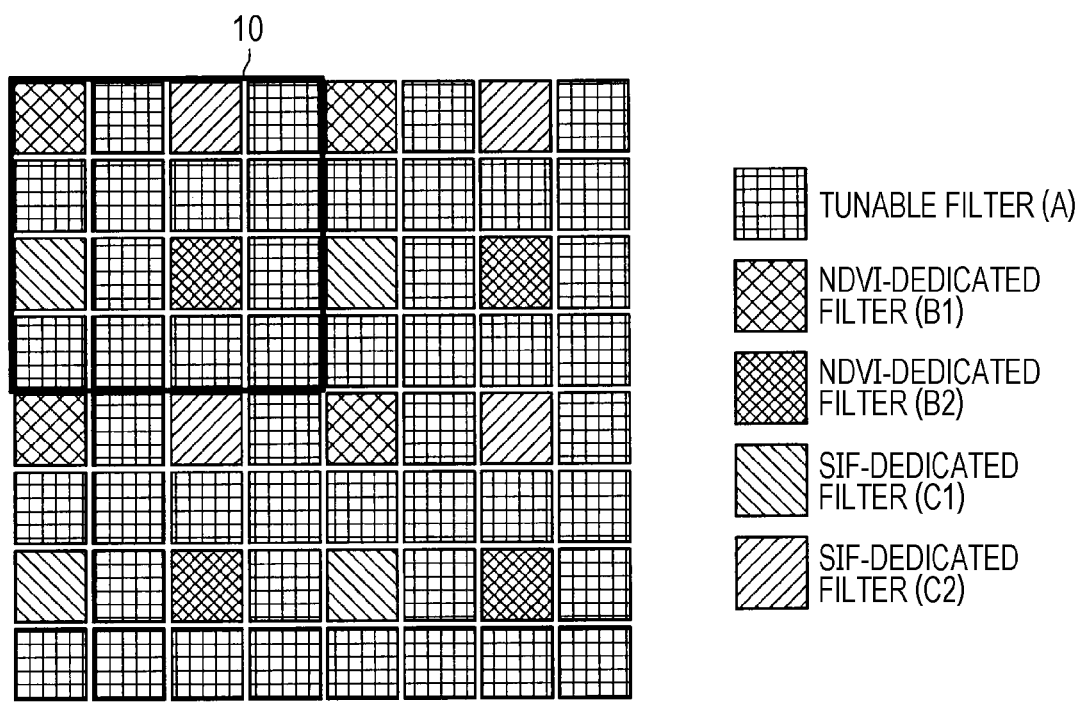
FIG. 22 is a diagram showing a configuration of a filter according to a fifth example.

Subsequently, a fifth example will be described. The present example describes a case where the PRI-dedicated filter serving as the special purpose filter is replaced with an NDVI-dedicated filter. More specifically, in the present example, an optical low-pass filter is inserted in a stage preceding the filter 140 so that the pixels 10 arranged in a 4×4 array correspond to one pixel for sensing as shown in FIG. 22. In addition, among the pixels arranged in a 4×4 array, two types of special purpose filters used for NDVI calculation (NDVI-dedicated filter (B1) having transmission spectral characteristic of wavelength of 650 [nm] in a wavelength band of red light (RED) and a half bandwidth of 50 to 100 [nm], and NDVI-dedicated filter (B2) having transmission spectral characteristics of a wavelength of 800 [nm] in a wavelength band of NIR and a half bandwidth of 50 to 100 [nm]) are arranged on two pixels, respectively (two pixels in total), and the SIF-dedicated filters (C1, C2) are arranged on two pixels, respectively (two pixels in total). In addition, the tunable filters (A) are arranged on the remaining twelve pixels.

Here, it is assumed that the subject is vegetation. In a case where a signal of a visible range is detected, an NIR signal may often become a large noise source, because the NIR signal is larger than the signal of a visible range. In view of this, in the present example, the transmission spectral characteristics of the tunable filters (A) are forcibly limited to the visible range (a frame line 12 in a-3 of FIG. 23 indicates the visible range), as shown in a-3 of FIG. 23. Then, the image capture device 100 acquires signals of red light (RED) and NIR from the pixels having the NDVI-dedicated filters (B1, B2), not from the pixels having the tunable filters (A). Accordingly, the image capture device 100 can improve the accuracy of NDVI, and can also improve the accuracy of the signal obtained by the pixels having the tunable filters (A).

Note that the method for forcibly limiting the transmission spectral characteristics of the tunable filters (A) to the visible range is not particularly limited. For example, filters having transmission spectral characteristics in the visible range may be used as the tunable filters (A), or another filter having a transmission spectral characteristic in the visible range may be mounted in the stage preceding the tunable filters (A).

Further, although the present example describes the case where an image of a wavelength band of red light is acquired by the pixel having the NDVI-dedicated filter (B1), it is not limited thereto. More specifically, an image of a wavelength band of red light may be acquired by the pixels having the tunable filters (A) as in the abovementioned examples.

Figure 23:
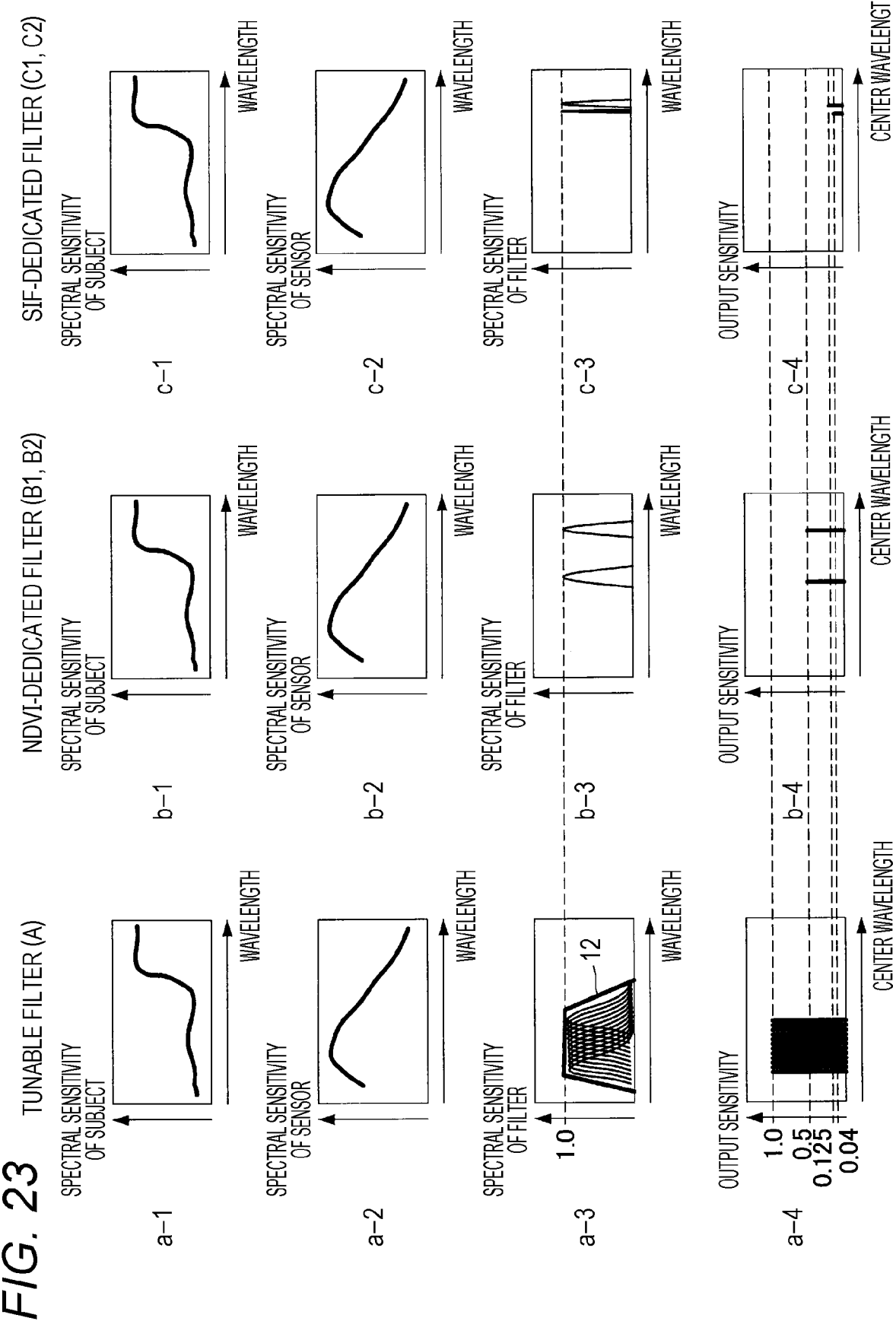
FIG. 23 is a diagram showing output sensitivities, etc. of pixels in the fifth example.

Further, it is assumed that the output sensitivities of the pixels having the tunable filters (A) are about 1.0, and the output sensitivities of the pixels having the NDVI-dedicated filters (B1, B2) are about 0.5 (in other words, about ½ of the output sensitivities of the pixels having the tunable filters (A)), as shown in a-4, b-4, and c-4 of FIG. 23. Further, it is assumed that the output sensitivity of the pixel having the SIF-dedicated filter (C1) having a transmission spectral characteristic of 761 [nm] is about 0.04 (in other words, about ¹⁄₂₄ of the output sensitivities of the pixels having the tunable filters (A)), and the output sensitivity of the pixel having the SIF-dedicated filter (C2) having a transmission spectral characteristic of 758 [nm] is about 0.125 (in other words, about ⅛ of the output sensitivities of the pixels having the tunable filters (A)).

Figure 24:
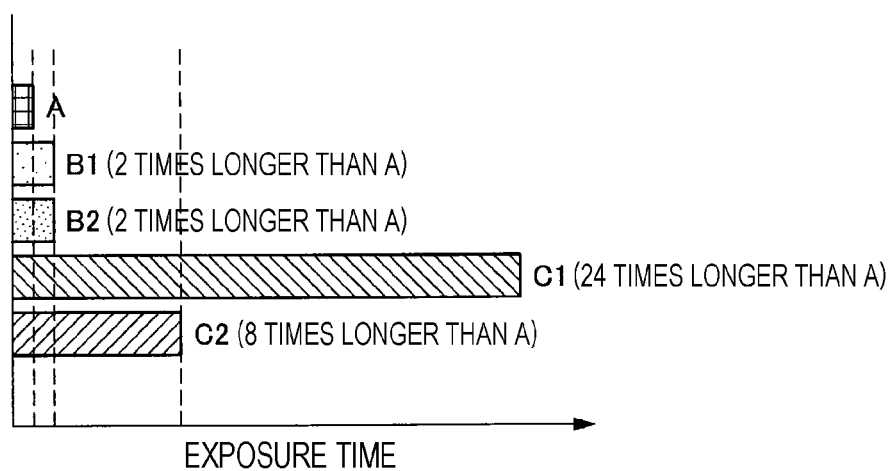
FIG. 24 is a diagram showing exposure times of filters in the fifth example.

The exposure time of each pixel when an image of vegetation is captured with such output sensitivities will be described. As shown in FIG. 24, the exposure control unit 130 sets the exposure times of the pixels of the NDVI-dedicated filters (B1, B2) whose output sensitivities are about ½ of the output sensitivities of the pixels having the tunable filters (A) to be about two times longer than the exposure times of the pixels having the tunable filters (A). Further, the exposure control unit 130 sets the exposure time of the pixel of the SIF-dedicated filter (C1) whose output sensitivity is about ¹⁄₂₄ of the output sensitivities of the pixels having the tunable filters (A) to be about twenty-four times longer than the exposure times of the pixels having the tunable filters (A). Further, the exposure control unit 130 sets the exposure time of the pixel of the SIF-dedicated filter (C2) whose output sensitivity is about ⅛ of the output sensitivities of the pixels having the tunable filters (A) to be about eight times longer than the exposure times of the pixels having the tunable filters (A).

Next, an example of a case where the present example is achieved by the image capture device 100 including three image capture mechanisms will be described. For example, regarding the tunable filters (A), nine types of pixels arranged in a 3×3 array are set as one pixel for sensing as shown in d-1 of FIG. 25. With this configuration, the resolution is higher than that in the example in which sixteen types of pixels arranged in a 4×4 array are used as one pixel for sensing. Further, regarding the NDVI-dedicated filters (B1, B2), pixels in a 2×2 array including two pixels having the NDVI-dedicated filters (B1) and two pixels having the NDVI-dedicated filters (B2) are set as one pixel for sensing. Furthermore, regarding the SIF-dedicated filters (C1, C2), pixels in a 4×4 array including twelve pixels having the SIF-dedicated filters (C1) and four pixels having the SIF-dedicated filters (C2) are set as one pixel for sensing.

In this configuration, the output sensitivity of one pixel for sensing is substantially the same between the tunable filters (A) and the NDVI-dedicated filters (B1, B2), whereas the output sensitivity of one pixel for sensing regarding the SIF-dedicated filters (C1, C2) is about a half of the output sensitivities of the tunable filters (A) and the NDVI-dedicated filters (B1, B2). Therefore, as shown in d-1 of FIG. 26, the exposure control unit 130 sets the exposure times of the tunable filters (A) and the NDVI-dedicated filters (B1, B2) to be substantially the same, and sets the exposure times of the SIF-dedicated filters (C1, C2) to be about two times longer than the exposure times of the pixels having the tunable filters (A) and the pixels having the NDVI-dedicated filters (B1, B2).

Figure 25:
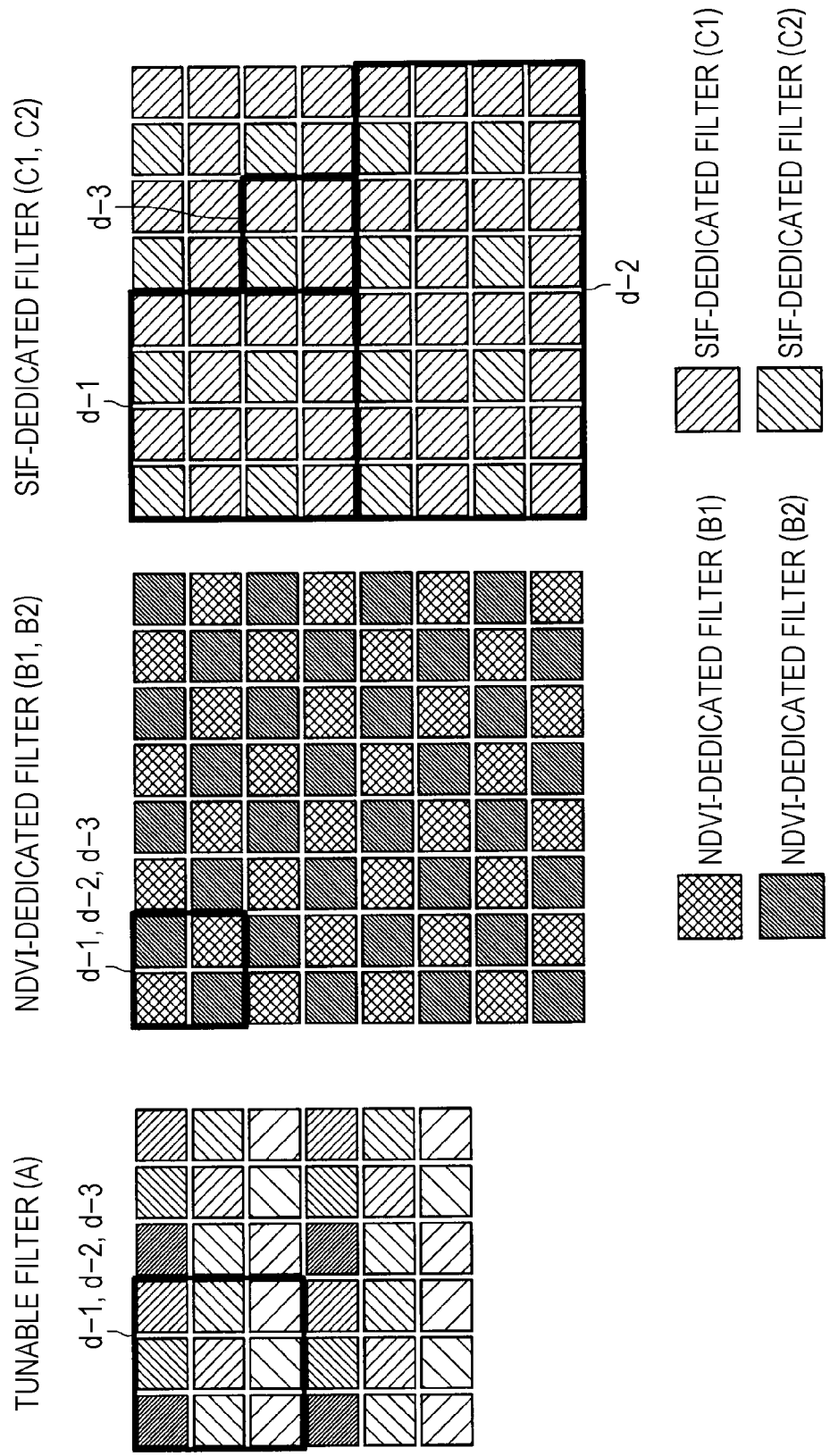
FIG. 25 is a diagram showing a configuration of a filter in a case where the fifth example is achieved by an image capture device 100 including three image capture mechanisms.

Further, consider the case where, regarding the SIF-dedicated filters (C1, C2), pixels in a 4×8 (or 8×4) array including twenty-four pixels having the SIF-dedicated filters (C1) and eight pixels having the SIF-dedicated filters (C2) are set as one pixel for sensing as shown in d-2 of FIG. 25 (notably, the configurations of the tunable filters (A) and the NDVI-dedicated filters (B1, B2) are similar to those shown in d-1 of FIG. 25). In this configuration, the exposure control unit 130 sets the exposure times of the pixels having the tunable filters (A), the NDVI-dedicated filters (B1, B2), and the SIF-dedicated filters (C1, C2) to be substantially the same as shown in d-2 of FIG. 26.

Further, consider the case where, regarding the SIF-dedicated filters (C1, C2), pixels in a 2×2 array including three pixels having the SIF-dedicated filters (C1) and one pixel having the SIF-dedicated filter (C2) are set as one pixel for sensing as shown in d-3 of FIG. 25 in order to place a priority on resolution (notably, the configurations of the tunable filters (A) and the NDVI-dedicated filters (B1, B2) are similar to those shown in d-1 of FIG. 25). In this configuration, as shown in d-3 of FIG. 26, the exposure control unit 130 sets the exposure times of the pixels having the tunable filters (A) and the pixels having the NDVI-dedicated filters (B1, B2) to be substantially the same, and sets the exposure times of the pixels having the SIF-dedicated filters (C1, C2) to be about eight times longer than the exposure times of the pixels having the tunable filters (A) and the pixels having the NDVI-dedicated filters (B1, B2).

Note that optical low-pass filters are assumed to be inserted in a stage preceding the respective filters according to the size of one pixel for sensing as in the abovementioned examples.

3.6. Sixth Example

Subsequently, a sixth example will be described. The present example shows a case in which the image capture mechanism equipped with the SIF-dedicated filters (C1, C2) according to the fifth example (FIG. 25) is changed to an RGB camera. More specifically, regarding the RGB cameras (C1, C2, C3), pixels in a 2×2 array including one pixel having a filter for red light (RGB camera (C1)), two pixels having filters for green light (RGB camera (C2)), and one pixel having a filter for blue light (RGB camera (C3)) are set as one pixel for sensing as shown FIG. 27 (notably, the configurations of the tunable filters (A) and the NDVI-dedicated filters (B1, B2) are similar to those shown in FIG. 25). In this case, it is assumed that the output sensitivities of the pixels of the RGB cameras (C1, C2, C3) are adjusted to be about 1.0, respectively, as shown in c-3 of FIG. 28.

Figure 29:
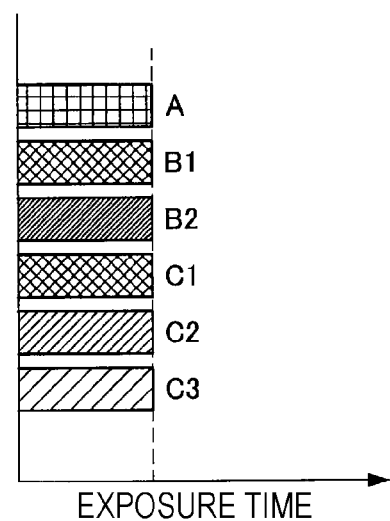
FIG. 29 is a diagram showing exposure times of filters in the sixth example.

The exposure time of each pixel when an image of vegetation is captured with such output sensitivities will be described. As shown in FIG. 29, the exposure control unit 130 sets the exposure times of the pixels having the tunable filters (A), the NDVI-dedicated filters (B1, B2), and the RGB cameras (C1, C2, C3) to be substantially the same.

In this example, an optical low-pass filter is also inserted in a stage preceding the filter 140 according to the number of pixels corresponding to one pixel for sensing. However, since advanced demosaicing is applied to the RGB Bayer array, an optical low-pass filter is often inserted according to the sample interval of GRN for modulation transfer function (MTF).

3.7. Seventh Example

Figure 30:
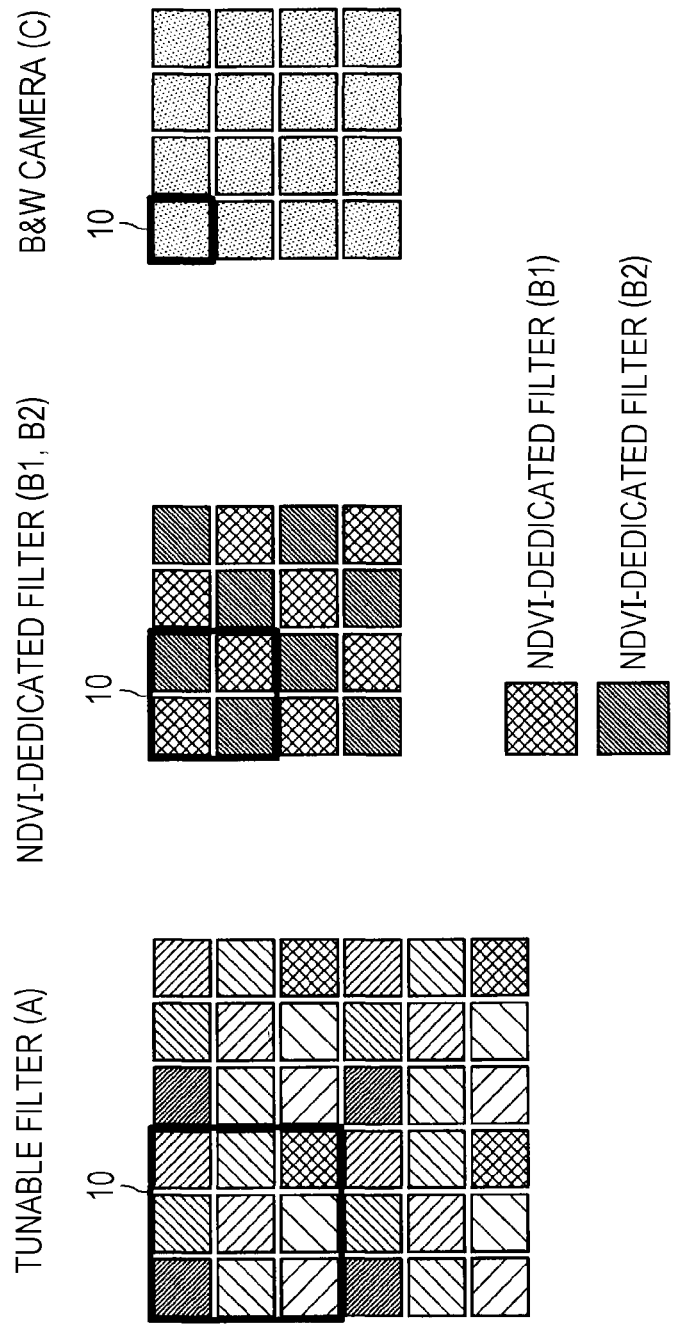
FIG. 30 is a diagram showing a configuration of a filter according to a seventh example.
Figure 31:
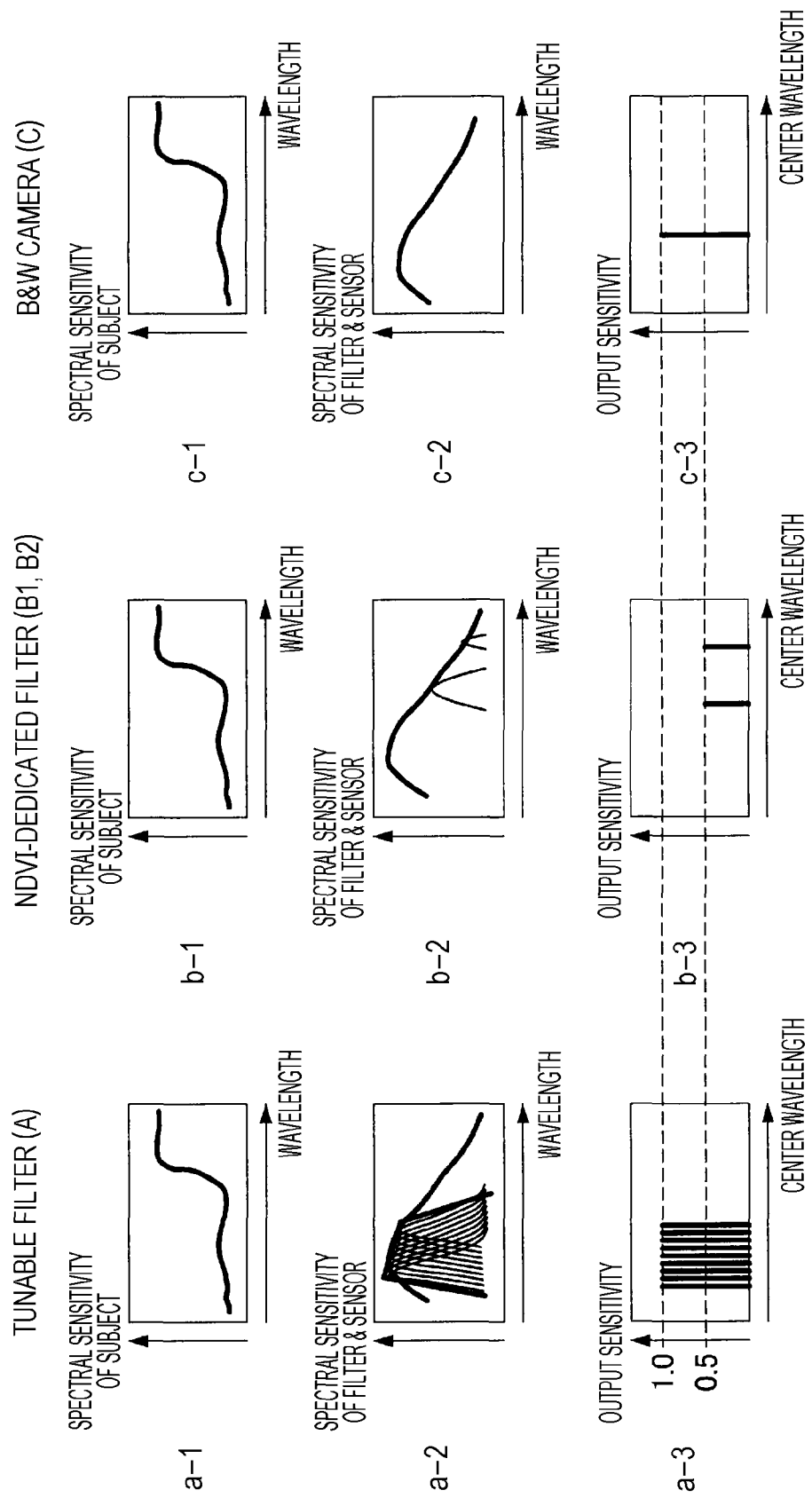
FIG. 31 is a diagram showing output sensitivities, etc. of pixels in the seventh example.

Subsequently, a seventh example will be described. As shown in FIG. 30, this example shows a case in which a B & W camera (or a monochrome camera) is used instead of the RGB camera used in the sixth example. In this case, it is assumed that the output sensitivity of a pixel of the B & W camera (C) is adjusted to be about 1.0 as shown in c-3 of FIG. 31.

Figure 32:
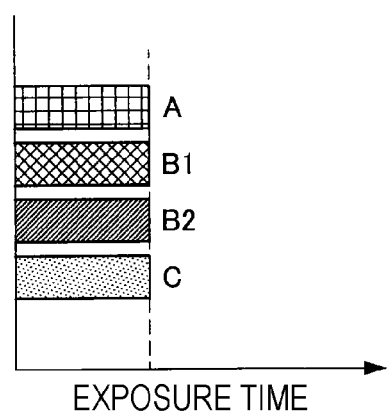
FIG. 32 is a diagram showing exposure times of filters in the seventh example.

The exposure time of each pixel when an image of vegetation is captured with such output sensitivities will be described. As shown in FIG. 32, the exposure control unit 130 sets the exposure times of the pixels having the tunable filters (A), the NDVI-dedicated filters (B1, B2), and the B & W camera (C) to be substantially the same.

Figure 33:
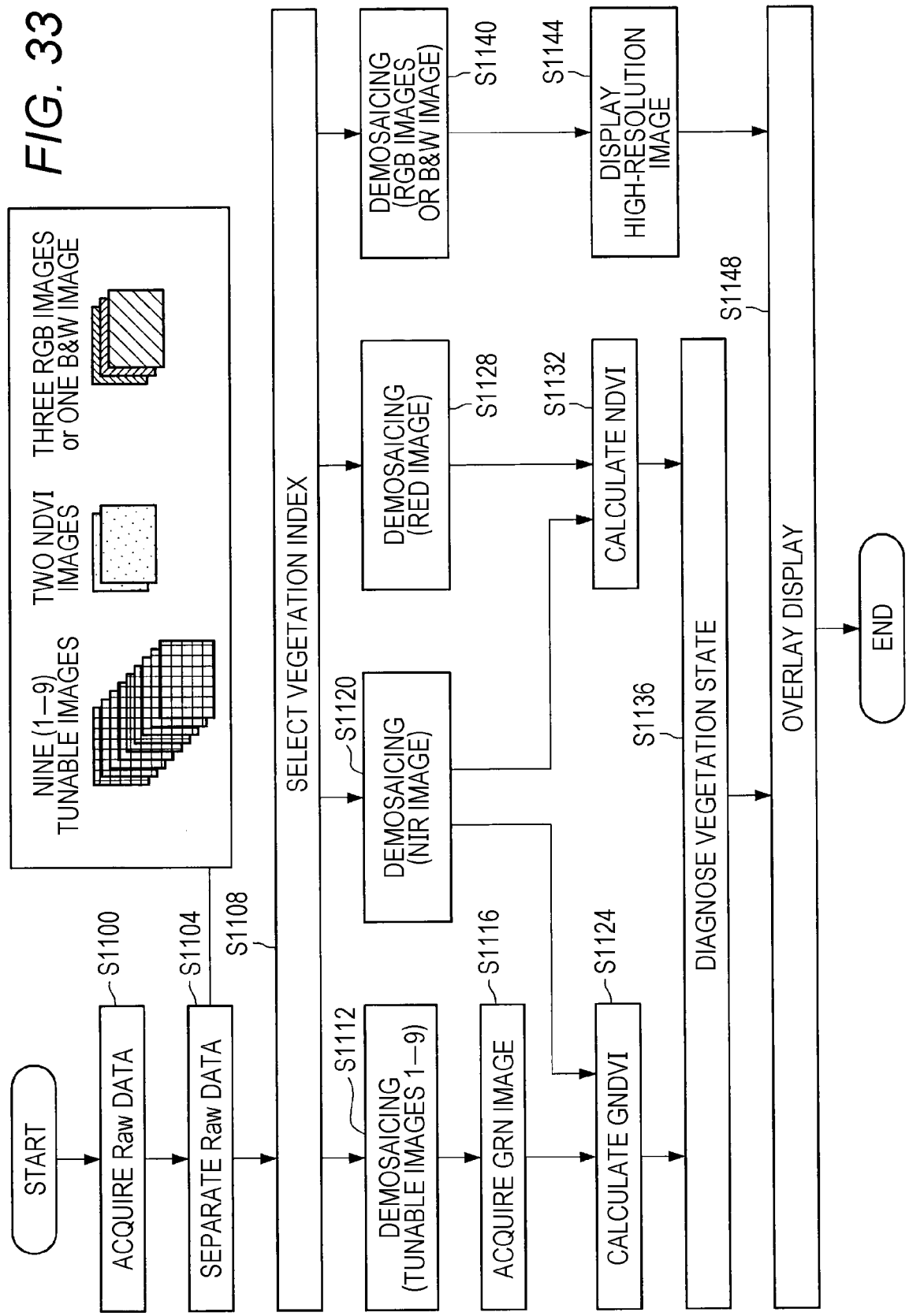
FIG. 33 is a flowchart showing an example of a flow of signal processing in a case where an RGB camera or a B & W camera is installed.

Here, advantages of mounting the RGB camera in the sixth example and mounting the B & W camera in the seventh example will be described with reference to FIG. 33. FIG. 33 is a flowchart showing an example of the flow of signal processing in a case where an RGB camera or a B & W camera is installed. Although the information processing device 200a or the cloud server 200b which is an external device can achieve the function of the signal processing unit 170 of the image capture device 100 as described above, a case where the signal processing unit 170 of the image capture device 100 achieves all of the signal processing will be described below as one example.

In step S1100, the signal processing unit 170 of the image capture device 100 acquires raw data generated by the image sensor 150 via the output unit 160. In step S1104, the signal processing unit 170 separates the acquired raw data for each filter, and thus, nine tunable images, two images for NDVI (an image of a wavelength band of red light (RED) and an image of an NIR wavelength band), and three images of wavelength bands of RGB or one B & W (or monochrome) image are obtained. In step S1108, the user selects the vegetation index to be calculated.

When the user selects GNDVI as the vegetation index to be calculated, the signal processing unit 170 performs demosaicing on nine tunable images in step S1112, and obtains an image of a wavelength band (wavelength: about 550 [nm]) of green light in step S1116. Thereafter, the signal processing unit 170 performs demosaicing on the image of an NIR wavelength band (wavelength: about 800 [nm]) in step S1120, and calculates GNDVI through calculation of (Equation 2) described above using the image of the NIR wavelength band and the image of the wavelength band of green light in step S1124.

When the user selects NDVI as the vegetation index to be calculated in step S1108, the signal processing unit 170 performs demosaicing on the image of the NIR wavelength band in step S1120, and performs demosaicing on the image of the wavelength band of red light (wavelength: about 650

[nm]) in step S1128. In step S1132, the signal processing unit 170 calculates the NDVI through calculation of (Equation 1) described above using the image of the NIR wavelength band and the image of the wavelength band for red light. In step S1136, the signal processing unit 170 diagnoses the state of vegetation on the basis of the GNDVI or NDVI calculated in the previous stage.

In step S1140, the signal processing unit 170 performs demosaicing on the images of wavelength bands of RGB or the B & W image. Thereafter, the signal processing unit 170 displays the high-resolution images of the RGB wavelength bands or the B & W image on the display in step S1144, and overlays and displays (superimposes and displays) the low-resolution image of vegetation index of GNDVI or NDVI on the image in step S1148. Thus, a series of processing ends (in this case, the signal processing unit 170 also functions as a display control unit). Accordingly, the image capture device 100 displays the high-resolution images of RGB wavelength bands or B & W image in a recognizable manner, while keeping high accuracy of the image of the vegetation index of GNDVI or NDVI, whereby an area having problems can be easily identified.

Note that the processes of steps in the flowchart shown in FIG. 33 are not necessarily performed in time series in the described order. That is, the processes of the respective steps in the flowchart may be performed in an order different from the described order, or may be performed in parallel. Further, although the GNDVI or NDVI is used as the vegetation index in the above description, PRI or SIF may be calculated and displayed as overlaid. Further, in step S1112, step S1120, step S1128, and step S1140, demosaicing is not always necessary and may be appropriately omitted depending on the acquired image data.

3.8. Eighth Example

Figure 34:
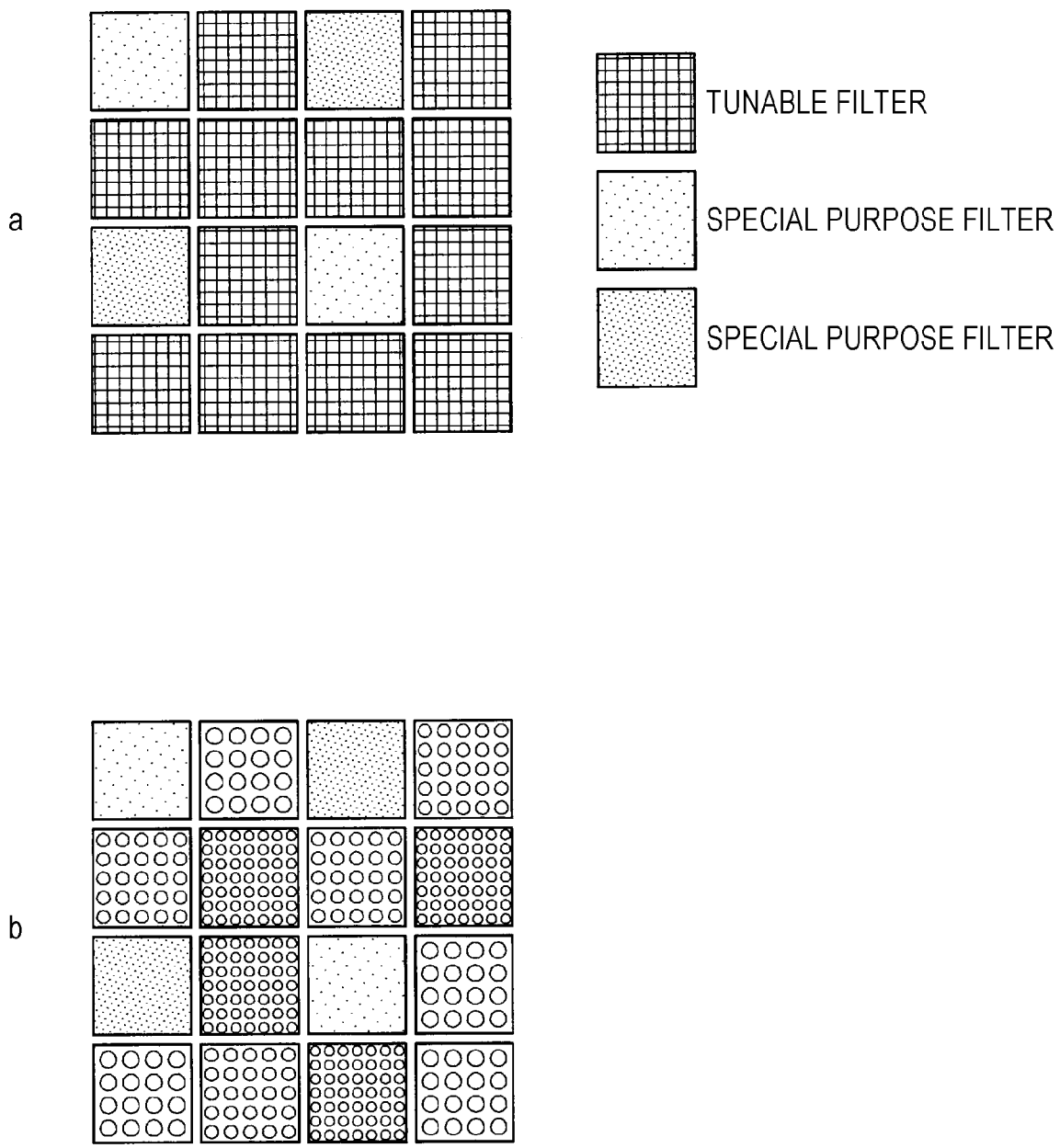
FIG. 34 is a diagram showing a method for constructing a tunable filter and a special purpose filter in an eighth example.

In the above, the combination of the tunable filter and the special purpose filter, the exposure control, etc. have been described. Next, a method for constructing the tunable filter and the special purpose filter will be described with reference to FIG. 34.

a of FIG. 34 shows an example of tunable filters and special purpose filters in which pixel-level microfilters are arranged in an array. A microfilter is formed by, for example, depositing a multilayer dielectric film on glass of several [nm] to several [μm], and its transmission spectral characteristics (for example, the wavelength band of light that can be transmitted, half bandwidth, etc.) are not particularly limited.

b of FIG. 34 shows an example of a case in which the tunable filters are constituted by plasmon resonance filters using the principle of plasmon resonance, and the special purpose filters are formed by arranging pixel-level microfilters in an array as in a of FIG. 34. The plasmon resonance filter is a filter in which dozens to hundreds holes, each having a size of several [nm], are formed in a single metal plate, and the wavelength band of light that can be transmitted changes depending on the hole diameter and pitch. Note that the hole diameter and pitch of the plasmon resonance filter are not particularly limited.

Next described is an example of a case in which special purpose filters for PRI and SIF are achieved by a combination of an RGB sensor and a dual band pass filter (hereinafter sometimes referred to as "DBP"). Consider a case in which a camera (hereinafter, referred to as "DBP1 camera") equipped with a DBP1 having transmission spectral characteristics of about 531 [nm] and about 761 [nm] and a camera (hereinafter, referred to as "DBP2 camera") equipped with a DBP2 having transmission spectral characteristics of about 570 [nm] and about 758 [nm] are used as shown in FIG. 35.

Figure 35:
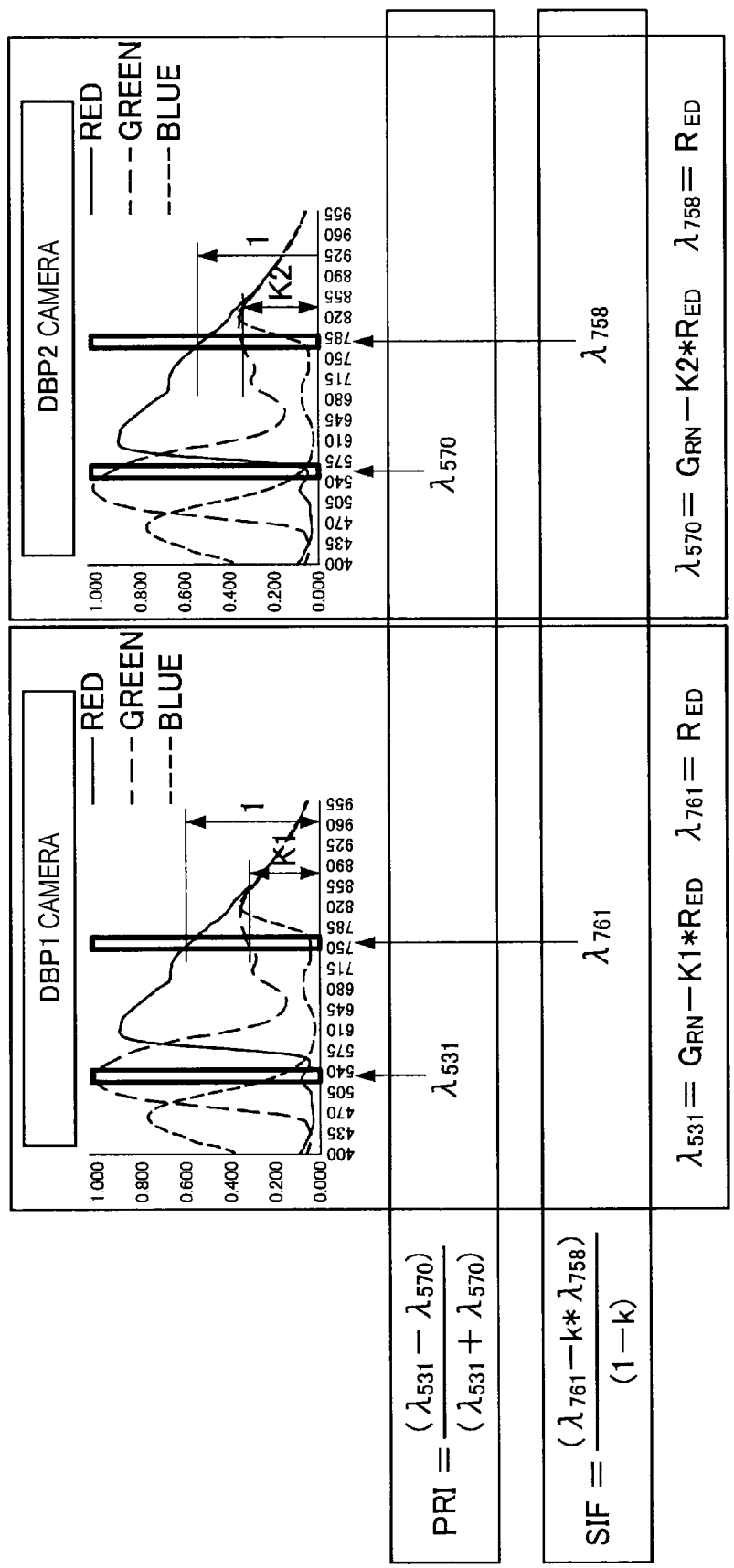
FIG. 35 is a diagram showing an example of a case in which special purpose filters for PRI and SIF are achieved by combining an RGB sensor and a dual bandpass filter.

Then, as shown in FIG. 35, an image of a wavelength band of approximately 761 [nm] is extracted by acquiring pixels of a wavelength band for red light (RED) in the DBP1 camera. Further, an image having both a wavelength band of about 531 [nm] and a wavelength band of about 761 [nm] is extracted by acquiring a pixel of a wavelength band for green light (GRN). The ratio between the wavelength band of about 531 [nm] and the wavelength band of about 761 [nm] is represented by K1, where K1 is an output of a pixel of a wavelength band for green light (GRN) when the output of the pixel of a wavelength band for red light (RED) is defined as 1, as shown in FIG. 35. That is, an image $\lambda_{531}$ of a wavelength band of about 531 [nm] is calculated by the following (Equation 5). Note that "GRN" in (Equation 5) indicates the output of the pixel of the wavelength band for green light (GRN). Further, "RED" indicates the output of the pixel of the wavelength band for red light (RED), and is an image $\lambda 761$ of the wavelength band of about 761 [nm] as described above.

[Equation 5]

$$\lambda_{531} = GRN - K1*RED \quad \text{(Equation 5)}$$

Further, as shown in FIG. 35, an image of a wavelength band of approximately 758 [nm] is extracted by acquiring pixels of a wavelength band for red light (RED) in the DBP2 camera. Further, an image having both a wavelength band of about 570 [nm] and a wavelength band of about 758 [nm] is extracted by acquiring pixels of a wavelength band for green light (GRN). The ratio between the wavelength band of about 570 [nm] and the wavelength band of about 758 [nm] is represented by K2, where K2 is an output of a pixel of a wavelength band for green light (GRN) when the output of the pixel of a wavelength band for red light (RED) is defined as 1, as shown in FIG. 35. That is, an image $\lambda_{570}$ of the wavelength band of about 570 [nm] is calculated by the following (Equation 6). Note that "GRN" in (Equation 6) indicates the output of the pixel of the wavelength band for green light (GRN). Further, "RED" indicates the output of the pixel of the wavelength band for red light (RED), and is an image $\lambda_{758}$ of the wavelength band of about 758 [nm] as described above.

[Equation 6]

$$\lambda_{570} = GRN - K2*RED \quad \text{(Equation 6)}$$

Then, the signal processing unit 170 can calculate the PRI through calculation of the abovementioned (Equation 3) using the image $\lambda_{531}$ of the wavelength band of about 531 [nm] obtained from the DBP1 camera and the image $\lambda_{570}$ of the wavelength band of about 570 [nm] obtained from the DBP2 camera. In addition, the signal processing unit 170 can calculate the SIF through calculation of the abovementioned (Equation 4) using the image $\lambda_{761}$ of the wavelength band of about 761 [nm] obtained from the DBP1 camera and the image $\lambda_{758}$ of the wavelength band of about 758 [nm] obtained from the DBP2 camera.

3.9. Ninth Example

Figure 27:
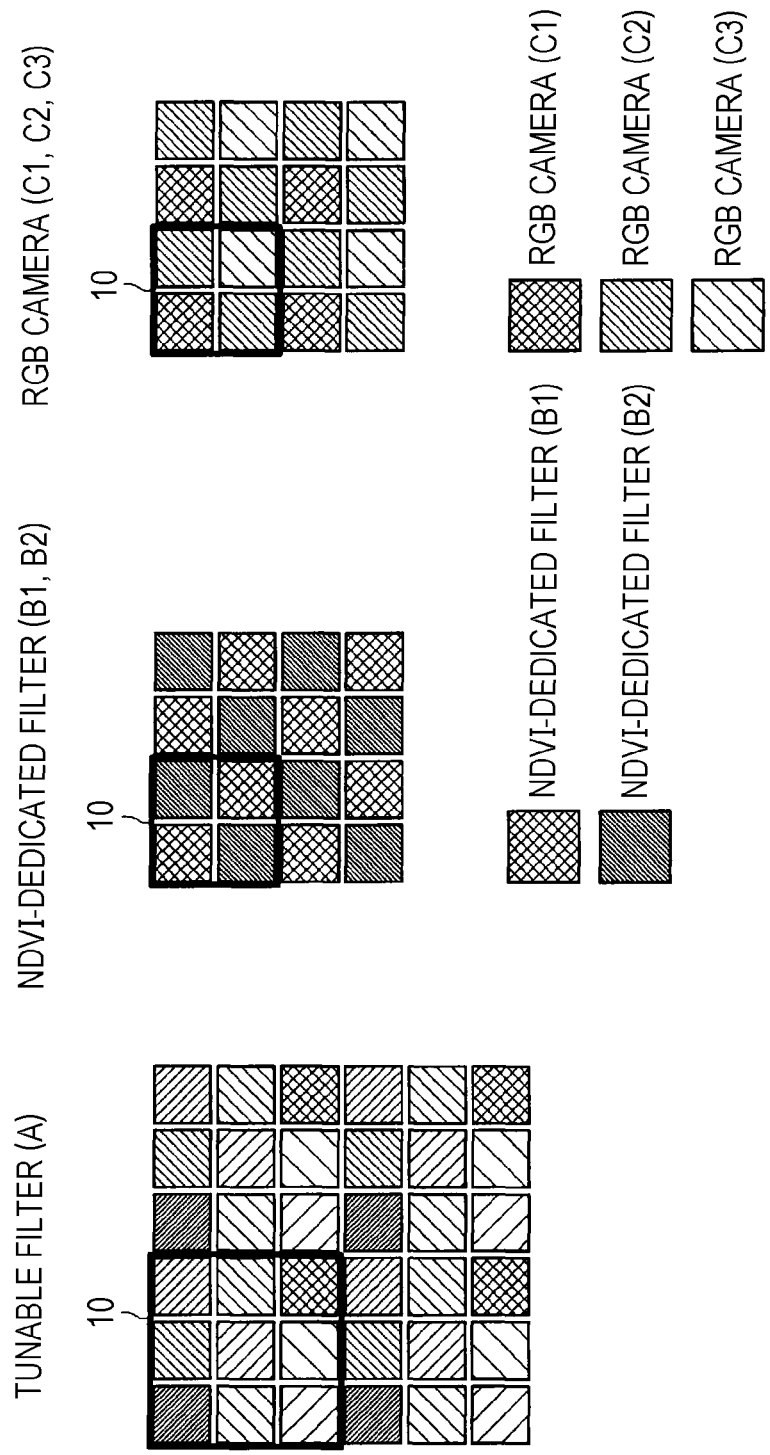
FIG. 27 is a diagram showing a configuration of a filter according to a sixth example.
Figure 28:
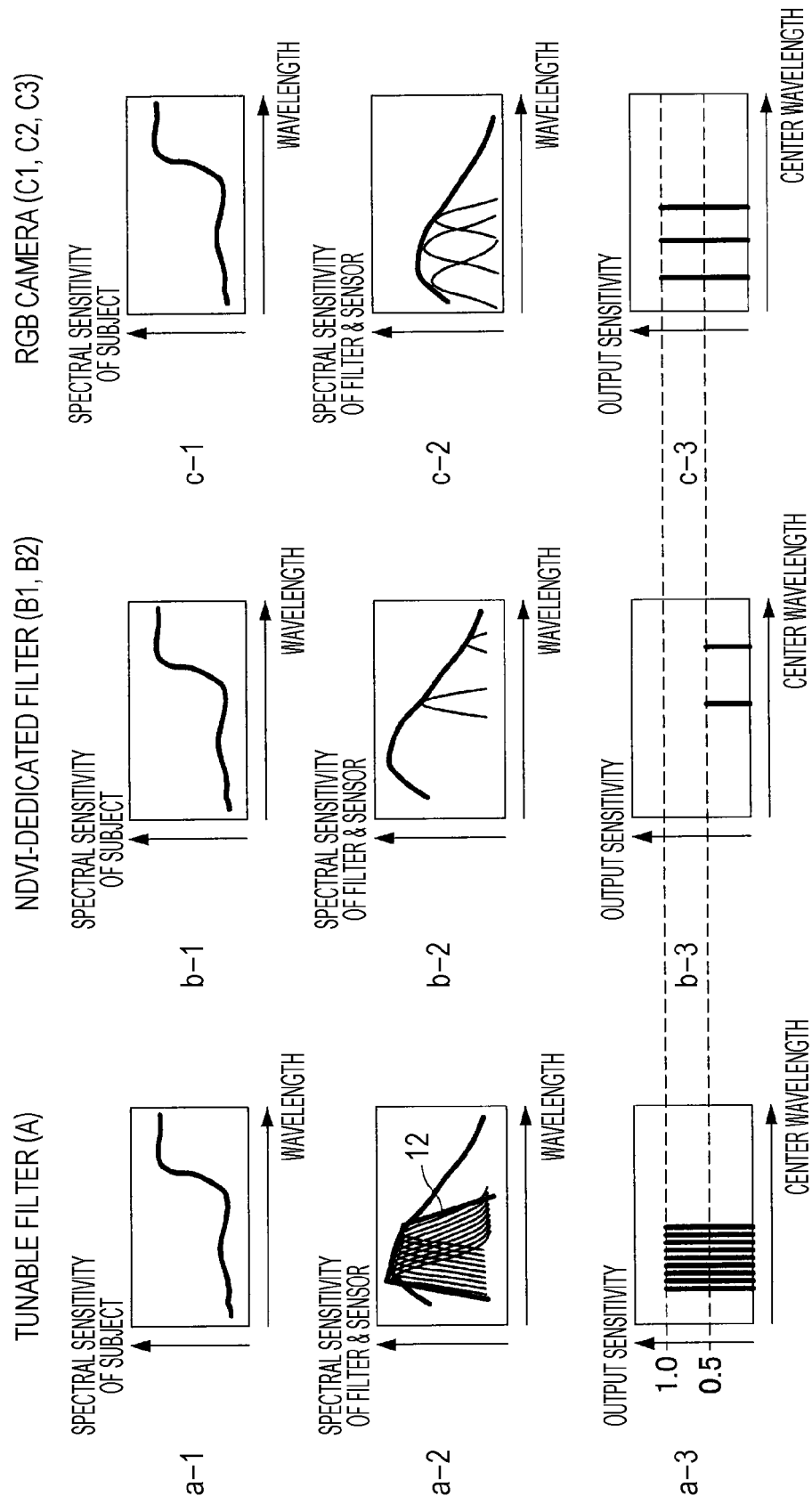
FIG. 28 is a diagram showing output sensitivities, etc. of pixels in the sixth example.
Figure 36:
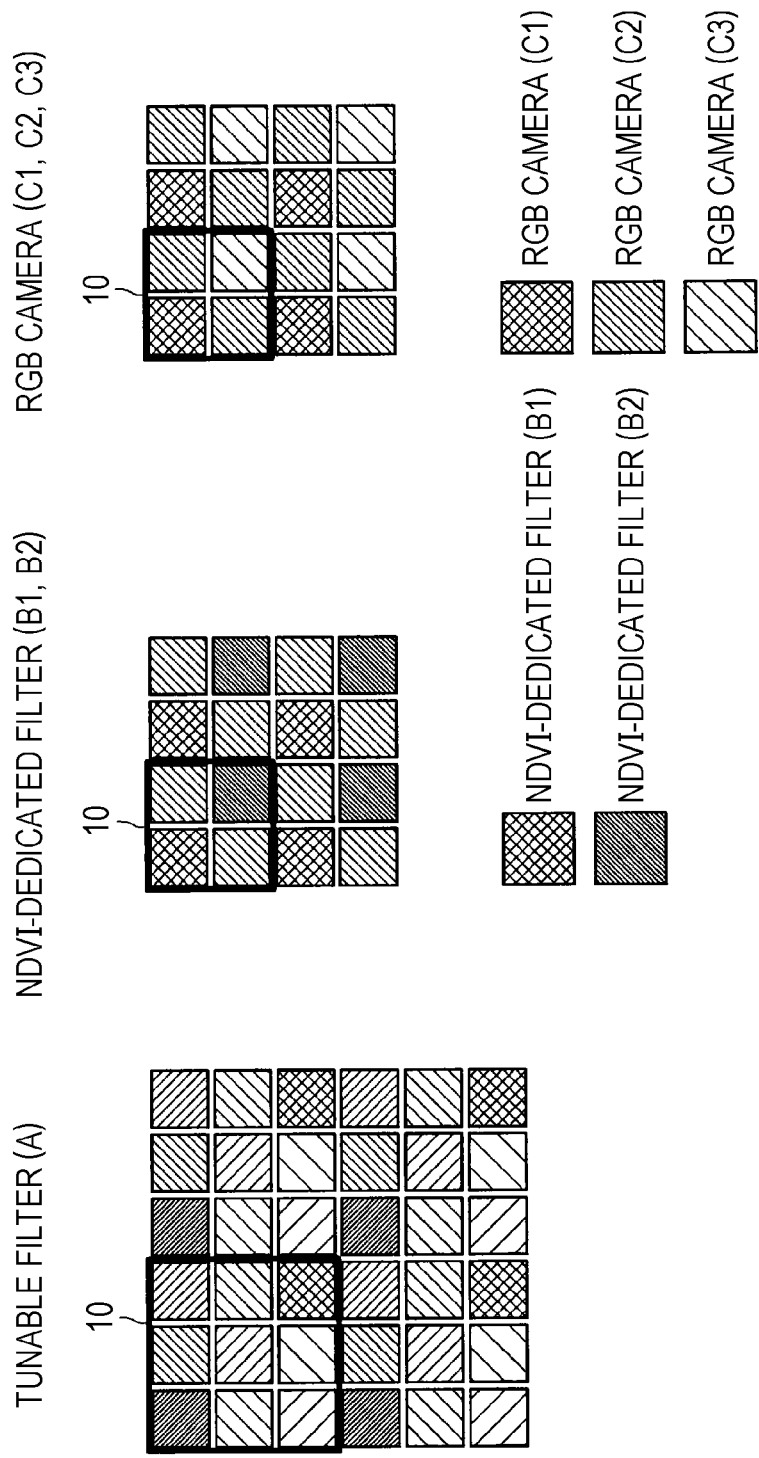
FIG. 36 is a diagram showing a configuration of a filter according to a ninth example.

Subsequently, a ninth example will be described. The present example shows a case in which the special purpose filter in the sixth example (FIG. 27) is achieved by an RGB sensor and a DBP. More specifically, the case where the NDVI-dedicated filters (B1, B2) are achieved by an RGB sensor and a DBP as shown in FIG. 36 is considered. In this case, regarding the NDVI-dedicated filters (B1, B2), pixels in a 2×2 array including one pixel having a filter for red light (RED), one pixel having a filter for NIR, and two pixels having filters for green light (GRN) are used as one pixel for sensing as shown in FIG. 36. In other words, in this example, the number of pixels of the wavelength band for red light (RED) and the number of pixels of the NIR wavelength band used for the calculation of NDVI are only a half of those in the sixth example (FIG. 27).

Figure 37:
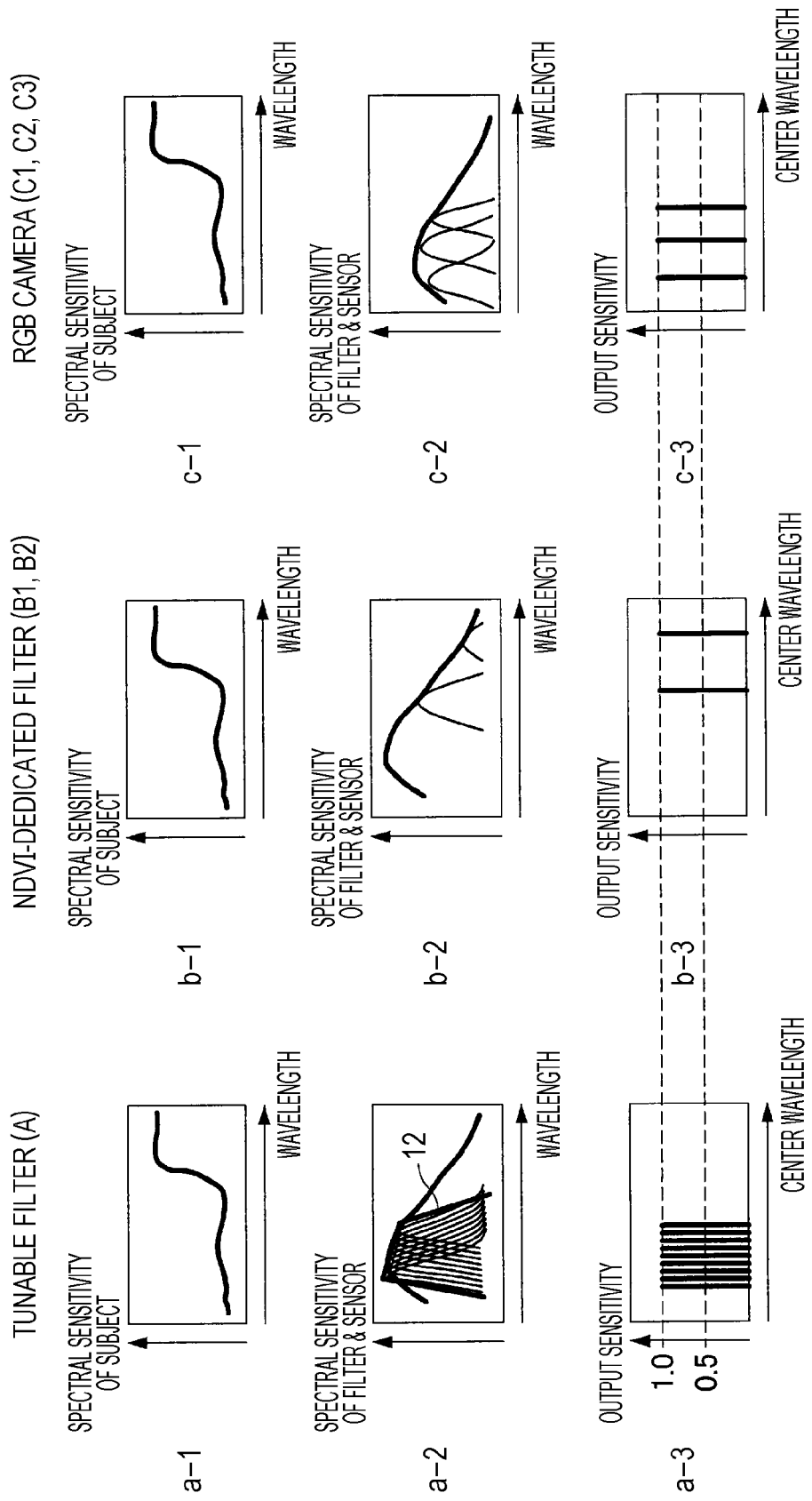
FIG. 37 is a diagram showing output sensitivities, etc. of pixels in the ninth example.
Figure 38:
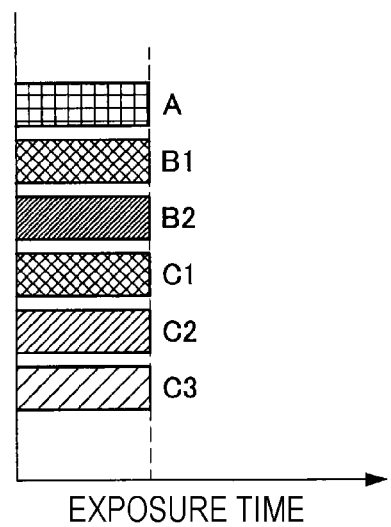
FIG. 38 is a diagram showing exposure times of filters in the ninth example.

Therefore, in the present example, the half bandwidth in the spectral characteristics of the NDVI-dedicated filters (B1, B2) and the image sensor 150 is set to be two times that in the sixth example (see b-2 in FIG. 28) as shown in b-2 in FIG. 37. Thus, on a pixel basis, the output sensitivity about two times the output sensitivity in the sixth example (as the overall NDVI-dedicated filter, the output sensitivity substantially equal to that in the sixth example) can be achieved as shown in b-3 of FIG. 37. Accordingly, the exposure control unit 130 sets the exposure times of the pixels having the tunable filters (A), the NDVI-dedicated filters (B1, B2), and the RGB cameras (C1, C2, C3) to be substantially the same as shown in FIG. 38. According to the present example, the image capture device 100 can improve the image quality or resolution of the output of the pixels having the tunable filters using the high-quality, high-resolution output of the pixels having the special purpose filters. Note that the output of the pixels having the tunable filters may be appropriately corrected using the output of the pixels having the special purpose filters.

Here, the reason why the half bandwidth of red light is greater than the half bandwidth of NIR in b-2 of FIG. 37 is because more red light is absorbed by plants than light of a NIS wavelength band. Since how much red light is absorbed is key information for the diagnosis of vegetation state, the fact that how much higher the output sensitivity for red light is set is the key point is desirably considered.

3.10. Tenth Example

As in the fourth example, the fifth example, the sixth example, and the seventh example described above, the present example considers a case in which the image capture device 100 includes multiple image capture mechanisms, and tunable filters and special purpose filters are arranged on different image sensors 150. In this case, the image capture device 100 may include a dichroic filter in the stage preceding the tunable filters and the special purpose filters to separate incident light into a plurality of light beams by the dichroic filter. With this configuration, the image capture device 100 can cause the separated incident light beams to enter the tunable filters and the special purpose filters, respectively, thereby being capable of acquiring an appropriate image without changing an optical axis.

Figure 39:
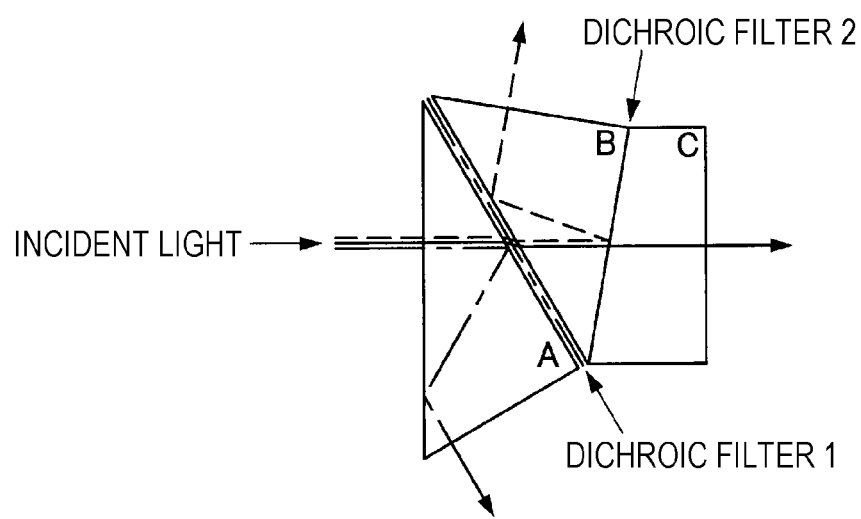
FIG. 39 is a diagram showing how a dichroic filter separates incident light into a plurality of beams in a tenth example.

First, an example of a case where a dichroic filter is applied to the fourth example will be described. As shown in FIG. 39, the image capture device 100 includes a dichroic filter 1 and a dichroic filter 2 in the stage preceding the tunable filter and the special purpose filter to separate the incident light into three light beams.

Figure 40:
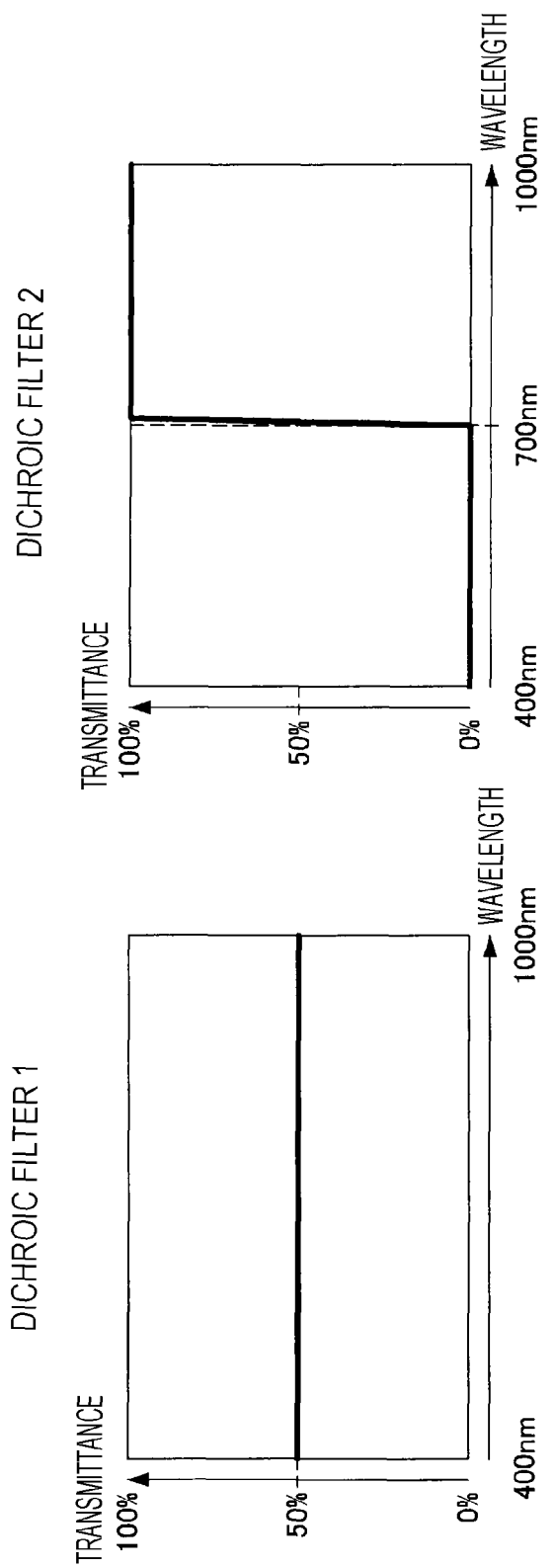
FIG. 40 is a diagram showing an example of a transmittance of a dichroic filter.
Figure 41:
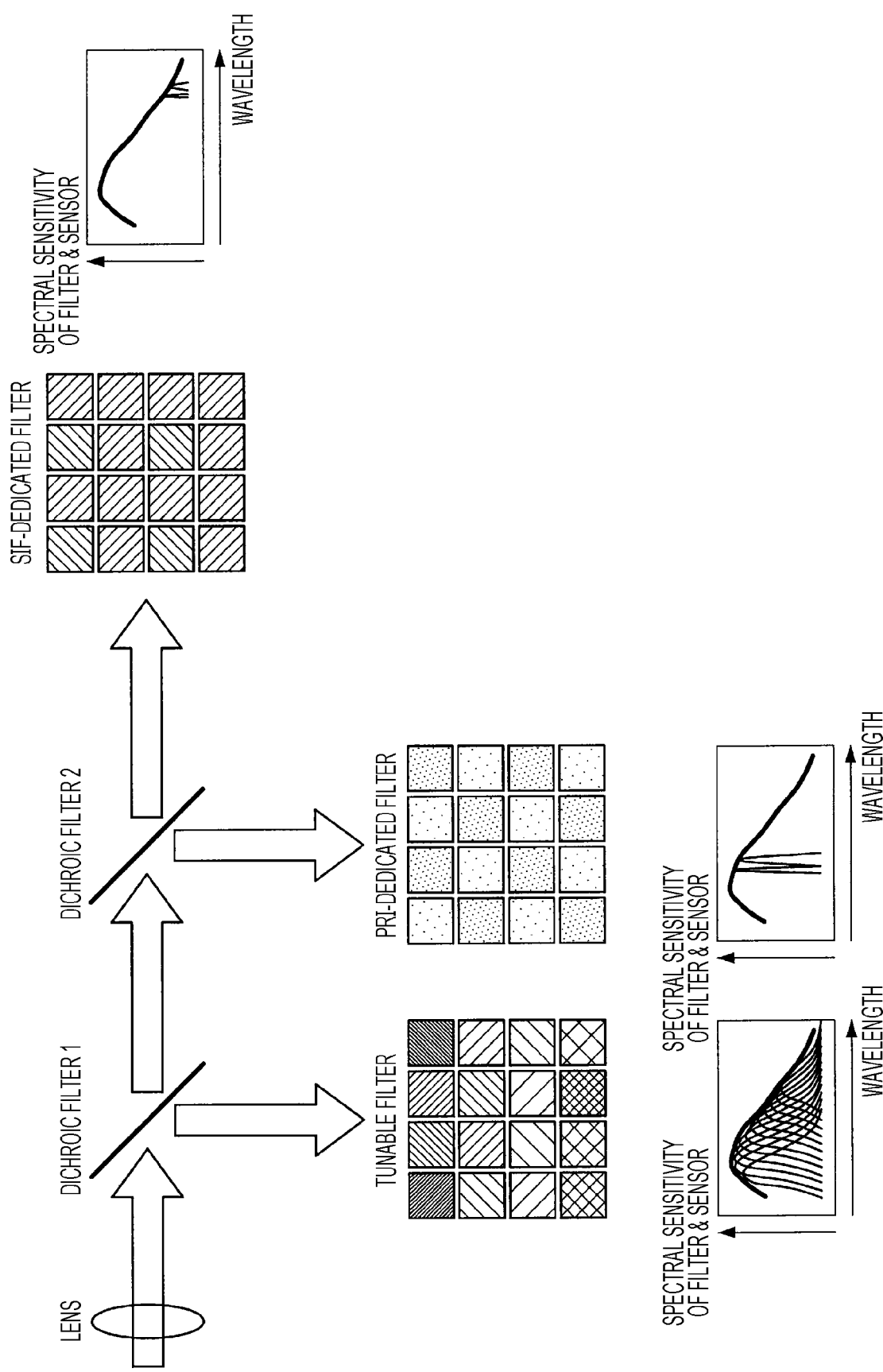
FIG. 41 is a diagram showing the arrangement of dichroic filters, tunable filters, and special purpose filters.

Here, as shown in FIG. 40, the dichroic filter 1 is assumed to have a transmittance of 50[%] and a reflectance of 50[%] over the entire region (400 to 1000 [nm] in this example). Further, the dichroic filter 2 is assumed to have a transmittance of 0[%] and a reflectance of 100[%] in 400 to 700 [nm], and a transmittance of 100[%] and a reflectance of 0[%] in 700 to 1000 [nm]. Then, as shown in FIG. 41, light reflected by the dichroic filter 1 enters the tunable filters, light reflected by the dichroic filter 2 enters the PRI-dedicated filters, and light transmitted through the dichroic filter 1 and the dichroic filter 2 enters the SIF-dedicated filters. In this case, 50[%] of the incident light enters the tunable filters, the PRI-dedicated filters, and the SIF-dedicated filters, so that the image capture device 100 can acquire an appropriate image from the pixels of the respective filters. More specifically, the image capture device 100 can acquire an image in which the optical axes match and the positions of the pixels match each other.

Next, an example of a case where a dichroic filter is applied to the fifth example will be described. The positional relationship between incident light and the dichroic filters 1 and 2 is similar to that in the example shown in FIG. 39.

Figure 42:
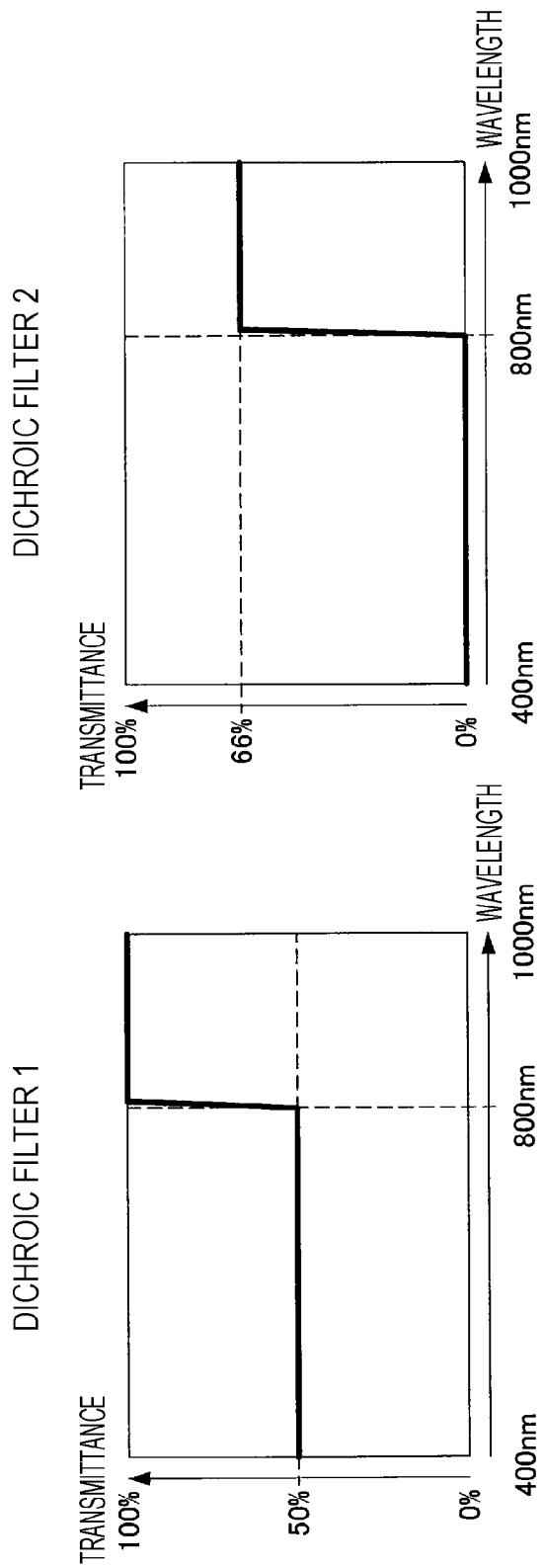
FIG. 42 is a diagram showing an example of a transmittance of a dichroic filter.
Figure 43:
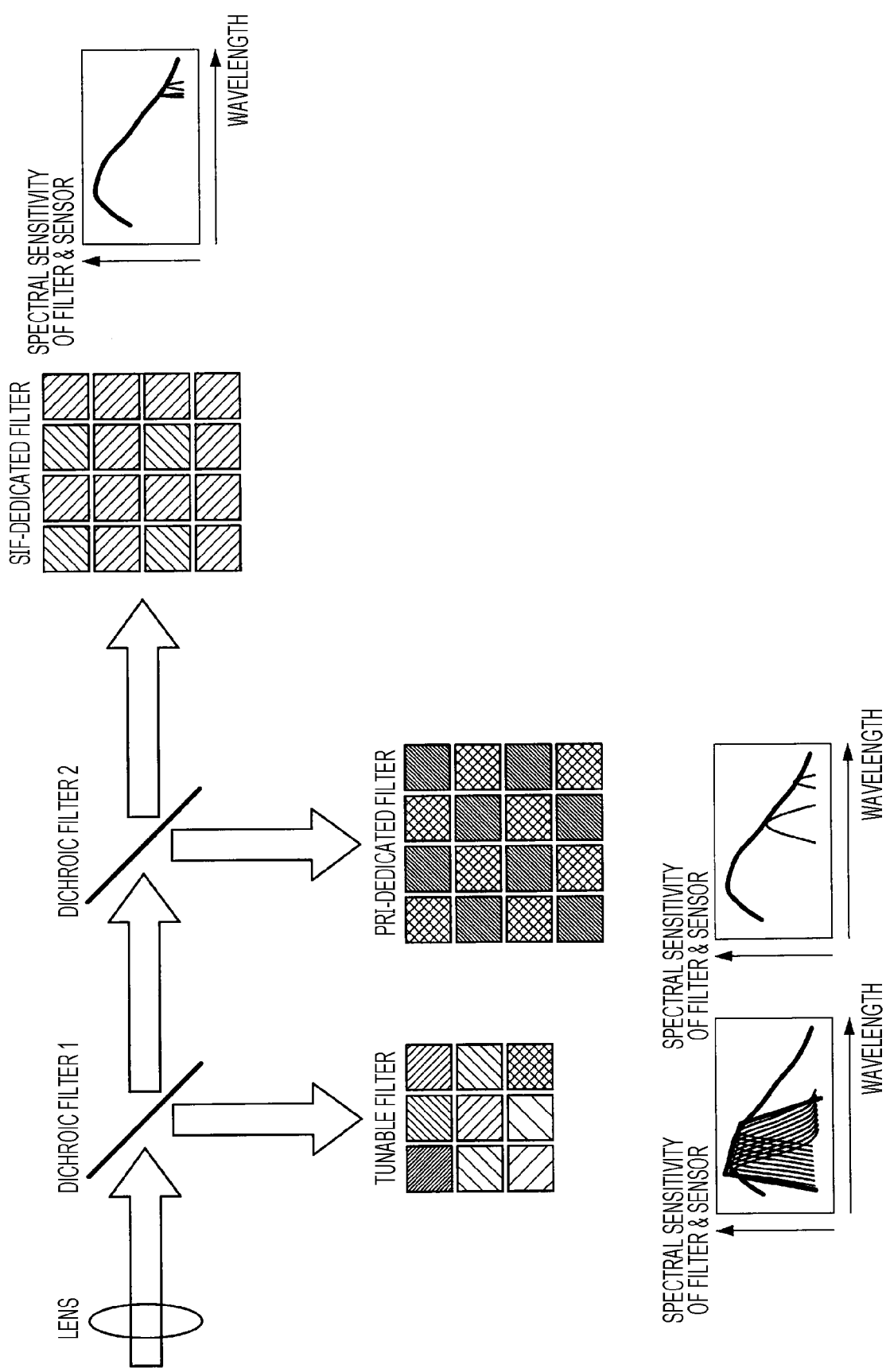
FIG. 43 is a diagram showing the arrangement of dichroic filters, tunable filters, and special purpose filters.

As shown in FIG. 42, the dichroic filter 1 is assumed to have a transmittance of 50[%] and a reflectance of 50[%] in 400 to 800 [nm], and a transmittance of 100[%] and a reflectance of 0[%] in 800 to 1000 [nm]. In addition, the dichroic filter 2 is assumed to have a transmittance of 0[%] and a reflectance of 100[%] in 400 to 800 [nm], and a transmittance of 66[%] and a reflectance of 33[%] in 800 to 1000 [nm]. Then, as shown in FIG. 43, light reflected by the dichroic filter 1 enters the tunable filters, light reflected by the dichroic filter 2 enters the NDVI-dedicated filters, and light transmitted through the dichroic filter 1 and the dichroic filter 2 enters the SIF-dedicated filters. In this case, 50[%] of incident light enters the tunable filters and the NDVI-dedicated filters (RED), 33[%] of incident light enters the NDVI-dedicated filters (NIR), and 66[%] of incident light enters the SIF-dedicated filters. This improves the balance of amounts of light incident on the respective filters, and thus the image capture device 100 can acquire a more appropriate image from the pixels of respective filters.

Next, an example of a case in which a dichroic filter is applied to the sixth example will be described. The positional relationship between incident light and the dichroic filters 1 and 2 is similar to that in the example shown in FIG. 39.

Figure 44:
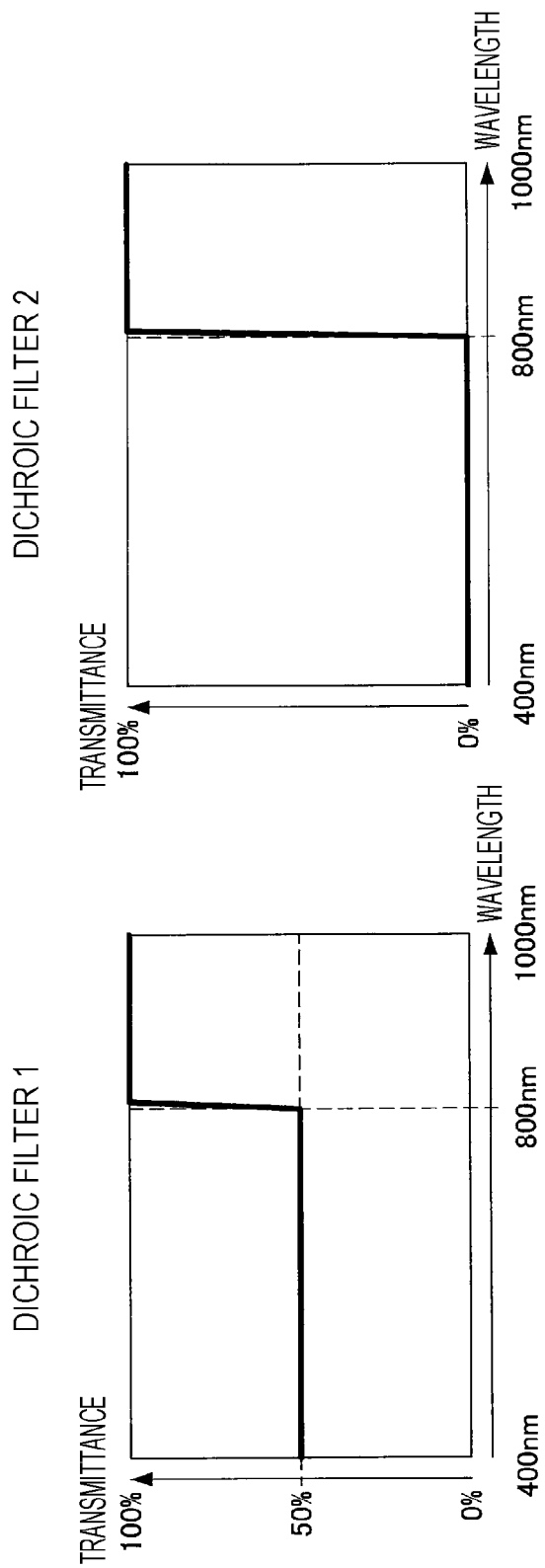
FIG. 44 is a diagram showing an example of a transmittance of a dichroic filter.
Figure 45:
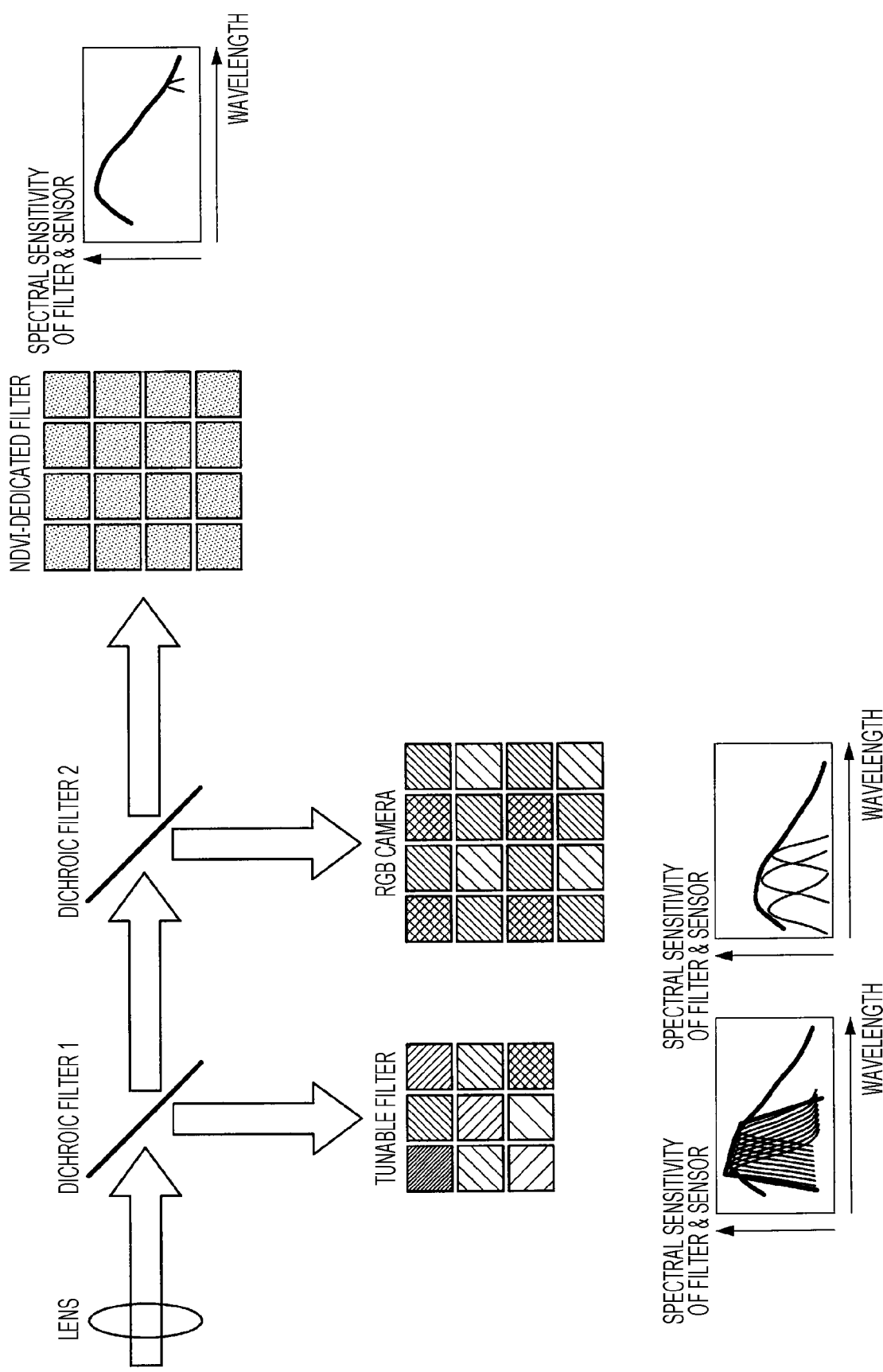
FIG. 45 is a diagram showing the arrangement of dichroic filters, tunable filters, and special purpose filters.

In this example, it is assumed that the NDVI-dedicated filter targets only NIR, and red light (RED) calculated from tunable filters or an RGB camera is used to calculate NDVI. As shown in FIG. 44, the dichroic filter 1 is assumed to have a transmittance of 50[%] and a reflectance of 50[%] in 400 to 800 [nm], and a transmittance of 100[%] and a reflectance of 0[%] in 800 to 1000 [nm]. In addition, the dichroic filter 2 is assumed to have a transmittance of 0[%] and a reflectance of 100[%] in 400 to 800 [nm], and a transmittance of 100[%] and a reflectance of 0[%] in 800 to 1000 [nm]. Then, as shown in FIG. 45, light reflected by the dichroic filter 1 enters the tunable filters, light reflected by the dichroic filter 2 enters the RGB cameras, and light transmitted through the dichroic filter 1 and the dichroic filter 2 enters the NDVI-dedicated filters (NIR). In this case, 50[%] of incident light enters the tunable filters and the RGB cameras, and 100[%] of incident light enters the NDVI-dedicated filters (NIR). This improves the balance of amounts of light incident on the respective filters, and thus the image capture device 100 can acquire an appropriate image from the pixels of respective filters.

Note that the abovementioned example described as the tenth example may be appropriately modified. For example, the transmittances of the dichroic filter 1 and the dichroic filter 2 in each wavelength band may be changed as appropriate.

4. Application Example

In the above, various examples to which the embodiment of the present disclosure has been applied have been described. Subsequently, an application example of the present disclosure will be described. The technology according to the present disclosure can be applied to various devices or systems. For example, the technology according to the present disclosure may be applied to a medical image capture device including a medical microscope, a medical endoscope, or the like, and a medical image capture system (a medical microscope system, a medical endoscope system, or the like) including these devices.

4.1. Example of Application to Medical Image Capture Device

Figure 46:
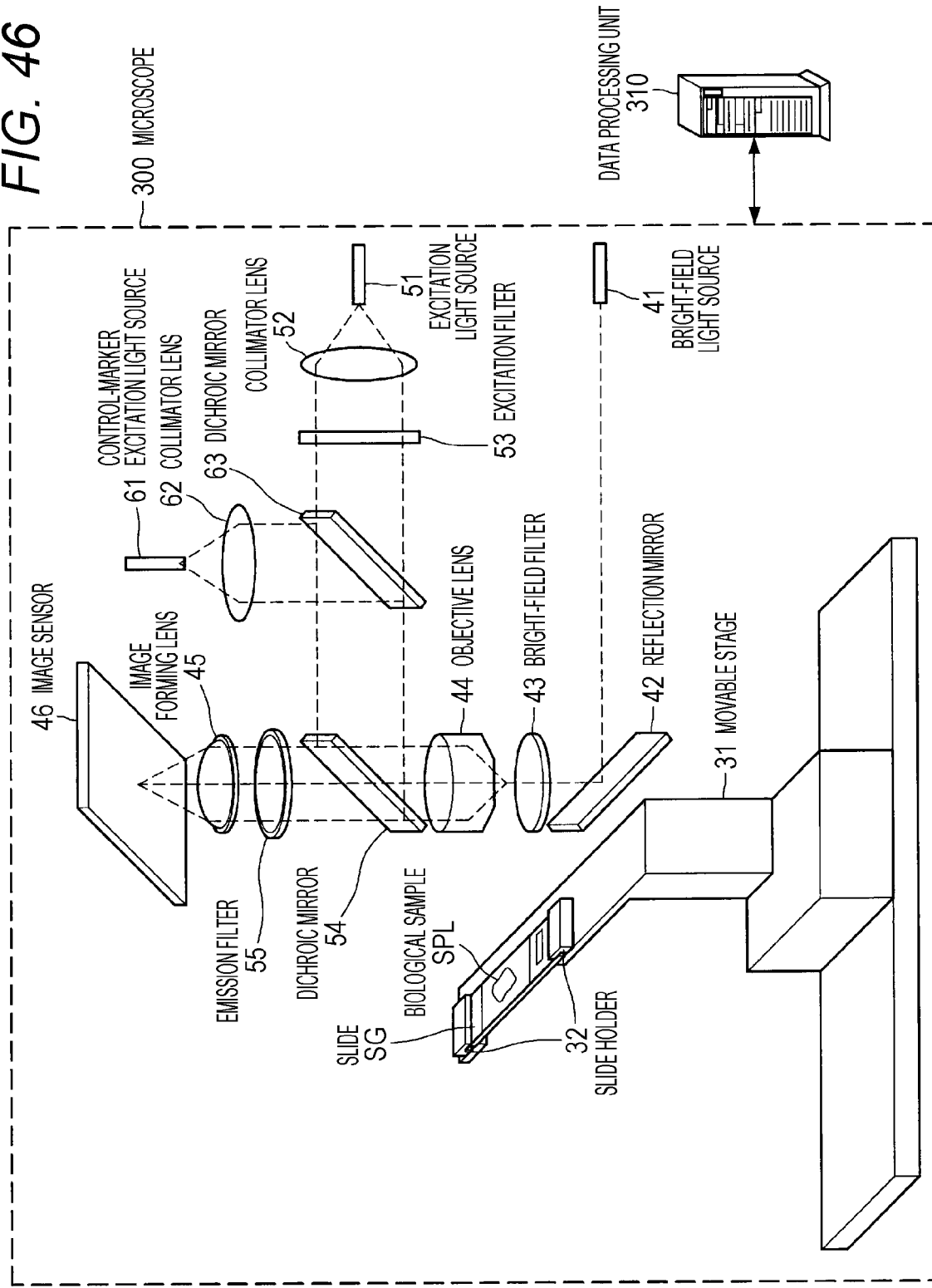
FIG. 46 is a diagram showing an example of a case where the technology according to the present disclosure is applied to a medical image capture device.

Here, an example of a case in which the technology according to the present disclosure is applied to a medical image capture device will be described with reference to FIG. 46. As shown in FIG. 46, a medical image capture device to which the present disclosure is applied includes a microscope 300 and a data processing unit 310.

The microscope 300 according to this application example has an image sensor 46, and a tunable filter and a special purpose filter which are provided in a stage preceding the image sensor 46 (in other words, in this application example, the image sensor 46 functions as a first detection unit that detects a signal of a first wavelength band and a second detection unit that detects a signal of a second wavelength band). Note that various arrangement modes described above can be applied to the arrangement of the tunable filter and the special purpose filter. Further, in a case where the microscope 300 includes a plurality of image capture mechanisms like a compound eye camera, the tunable filter and the special purpose filter may be arranged on different image sensors 46.

Further, the microscope 300 includes a plurality of types of light sources, and a bright field imaging mode and a dark field imaging mode can be switched by controlling these light sources. Here, the bright field imaging mode indicates a mode in which a biological sample SPL is irradiated with normal illumination light, by which a bright-field image (bright-field entire image or bright-field partial image) of the entire biological sample SPL or a part of the biological sample SPL can be acquired. On the other hand, the dark field imaging mode indicates a mode in which the biological sample SPL having a fluorescently stained part is irradiated with light that excites the stained part, by which a fluorescent image of a part of the biological sample SPL (hereinafter, referred to as a "dark-field partial image") can be obtained.

In the dark field imaging mode, the data processing unit 310 according to the present application example performs focusing using an output from the pixel on which the special purpose filter is arranged, and then, acquires a desired dark-field partial image using an output from the pixel on which the tunable filter is arranged (in other words, the data processing unit 310 functions as a focusing unit that performs focusing using a signal of a second wavelength band in the present application example).

Conventionally, the user replaces filters, or performs other processes in order to perform focusing using an image of a specific wavelength band, and therefore, it takes a considerable amount of time for focusing. On the other hand, in the present application example, the microscope 300 has the image sensor 46 provided with the tunable filter and the special purpose filter in the preceding stage of the image sensor 46 as described above, whereby the data processing unit 310 performs focusing and image capture after the focusing without a need to replace filters. Considering that, in a medical field, it may be required to acquire large amounts of pathological images or medical images in a short time, the present disclosure that enables focusing and image capture after the focusing in a shorter time is useful. Further, the output of the pixel on which the special purpose filter is arranged is superior to the output of the pixel on which the tunable filter is arranged in terms of resolution, accuracy, etc., and is thus more suitable for focusing. That is, the data processing unit 310 can achieve focusing with higher accuracy.

Further, the data processing unit 310 can extract an image of a desired wavelength band by performing, after focusing, the signal processing described above on the data output from the pixel on which the tunable filter is arranged. This improves convenience for the user. Hereinafter, the present application example including the configuration of the microscope 300 will be described in more detail.

(Details of Configuration, Etc. Of Microscope 300)

The microscope 300 has a stage (hereinafter referred to as a movable stage) 31 that is movable in directions (x-axis, y-axis, and z-axis directions) parallel to and perpendicular to a surface (hereinafter referred to as a slide placement surface) on which a slide SG such as a glass plate is placed. A slide holder 32 is provided on this slide placement surface.

In a case where the slide SG is set, the slide holder 32 is moved to a position designated as a setting place (hereinafter, also referred to as a slide setting position). At the slide setting position, the slide SG contained in a slide container (not shown) is removed and set in the slide holder 32 by a slide setting mechanism (not shown).

A tissue section or a secretion cell including a connective tissue such as blood, an epithelial tissue, or both of them, for example, is fixed to the slide SG contained in the slide container (not shown) as a biological sample SPL by a predetermined fixation technique, and stained, as necessary.

The staining includes not only typical staining techniques represented by a Hematoxylin-Eosin (HE) staining, a Giemsa staining, a Papanicolaou staining, or the like but also fluorescence staining techniques represented by a fluorescence in situ hybridization (FISH), an enzyme antibody technique, or the like.

In addition to a fluorescent label (also referred to below as a fluorescence marker) applied to a probe, the fluorescence staining technique generally uses another fluorescent label (also referred to below as a control marker) to be contrasted with the fluorescence marker on the probe.

The control marker has an excitation wavelength different from the excitation wavelength of the fluorescence marker. For example, the excitation wavelength is approximately 365 [nm], and 4', 6-diamidino-2-pheylindole (DAPI) is commonly used. With the DAPI, a target to be contrasted with the target of the fluorescence marker (also referred to below as a control target) is a cell nucleus.

In a case where an image of the biological sample SPL is captured, the slide holder 32 is moved to a position designated as a location for microscopic examination (hereinafter, also referred to as a microscopic examination position). In this case, the bright field imaging mode or the dark field imaging mode is executed.

In the bright field imaging mode, a bright-field light source 41 irradiates the biological sample SPL with illumination light. The illumination light is reflected by a reflection mirror 42, is emitted to the biological sample SPL in the microscopic examination position as a visible light through a bright-field filter 43, and then reaches an objective lens 44.

The power of the objective lens 44 is either as low as an image of the entire biological sample SPL (also referred to below as a bright-field entire image) can be formed or as high as an image of only a part of the biological sample SPL (also referred to below as a bright-field partial image) can be formed.

The microscope 300 forms an image of the biological sample SPL obtained through the illumination light on an imaging surface of the image sensor 46 as the bright-field entire image or the bright-field partial image after enlarging the image using the objective lens 44 and an image forming lens 45.

As described above, the microscope 300 is configured to obtain a bright-field image (bright-field entire image or bright-field partial image) of an entire or a part of the biological sample SPL in the bright field imaging mode.

Note that, in FIG. 46, a dichroic mirror 54 and an emission filter 55 are provided in an optical path between the objective lens 44 and the image forming lens 45. However, in the bright field imaging mode, the dichroic mirror 54 and the emission filter 55 are retracted to a position not in the optical path so that visible light entering from the bright-field filter 43 is not absorbed or reflected by these filters.

On the other hand, in the dark field imaging mode, an excitation light source 51 emits light (hereinafter, also referred to as excitation light) that excites both the fluorescence marker of the probe and the control marker. The power of the objective lens 44 when the excitation light is emitted is set to be high enough to form an image of a part of the biological sample SPL as a fluorescent image.

The excitation light emitted from the excitation light source 51 is collimated by a collimator lens 52, and light other than the excitation light is removed by an excitation filter 53. The excitation light transmitted through the excitation filter 53 is reflected by the dichroic mirror 54 and is condensed at the microscopic examination position by the objective lens 44.

When the probe is coupled to the target and the control target of the biological sample SPL in the microscopic examination position, the fluorescence marker applied to the probe and the control marker produce a luminescence by the excitation light. The luminescence is transmitted through the dichroic mirror 54 via the objective lens 44 and reaches the image forming lens 45 after light other than the luminescence of the fluorescent material is absorbed by the emission filter 55.

The microscope 300 enlarges an image obtained through the luminescence of the fluorescence marker and the control marker using the objective lens 44 and the image forming lens 45, and forms the enlarged image on the imaging surface of the image sensor 46 as the dark-field partial image.

As described above, the microscope 300 is configured to be able to acquire a fluorescent image of the sample part (dark-field partial image) in the dark field imaging mode.

Note that, although a dichroic mirror 63 is provided in the optical path between the excitation filter 53 and the dichroic mirror 54 in FIG. 46, the dichroic mirror 63 transmits the excitation light passing through the excitation filter 53.

In addition to the configuration described above, the microscope 300 includes a light source (also referred to below as a control-marker excitation light source) 61 configured to emit excitation light (also referred to below as control-marker exclusive excitation light) that excites the control marker while leaving the fluorescence marker unexcited.

The control-marker exclusive excitation light is emitted from the control-marker excitation light source 61 in a focusing process when the dark-field partial image of the biological sample SPL is obtained.

The control-marker exclusive excitation light emitted from the control-marker excitation light source 61 is collimated by a collimator lens 62, reflected by the dichroic mirror 63 and the dichroic mirror 54, and then focused on the microscopic examination position by the objective lens 44.

When the probe is coupled to the control target of the biological sample SPL in the microscopic examination position, the control marker applied to the probe produces a luminescence by the control-marker exclusive excitation light. The luminescence is transmitted through the dichroic mirror 54 via the objective lens 44 and reaches the image forming lens 45 after light other than the luminescence of the fluorescent material is absorbed by the emission filter 55.

The microscope 300 enlarges an image obtained through the luminescence of the control marker using the objective lens 44 and the image forming lens 45, and forms the enlarged image on the imaging surface of the image sensor 46 as the dark-field partial image.

The data processing unit 310 controls the movable stage 31 so that the corresponding sample part is focused using the dark-field partial image. Further, when the sample part is in focus, the data processing unit 310 causes the excitation light source 51 to emit the excitation light instead of the control-marker excitation light source 61, and stores the dark-field partial image obtained by the excitation light.

As described above, the medical image capture device is configured to acquire the dark-field partial image obtained by the control-marker exclusive excitation light as the dark-field partial image to be focused, and acquires the dark-field partial image obtained by the excitation light as the dark-field partial image to be stored.

(Processing Flow)

The details of the configuration, etc. of the microscope 300 have been described above. Next, an example of a flow of processing in the medical image capture device will be described with reference to FIG. 47.

In step S1200, the data processing unit 310 sets the slide holder 32 at the microscopic examination position, and sets the objective lens 44 with a high power in the optical axis between the dichroic mirror 54 and the image forming lens 45. The data processing unit 310 may set other components at predetermined positions.

In step S1204, the data processing unit 310 determines a sample part to be acquired of the biological sample SPL placed on the slide holder 32. The method for determining the sample part to be acquired is not particularly limited. For example, the sample part to be acquired may be determined on the basis of the designation from the user.

In step S1208, the data processing unit 310 drives the control-marker excitation light source 61 to acquire an output of the pixel having the special purpose filter in the image sensor 46. In step S1212, the data processing unit 310 focuses on the sample part to be acquired on the basis of the contrast of a part of the dark-field image (dark-field partial image) of the control marker in the sample part to be acquired.

In step S1216, the data processing unit 310 stops the driving of the control-marker excitation light source 61 and drives the excitation light source 51. In step S1220, the data processing unit 310 acquires the dark-field image of the fluorescence marker in the sample part to be acquired as a dark-field partial image to be recorded, and a series of processing ends.

Figure 47:
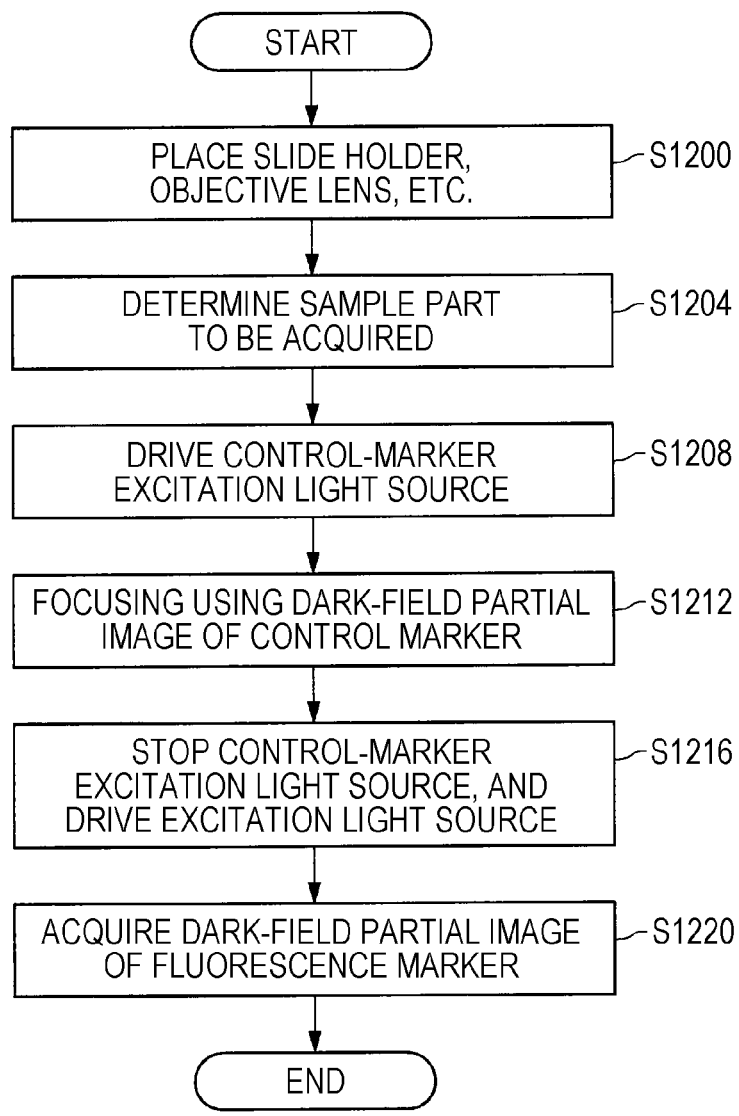
FIG. 47 is a flowchart showing an example of a flow of processing of the medical image capture device.

Note that the processes of steps in the flowchart shown in FIG. 47 are not necessarily performed in time series in the described order. That is, the processes of the respective steps in the flowchart may be performed in an order different from the described order, or may be performed in parallel.

An example of the case where the technology according to the present disclosure is applied to a medical image capture device has been described above, but devices or systems to which the technology according to the present disclosure is applied are not particularly limited. More specifically, the technology according to the present disclosure may be applied to any device other than the medical image capture device, and an output from a pixel having the special purpose filter arranged thereon may be used for a focusing process performed by the device.

4.2. Example of Application to Operating Room System

Next, an example of a case in which the technology according to the present disclosure is applied to an operating room system will be described.

Figure 48:
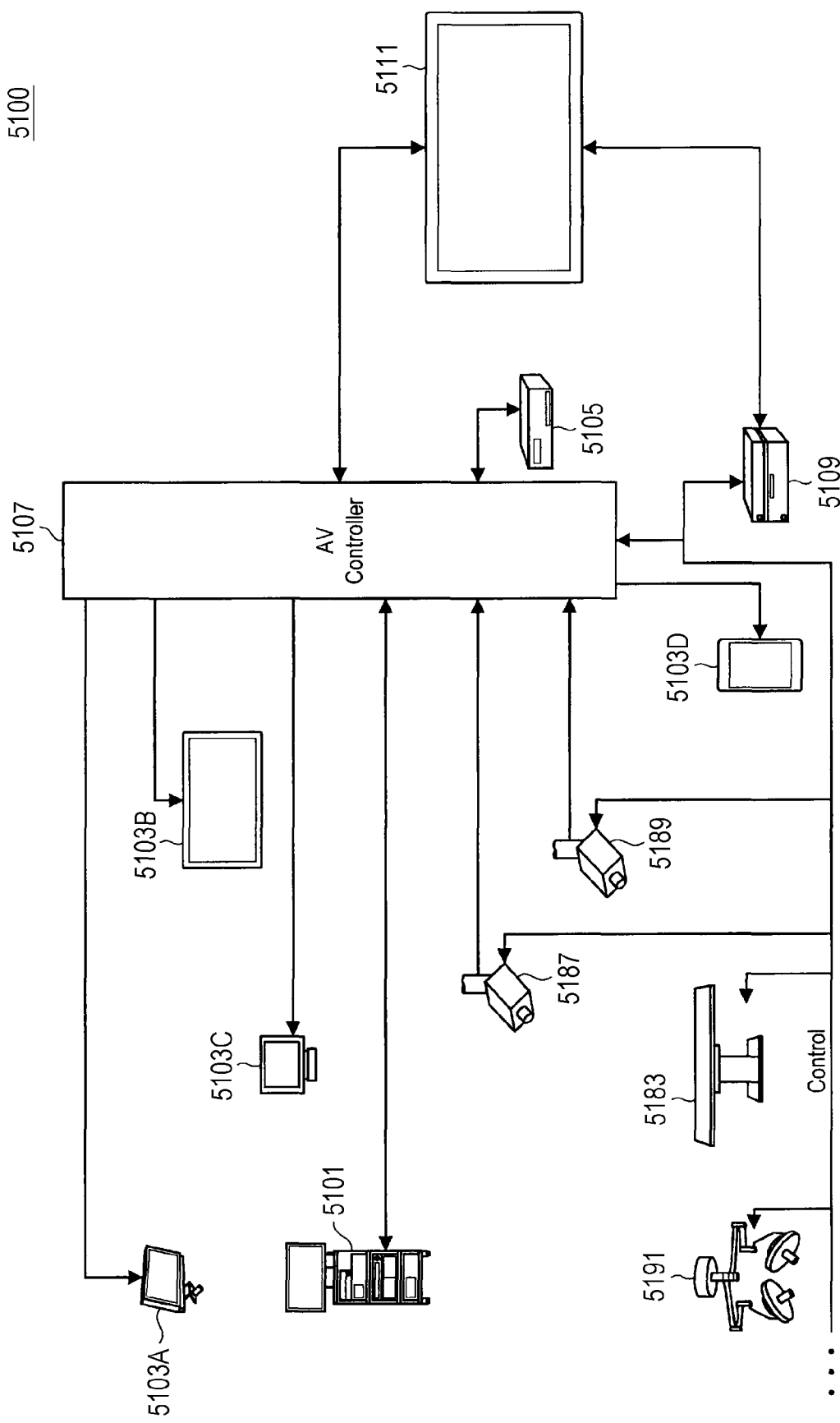
FIG. 48 is a diagram schematically showing an overall configuration of an operating room system.

FIG. 48 is a diagram schematically showing an overall configuration of an operating room system 5100 to which the technology according to the present disclosure can be applied. Referring to FIG. 48, the operating room system 5100 is configured by connecting a device group provided in an operating room so as to be able to cooperate with each other via an audio-visual controller (AV controller) 5107 and an operating room control device 5109.

Various devices may be provided in the operating room. FIG. 48 illustrates, as one example, a device group 5101 for endoscopic surgery, a ceiling camera 5187 that is provided on a ceiling of the operating room and captures an image of hands of an operator, an operating site camera 5189 that is provided on the ceiling of the operating room and captures an image of the entire operating room, a plurality of display devices 5103A to 5103D, a recorder 5105, a patient bed 5183, and an illumination 5191.

Here, among these devices, the device group 5101 belongs to an endoscopic surgical system 5113 as described later, and includes an endoscope, a display device that displays an image captured by the endoscope, and the like. Each device belonging to the endoscopic surgical system 5113 is referred to as a medical device. Meanwhile, the display devices 5103A to 5103D, the recorder 5105, the patient bed 5183, and the illumination 5191 are installed in, for example, the operating room, separately from the endoscopic surgical system 5113. Each device which does not belong to the endoscopic surgical system 5113 is referred to as a non-medical device. The AV controller 5107 and/or the operating room control device 5109 cooperatively control operations of the medical devices and the non-medical devices.

The AV controller 5107 comprehensively controls processing related to image display of the medical devices and the non-medical devices. Specifically, among the devices included in the operating room system 5100, the device group 5101, the ceiling camera 5187, and the operating site camera 5189 may be devices (referred to as source devices below) having a function for transmitting information to be displayed during surgery (referred to as display information below). Furthermore, the display devices 5103A to 5103D may be devices to which the display information is output (referred to as output destination devices below). Furthermore, the recorder 5105 may be a device corresponding to both the source device and the output destination device. The AV controller 5107 has a function for controlling operations of the source devices and the output destination devices, obtaining the display information from the source devices, transmitting the display information to the output destination devices, and allowing the output destination devices to display or record the display information. Note that the display information includes various images captured during the surgery, various kinds of information related to the surgery (for example, body information of patient, past examination results, information about surgery method, etc.), and the like.

Specifically, the device group 5101 may transmit information regarding an image of an operation site in body cavity of the patient captured by the endoscope to the AV controller 5107 as the display information. Further, the ceiling camera 5187 may transmit information regarding an image of the hands of the operator captured by the ceiling camera 5187 as the display information. Furthermore, the operating site camera 5189 may transmit information regarding an image indicating the state of the entire operating room captured by the operating site camera 5189 as the display information. Note that, in a case where the operating room system 5100 includes another device having an image capture function, the AV controller 5107 may obtain information regarding an image captured by the other device from the other device as the display information.

Alternatively, information regarding these images captured in the past is recorded in the recorder 5105 by the AV controller 5107, for example. The AV controller 5107 can obtain the information regarding the images captured in the past from the recorder 5105 as the display information. Note that various kinds of information regarding the surgery may be recorded in the recorder 5105 in advance.

The AV controller 5107 causes at least one of the display devices 5103A to 5103D that are output destination devices to display the obtained display information (in other words, images captured during surgery and various kinds of information regarding surgery). In the illustrated example, the display device 5103A is a display device provided as being suspended from the ceiling of the operating room, the display device 5103B is a display device provided on a wall of the operating room, the display device 5103C is a display device provided on a desk in the operating room, and the display device 5103D is a mobile device having a display function (for example, tablet personal computer (PC)).

Further, although not illustrated in FIG. 48, devices outside the operating room may be included in the operating room system 5100. The device outside the operating room may be, for example, a server connected to a network constructed inside and outside a hospital, a PC used by a medical staff, a projector provided in a conference room in the hospital, and the like. In a case where such an external device is provided outside the hospital, the AV controller 5107 can make a display device in another hospital display the display information via a television conference system and the like for remote medical treatment.

The operating room control device 5109 comprehensively controls processing other than the processing regarding the image display by the non-medical devices. For example, the operating room control device 5109 controls driving of the patient bed 5183, the ceiling camera 5187, the operating site camera 5189, and the illumination 5191.

A centralized operation panel 5111 is provided in the operating room system 5100, and the user can issue an instruction regarding image display to the AV controller 5107 via the centralized operation panel 5111 and issue an instruction regarding the operation of the non-medical device to the operating room control device 5109 via the centralized operation panel 5111. The centralized operation panel 5111 is configured by providing a touch panel on a display surface of the display device.

Figure 49:
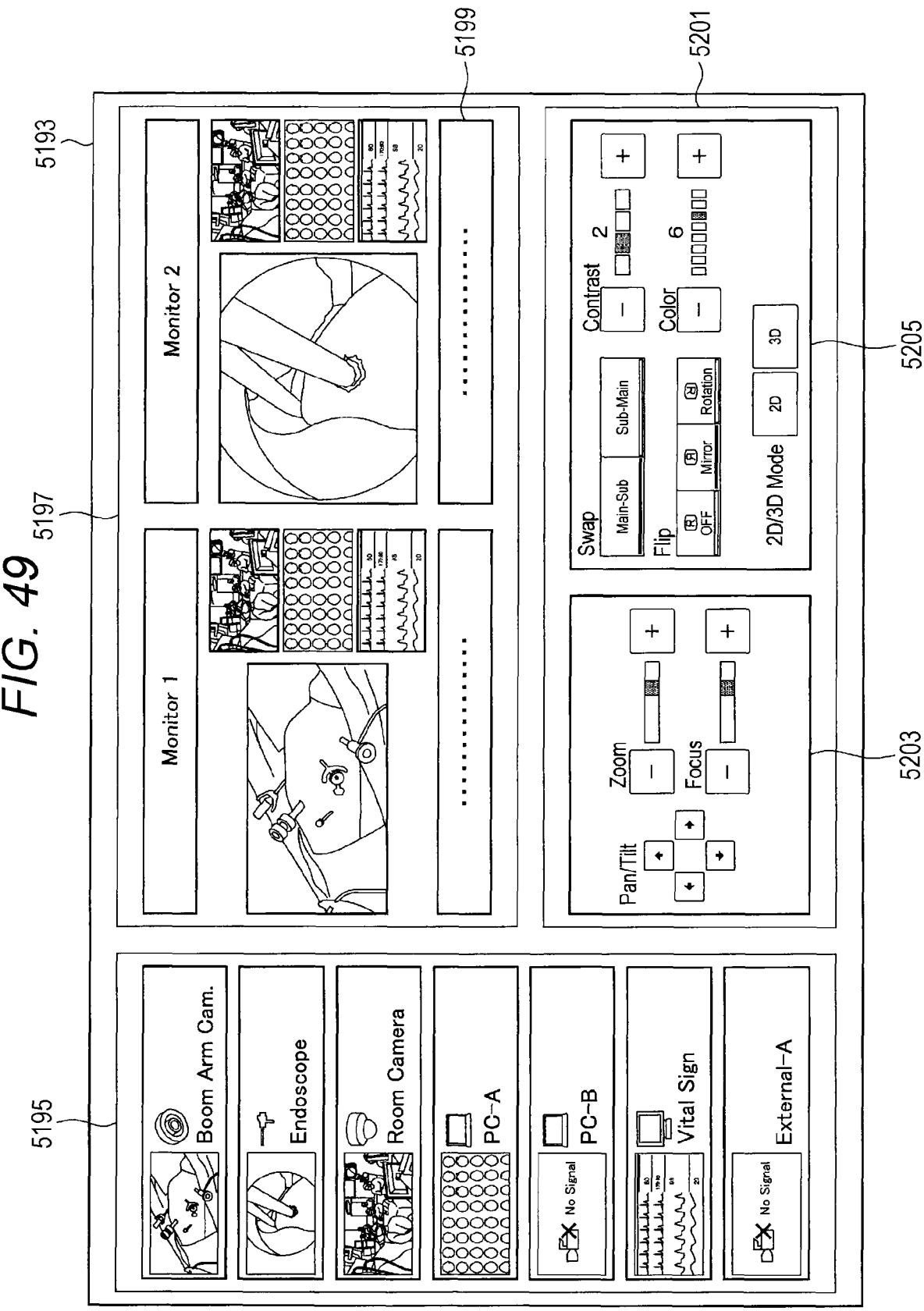
FIG. 49 is a diagram showing a display example of an operation screen on a centralized operation panel.

FIG. 49 is a diagram showing a display example of an operation screen on the centralized operation panel 5111. FIG. 49 illustrates an operation screen corresponding to a case where two display devices are provided in the operating room system 5100 as output destination devices as an example. Referring to FIG. 49, a source selection region 5195, a preview region 5197, and a control region 5201 are provided in an operation screen 5193.

In the source selection region 5195, a source device included in the operating room system 5100 and a thumbnail screen indicating display information of the source device are displayed in association with each other. The user can select the display information to be displayed on the display device from among the source devices displayed in the source selection region 5195.

In the preview region 5197, previews of screens of the two display devices (Monitor 1 and Monitor 2) that are output destination devices are displayed. In the illustrated example, four images are displayed in a single display device in a picture-in-picture (PinP) mode. The four images correspond to the display information transmitted from the source device selected in the source selection region 5195. One of the four images is displayed relatively large as a main image, and other three images are displayed relatively small as sub images. The user appropriately selects a region from among the regions where the four images are displayed to switch between the main image and the sub images. Furthermore, a status display region 5199 is provided in a lower portion of the region where the four images are displayed, and a status regarding surgery (for example, elapsed time of surgery, body information of patient, and the like) may be appropriately displayed in the region.

In the control region 5201, a source operation region 5203 where a graphical user interface (GUI) component used to perform an operation relative to the source device is displayed and an output destination operation region 5205 where a GUI component used to perform an operation relative to the output destination device is displayed are provided. In the illustrated example, in the source operation region 5203, GUI components used to perform various operations (panning, tilting, and zooming) relative to a camera of the source device having an image capture function are provided. The user appropriately selects the GUI component so as to operate the movement of the camera of the source device. Note that, although not illustrated, in a case where the source device selected in the source selection region 5195 is a recorder (in other words, image recorded in the recorder in the past is displayed in the preview region 5197), GUI components used to perform operations such as playing, stopping, rewinding, or fast-forwarding the image may be provided in the source operation region 5203.

Furthermore, in the output destination operation region 5205, GUI components used to perform various operations (swap, flip, color adjustment, contrast adjustment, and switching between 2D display and 3D display) regarding display on the display device which is the output destination device are provided. The user appropriately selects these GUI components so as to operate the display on the display device.

Note that the operation screen displayed on the centralized operation panel 5111 is not limited to the illustrated example. The user may be capable of inputting operations to each device, which is included in the operating room system 5100 and may be controlled by the AV controller 5107 and the operating room control device 5109, via the centralized operation panel 5111.

Figure 50:
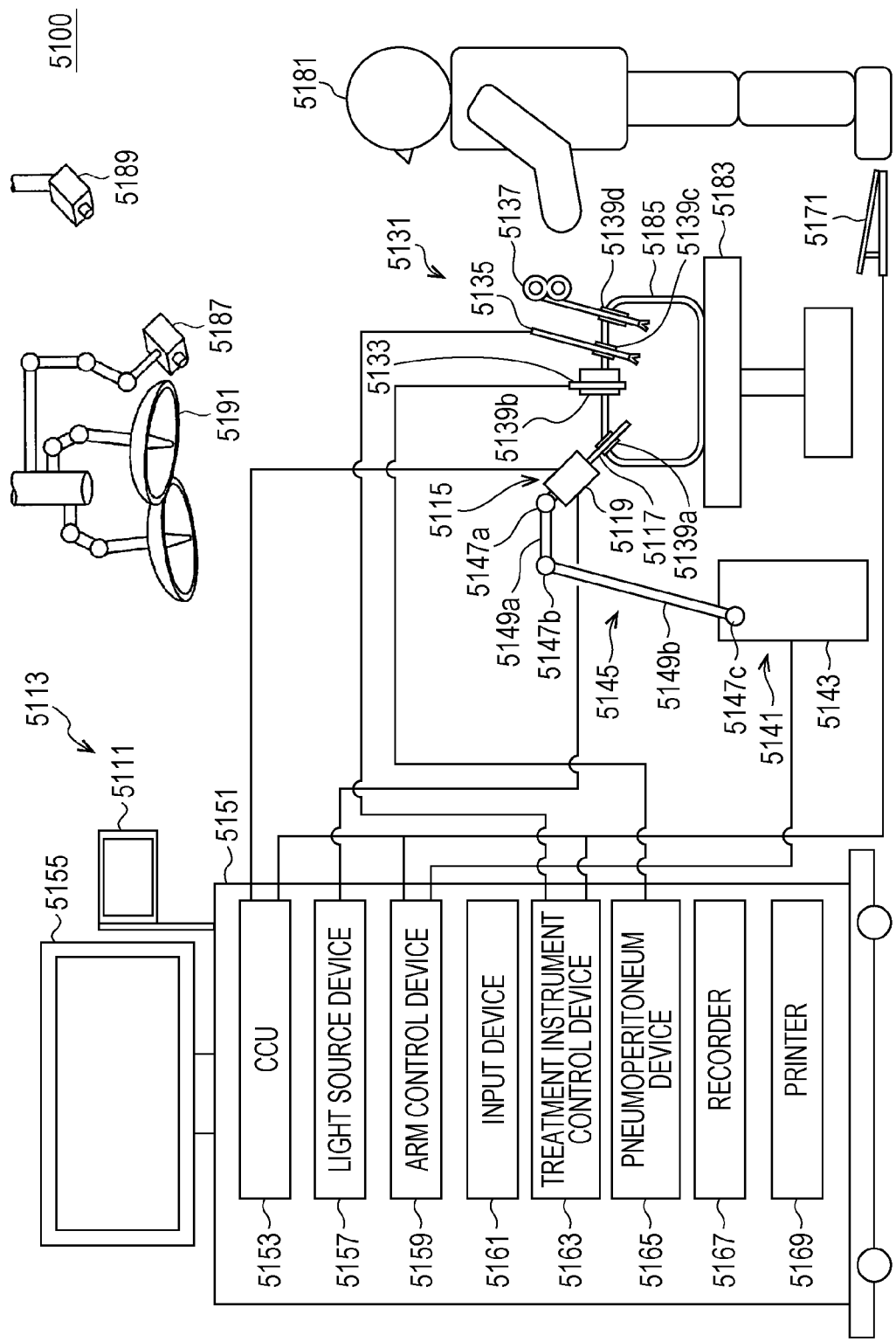
FIG. 50 is a diagram showing an example of a state of surgery to which the operating room system is applied.

FIG. 50 is a diagram showing an example of a state of surgery to which the operating room system described above is applied. The ceiling camera 5187 and the operating site camera 5189 are provided on the ceiling of the operating room and can capture an image indicating a state of the entire operating room, and an image of the hands of an operator (surgeon) 5181 who performs treatment on an affected part of a patient 5185 lying on the patient bed 5183. The ceiling camera 5187 and the operating site camera 5189 may have a magnification adjustment function, a focal distance adjustment function, an imaging direction adjustment function, and the like. The illumination 5191 is provided on the ceiling of the operating room and illuminates at least the hands of the operator 5181. The illumination 5191 may be capable of appropriately adjusting an amount of irradiation light, a wavelength (color) of irradiation light, an irradiation direction of light, and the like.

As illustrated in FIG. 48, the endoscopic surgical system 5113, the patient bed 5183, the ceiling camera 5187, the operating site camera 5189, and the illumination 5191 are mutually connected so as to cooperate with each other via the AV controller 5107 and the operating room control device 5109 (not illustrated in FIG. 50). In the operating room, the centralized operation panel 5111 is provided, and as described above, the user can appropriately operate these devices existing in the operating room via the centralized operation panel 5111.

The configuration of the endoscopic surgical system 5113 will be described below in detail. As illustrated in FIG. 50, the endoscopic surgical system 5113 includes an endoscope 5115, other surgical tools 5131, a supporting arm device 5141 for supporting the endoscope 5115, and a cart 5151 on which various devices for endoscopic surgery are mounted.

In endoscopic surgery, instead of cutting an abdominal wall and opening an abdomen, the abdominal wall is punctured by a plurality of cylindrical puncture devices referred to as trocars 5139*a* to 5139*d*. Then, through the trocars 5139*a* to 5139*d*, a lens barrel 5117 of the endoscope 5115 and the other surgical tools 5131 are inserted into the body cavity of the patient 5185. In the illustrated example, as the other surgical tools 5131, a pneumoperitoneum tube 5133, an energy treatment instrument 5135, and a forceps 5137 are inserted into the body cavity of the patient 5185. Furthermore, the energy treatment instrument 5135 is a treatment instrument which performs dissection and detachment of tissue, sealing of a blood vessel, or the like by high-frequency current or ultrasonic vibration. However, the illustrated surgical tools 5131 are merely exemplary, and it is allowable to use various surgical tools used for general endoscopic surgery, such as tweezers or a retractor, for example, as the surgical tools 5131.

An image of the operation site in the body cavity of the patient 5185 captured by the endoscope 5115 is displayed on a display device 5155. While viewing the image of the operation site displayed on the display device 5155 in real time, the operator 5181 executes processing, such as removing an affected part, by using the energy treatment instrument 5135 and the forceps 5137. Note that, although not illustrated, the pneumoperitoneum tube 5133, the energy treatment instrument 5135, and the forceps 5137 are supported by the operator 5181, an assistant, or the like, during surgery.

(Supporting Arm Device)

The supporting arm device 5141 includes an arm portion 5145 extending from a base portion 5143. In the illustrated example, the arm portion 5145 includes joint portions 5147a, 5147b, and 5147c and links 5149a and 5149b, and is driven by control of an arm control device 5159. The arm portion 5145 supports the endoscope 5115 and controls the position and the orientation of the endoscope 5115. Accordingly, the endoscope 5115 can be stably positioned.

(Endoscope)

The endoscope 5115 includes the lens barrel 5117 inserted into the body cavity of the patient 5185 by a predetermined length from a front end and a camera head 5119 connected to a base end of the lens barrel 5117. FIG. 50 shows an example in which the endoscope 5115 is a so-called rigid endoscope having a rigid lens barrel 5117. However, the endoscope 5115 may be a so-called flexible endoscope having a flexible lens barrel 5117.

An opening in which an objective lens is fitted is provided at the front end of the lens barrel 5117. A light source device 5157 is connected to the endoscope 5115, and light generated by the light source device 5157 is guided to the front end of the lens barrel by a light guide extending in the lens barrel 5117 and is emitted to an object to be observed in the body cavity of the patient 5185 through the objective lens. Note that the endoscope 5115 may be a forward-viewing endoscope, an oblique-viewing endoscope, or a side-viewing endoscope.

An optical system and an imaging element are provided in the camera head 5119, and light reflected by the object to be observed (observation light) is condensed on the imaging element by the optical system. The imaging element photoelectrically converts the observation light and generates an electric signal corresponding to the observation light, that is, an image signal corresponding to an observation image. The image signal is transmitted to a camera control unit (CCU) 5153 as raw data. Note that the camera head 5119 has a function for adjusting the magnification and the focal distance by appropriately driving the optical system of the camera head 5119.

Note that a plurality of imaging elements may be provided in the camera head 5119 in order to achieve, for example, stereoscopic viewing (3D display) or the like. In this case, a plurality of relay optical systems is provided in the lens barrel 5117 so as to guide the observation light to the plurality of imaging elements, respectively.

(Various Devices Mounted on Cart)

The CCU 5153 includes a central processing unit (CPU), a graphics processing unit (GPU), and the like, and comprehensively controls the operations of the endoscope 5115 and the display device 5155. Specifically, the CCU 5153 executes, on an image signal received from the camera head 5119, various image processing, such as development processing (demosaicing), to display an image based on the image signal. The CCU 5153 provides the image signal that has been subjected to the image processing to the display device 5155. In addition, the CCU 5153 is connected to the AV controller 5107 illustrated in FIG. 48. The CCU 5153 also provides the image signal that has been subjected to the image processing to the AV controller 5107. The CCU 5153 also transmits a control signal to the camera head 5119 to control driving of the camera head 5119. The control signal may include information regarding imaging conditions such as a magnification and a focal distance. The information regarding the imaging conditions may be input via an input device 5161 or may be input via the centralized operation panel 5111 described above.

The display device 5155 displays the image based on the image signal which has been subjected to the image processing by the CCU 5153 under the control of the CCU 5153. In a case where, for example, the endoscope 5115 is compatible with high resolution imaging such as 4K (3840 pixels (horizontal)×2160 pixels (vertical)) or 8K (7680 pixels (horizontal)×4320 pixels (vertical)), and/or in a case where the endoscope 5115 is compatible with 3D display, a display device which can achieve high resolution display and/or 3D display to be adapted to both cases may be used as the display device 5155. In a case where the display device 5155 is compatible with high resolution imaging such as 4K or 8K, more immersive feeling can be obtained by using a display device 5155 having a size equal to or larger than 55 inches. Furthermore, depending on the application, the plurality of display devices 5155 having different resolutions and different sizes may be provided.

The light source device 5157 includes a light source such as a light emitting diode (LED), for example, and supplies irradiation light for imaging an operation site to the endoscope 5115.

The arm control device 5159 includes, for example, a processor such as a CPU, and operates according to a predetermined program so as to control driving of the arm portion 5145 of the supporting arm device 5141 according to a predetermined control method.

The input device 5161 may be an input interface for the endoscopic surgical system 5113. The user can input various kinds of information and instructions to the endoscopic surgical system 5113 via the input device 5161. For example, the user inputs various kinds of information regarding the surgery, such as body information of the patient, and an operative method, via the input device 5161. Furthermore, for example, the user inputs an instruction to drive the arm portion 5145, an instruction to change the imaging conditions (kind of irradiation light, magnification, focal distance, and the like) by the endoscope 5115, an instruction to drive the energy treatment instrument 5135, and the like via the input device 5161.

The type of the input device 5161 is not limited, and various known input devices may be used as the input device 5161. As the input device 5161, a component such as a mouse, a keyboard, a touch panel, a switch, a foot switch 5171, and/or a lever may be applied, for example. In a case where a touch panel is used as the input device 5161, the touch panel may be provided on the display surface of the display device 5155.

Alternatively, the input device 5161 is a device worn by the user, for example, a glasses-type wearable device, a head mounted display (HMD), and the like, and various inputs are performed according to a gesture and a line-of-sight of the user detected by these devices. Furthermore, the input device 5161 includes a camera which can detect a motion of the user, and various inputs are performed according to the gesture and the line-of-sight of the user detected from an image captured by the camera. In addition, the input device 5161 includes a microphone which can collect voice of the user, and various inputs are performed by using voice via the microphone. In this way, the input device 5161 is configured to be capable of inputting various kinds of information in a non-contact manner so that the user (for example, operator 5181) belonging to an especially clean area can operate devices belonging to an unclean area in a non-contact manner. Furthermore, since the user can operate the device without releasing his/her hand from the surgical tools he/she uses, convenience of the user is improved.

A treatment instrument controlling device 5163 controls driving of the energy treatment instrument 5135 for cauterizing or dissecting tissue or sealing a blood vessel, for example. To secure a field of view and an operation space of an operator by the endoscope 5115, a pneumoperitoneum device 5165 injects gas into the body cavity through the pneumoperitoneum tube 5133 to swell the body cavity of the patient 5185. A recorder 5167 is a device capable of recording various kinds of information regarding surgery. A printer 5169 is a device capable of printing various kinds of information regarding surgery in various formats such as a text, an image, or a graph.

A particularly characteristic configuration of the endoscopic surgical system 5113 will be described below in more detail.

(Supporting Arm Device)

The supporting arm device 5141 includes the base portion 5143 that is a base, and the arm portion 5145 extending from the base portion 5143. In the illustrated example, the arm portion 5145 includes a plurality of joint portions 5147*a*, 5147*b*, and 5147*c* and a plurality of links 5149*a* and 5149*b* coupled by the joint portion 5147*b*. However, for easy understanding, the configuration of the arm portion 5145 is simplified in FIG. 50. Actually, shapes, the number, and arrangement of the joint portions 5147*a* to 5147*c* and the links 5149*a* and 5149*b*, directions of rotation axes of the joint portions 5147*a* to 5147*c*, and the like may be appropriately set so that the arm portion 5145 has a desired degree of freedom. For example, the arm portion 5145 may preferably have degrees of freedom equal to or more than six degrees of freedom. With this configuration, the endoscope 5115 can be freely moved in a possible movement range of the arm portion 5145, whereby the lens barrel 5117 of the endoscope 5115 can be inserted into the body cavity of the patient 5185 in a desired direction.

Actuators are provided in the joint portions 5147*a* to 5147*c*, and the joint portions 5147*a* to 5147*c* can rotate around a predetermined rotation axis by driving of the actuators. The driving of the actuators is controlled by the arm control device 5159, whereby a rotation angle of each of the joint portions 5147*a* to 5147*c* is controlled, and the driving of the arm portion 5145 is controlled. With this operation, the position and the orientation of the endoscope 5115 can be controlled. At this time, the arm control device 5159 can control the driving of the arm portion 5145 by various known control methods such as force control or position control.

For example, the operator 5181 appropriately performs an operation input via the input device 5161 (including foot switch 5171) so as to appropriately control the driving of the arm portion 5145 by the arm control device 5159 according to the operation input, and the position and the orientation of the endoscope 5115 may be controlled. With this control, after the endoscope 5115 provided at the front end of the arm portion 5145 is moved from a certain position to a certain position, the endoscope 5115 can be fixedly supported at the position after being moved. Note that the arm portion 5145 may be operated by a so-called master-slave method. In this case, the arm portion 5145 may be remotely controlled by the user via the input device 5161 provided at a place away from the operating room.

Furthermore, in a case where the force control is applied, the arm control device 5159 may perform so-called power assist control of receiving external force from the user and driving the actuator of each of the joint portions 5147*a* to 5147*c* so as to smoothly move the arm portion 5145 according to the external force. With this control, when the user moves the arm portion 5145 while directly having contact with the arm portion 5145, the arm portion 5145 can be moved with relatively weak force. Therefore, the endoscope 5115 can be more intuitively moved by a simpler operation, and thus, the convenience of the user can be improved.

Here, in general, a doctor called an endoscopist holds the endoscope 5115 in the endoscopic surgery. On the other hand, when the supporting arm device 5141 is used, the position of the endoscope 5115 can be more reliably fixed without manual operations. Therefore, the image of the operation site can be stably obtained, and surgery can be smoothly performed.

Note that the arm control device 5159 is not necessarily provided on the cart 5151. Furthermore, the arm control device 5159 is not necessarily a single device. For example, the arm control device 5159 may be provided in each of the joint portions 5147*a* to 5147*c* of the arm portion 5145 of the supporting arm device 5141, and the driving of the arm portion 5145 may be controlled by the plurality of arm control devices 5159 that performs in cooperation with each other.

(Light Source Device)

The light source device 5157 supplies irradiation light used for imaging the operation site to the endoscope 5115. The light source device 5157 includes, for example, an LED, a laser light source, or a white light source including a combination of the LED and the laser light source. In this configuration, in a case where the white light source includes a combination of RGB laser light sources, an output intensity and an output timing of each color (each wavelength) can be controlled with high accuracy, whereby the light source device 5157 can adjust a white balance of the captured image. Furthermore, in this case, images respectively corresponding to the R, G, and B can also be captured in time division by irradiating the object to be observed with laser light from each of the RGB laser light sources in time division, and controlling the driving of the imaging element of the camera head 5119 in synchronization with the irradiation timing. According to this method, a color image can be obtained without providing a color filter in the imaging element.

Furthermore, the driving of the light source device 5157 may be controlled so as to change the intensity of output light for each predetermined time period. The driving of the imaging element of the camera head 5119 is controlled in synchronization with a timing of changing the light intensity to obtain the images in time division, and the obtained images are synthesized, whereby an image with a high dynamic range that does not have so-called blocked up shadows and blown-out highlights can be generated.

Furthermore, the light source device 5157 may be formed to be capable of supplying light in a predetermined wavelength band compatible with special light observation. In the special light observation, for example, light in a narrower band than irradiation light (in other words, white light) at the time of normal observation is emitted using wavelength dependency of a body tissue to absorb light, whereby so-called narrow band imaging is performed in which a predetermined tissue such as a blood vessel in a mucosal surface layer is imaged with high contrast. Alternatively, in the special light observation, fluorescence observation for obtaining an image with fluorescence generated by irradiation with excitation light may be performed. In the fluorescence observation, the body tissue may be irradiated with excitation light, and the fluorescence from the body tissue may be observed (self-fluorescence observation), for example. Alternatively, a reagent such as indocyanine green (ICG) may be injected in the body tissue, and the body tissue may be irradiated with excitation light corresponding to the fluorescence wavelength of the reagent, to thereby obtain a fluorescent image, for example. The light source device 5157 can supply narrow band light and/or excitation light compatible with such special light observation.

(Camera Head and CCU)

Figure 51:
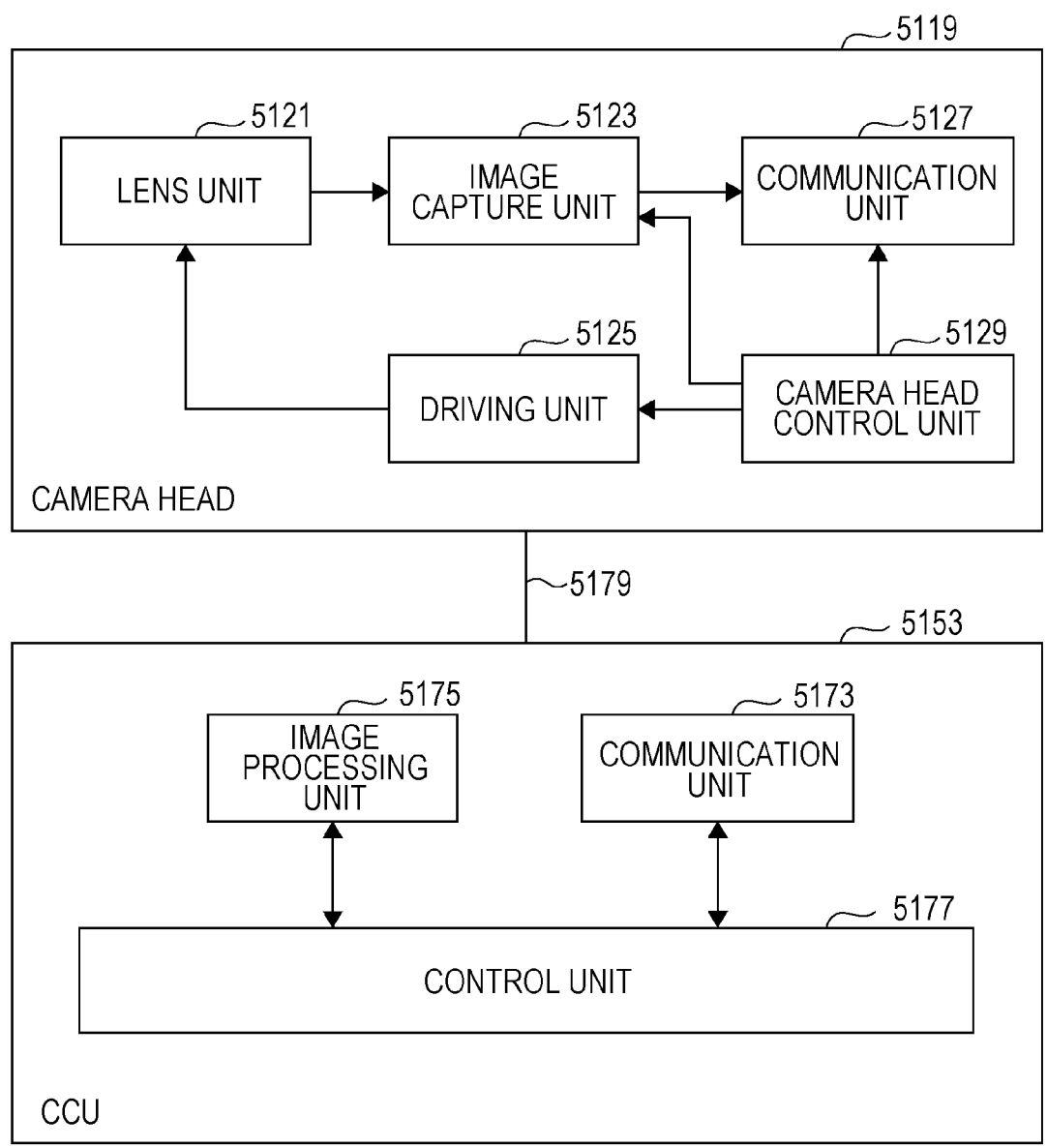
FIG. 51 is a block diagram showing an example of a functional configuration of a camera head and a CCU shown in FIG. 50.

Referring to FIG. 51, functions of the camera head 5119 and the CCU 5153 of the endoscope 5115 will be described in more detail. FIG. 51 is a block diagram showing an example of a functional configuration of the camera head 5119 and the CCU 5153 shown in FIG. 50.

Referring to FIG. 51, the camera head 5119 includes a lens unit 5121, an image capture unit 5123, a driving unit 5125, a communication unit 5127, and a camera head control unit 5129 as functions of the camera head 5119. Further, the CCU 5153 includes a communication unit 5173, an image processing unit 5175, and a control unit 5177 as functions of the CCU 5153. The camera head 5119 and the CCU 5153 are communicably and bidirectionally connected to each other by a transmission cable 5179.

First, the functional configuration of the camera head 5119 will be described. The lens unit 5121 is an optical system provided at a connecting portion with the lens barrel 5117. Observation light taken from the front end of the lens barrel 5117 is guided to the camera head 5119 and enters the lens unit 5121. The lens unit 5121 is formed by combining a plurality of lenses including a zoom lens and a focus lens. Optical characteristics of the lens unit 5121 are adjusted to collect the observation light on a light receiving surface of the imaging element of the image capture unit 5123. Furthermore, the zoom lens and the focus lens are movable so that the positions thereof on the optical axis can be moved to adjust a magnification and a focus of a captured image.

The image capture unit 5123 includes the imaging element and is arranged in the stage following the lens unit 5121. The observation light which has passed through the lens unit 5121 is condensed on the light receiving surface of the imaging element, and an image signal corresponding to an observation image is generated by photoelectric conversion. The image signal generated by the image capture unit 5123 is provided to the communication unit 5127.

The imaging element constituting the image capture unit 5123 is, for example, a complementary metal oxide semiconductor (CMOS) image sensor which has a Bayer array and can perform color imaging. Note that, as the imaging element, an imaging element that can be adapted to capture, for example, an image with a high resolution equal to or higher than 4K may be used. Since the image of the operation site can be obtained with high resolution, the operator 5181 can recognize the state of the operation site in more detail, and can smoothly proceed with the surgery.

Furthermore, the imaging element constituting the image capture unit 5123 includes a pair of imaging elements for respectively obtaining image signals for right and left eyes for 3D display. Due to the 3D display, the operator 5181 can more accurately recognize the depth of living tissue in the operation site. Note that, in a case where the image capture unit 5123 has a multi-plate type configuration, a plurality of lens units 5121 is provided in correspondence with the imaging elements.

Furthermore, the image capture unit 5123 is not necessarily provided in the camera head 5119. For example, the image capture unit 5123 may be provided just behind the objective lens in the lens barrel 5117.

The driving unit 5125 includes an actuator and moves the zoom lens and the focus lens of the lens unit 5121 by a predetermined distance along the optical axis under the control by the camera head control unit 5129. With this movement, the magnification and the focus of the image captured by the image capture unit 5123 may be appropriately adjusted.

The communication unit 5127 includes a communication device for transmitting and receiving various kinds of information to and from the CCU 5153. The communication unit 5127 transmits the image signal obtained from the image capture unit 5123 to the CCU 5153 via the transmission cable 5179 as raw data. At this time, to display the captured image of the operation site with low latency, it is preferable that the image signal be transmitted by optical communication. This is because, since the operator 5181 performs surgery while observing the state of the affected part by using the captured image during surgery, it is required to display a moving image of the operation site in real time as much as possible for safer and more reliable surgery. In a case where the optical communication is performed, a photoelectric conversion module which converts an electric signal into an optical signal is provided in the communication unit 5127. The image signal is transmitted to the CCU 5153 via the transmission cable 5179 after being converted into an optical signal by the photoelectric conversion module.

Furthermore, the communication unit 5127 receives a control signal for controlling the driving of the camera head 5119 from the CCU 5153. The control signal includes, for example, information regarding the imaging conditions such as information specifying the frame rate of the captured image, information specifying the exposure value during image capture, and/or information specifying the magnification and the focus of the captured image. The communication unit 5127 provides the received control signal to the camera head control unit 5129. Note that the control signal from the CCU 5153 may be transmitted by optical communication. In this case, a photoelectric conversion module which converts an optical signal into an electric signal is provided in the communication unit 5127, and the control signal is provided to the camera head control unit 5129 after being converted into an electric signal by the photoelectric conversion module.

Note that the control unit 5177 of the CCU 5153 automatically sets the abovementioned imaging conditions such as the frame rate, the exposure value, the magnification, and the focus on the basis of the obtained image signal. That is, the endoscope 5115 has a so-called auto exposure (AE) function, an auto focus (AF) function, and an auto white balance (AWB) function.

The camera head control unit 5129 controls the driving of the camera head 5119 on the basis of the control signal from the CCU 5153 received via the communication unit 5127. For example, the camera head control unit 5129 controls the driving of the imaging element of the image capture unit 5123 on the basis of the information specifying the frame rate of the captured image and/or the information specifying the exposure during image capture. Furthermore, for example, the camera head control unit 5129 appropriately moves the zoom lens and the focus lens of the lens unit 5121 via the driving unit 5125 on the basis of the information specifying the magnification and the focus of the captured image. The camera head control unit 5129 may further have a function for storing information for identifying the lens barrel 5117 and the camera head 5119.

Note that resistance to autoclave sterilization can be provided to the camera head 5119 by arranging the components such as the lens unit 5121 and the image capture unit 5123 in a sealed structure having high airtightness and waterproofness.

Next, the functional configuration of the CCU 5153 will be described. The communication unit 5173 includes a communication device for transmitting and receiving various kinds of information to and from the camera head 5119. The communication unit 5173 receives the image signal transmitted from the camera head 5119 via the transmission cable 5179. At this time, as described above, the image signal may be preferably transmitted by optical communication. In this case, a photoelectric conversion module which converts an optical signal into an electric signal is provided in the communication unit 5173 so as to enable optical communication. The communication unit 5173 provides the image signal converted into an electric signal to the image processing unit 5175.

Further, the communication unit 5173 transmits the control signal for controlling the driving of the camera head 5119 to the camera head 5119. The control signal may also be transmitted by optical communication.

The image processing unit 5175 performs various kinds of image processing on the image signal that is the raw data transmitted from the camera head 5119. The image processing includes various known signal processing such as a development process, an image quality enhancement process (band emphasis process, super-resolution process, noise reduction (NR) process, camera shake correction process, and/or the like), and/or an enlargement process (electronic zoom process), for example. Further, the image processing unit 5175 executes detection processing on the image signal so as to achieve the AE, the AF, and the AWB.

The image processing unit 5175 includes a processor such as a CPU and a GPU, and the processor operates according to a predetermined program so that the image processing and the detection processing described above may be executed. Note that, in a case where the image processing unit 5175 includes a plurality of GPUs, the image processing unit 5175 appropriately divides information regarding the image signal and executes the image processing in parallel by using the plurality of GPUs.

The control unit 5177 performs various controls regarding image capture of the operation site by the endoscope 5115 and display of the captured image. For example, the control unit 5177 generates the control signal to control the driving of the camera head 5119. At this time, in a case where the imaging conditions are input by the user, the control unit 5177 generates the control signal on the basis of the input performed by the user. Alternatively, in a case where the endoscope 5115 has the AE function, the AF function, and the AWB function, the control unit 5177 appropriately calculates an optimum exposure value, focal distance, and white balance according to the result of the detection processing by the image processing unit 5175 and generates a control signal.

Further, the control unit 5177 displays, in the display device 5155, the image of the operation site on the basis of the image signal to which the image processing has been executed by the image processing unit 5175. In this case, the control unit 5177 recognizes various objects in the image of the operation site by using various image recognition technologies. For example, the control unit 5177 detects an edge shape, a color, and the like of the object included in the image of the operation site, thereby being capable of recognizing surgical tools such as a forceps, a specific body portion, bleed, mist when the energy treatment instrument 5135 is used, and the like. When displaying the image of the operation site in the display device 5155, the control unit 5177 overlays various kinds of surgery assist information on the image of the operation site using the recognition result. The surgery assist information is displayed as overlaid, and is presented to the operator 5181, so that the operator 5181 can more safely and reliably proceed with the surgery.

The transmission cable 5179 for connecting the camera head 5119 and the CCU 5153 is an electric signal cable compatible with electric signal communication, an optical fiber compatible with optical communication, or a composite cable thereof.

Here, in the illustrated example, wired communication has been performed by using the transmission cable 5179. However, the camera head 5119 and the CCU 5153 may wirelessly communicate with each other. In a case where the camera head 5119 and the CCU 5153 wirelessly communicate with each other, it is not necessary to provide the transmission cable 5179 in the operating room. Therefore, a situation where movement of a medical staff in the operating room is prevented by the transmission cable 5179 may be resolved.

An example of the operating room system 5100 to which the technology according to the present disclosure may be applied has been described above. Note that, here, a case has been described where a medical system to which the operating room system 5100 is applied is the endoscopic surgical system 5113 as an example. However, the configuration of the operating room system 5100 is not limited to this example. For example, the operating room system 5100 may be applied to a flexible endoscope system for examination and a microscope surgical system instead of the endoscopic surgical system 5113.

The technology according to the present disclosure is applicable to the imaging element of the image capture unit 5123 in the camera head 5119. More specifically, the image capture unit 5123 may include a tunable filter and a special purpose filter in the stage preceding the imaging element. With this configuration, the image capture unit 5123 can acquire both image data in which wavelength extraction is possible in a tunable manner and image data used for a special purpose. For example, in a case where a specific affected part or site is determined in advance as an acquisition target, each component such as the image processing unit 5175 can perform a predetermined process using image data used for a special purpose. In addition, in a case where a specific affected part or site is not determined in advance as an acquisition target or in a case where captured images of subjects cannot be distinguished (for example, in a case where blood vessels or nerves cannot be distinguished, etc.), each component such as the image processing unit 5175 can perform a predetermined process using the image data in which wavelength extraction is possible in a tunable manner.

While preferred embodiments of the present disclosure have been described above in detail with reference to the drawings, the technical scope of the present disclosure is not limited thereto. It is obvious that a person having ordinary knowledge in the technical field of the present disclosure could arrive at various changes or modifications within the scope of the technical idea set forth in the claims, and it is understood that such changes or modifications naturally belong to the technical scope of the present disclosure.

Note that the numerical values used in the above description are merely examples, and may be changed as appropriate. For example, the wavelengths of light that can pass through the special purpose filter are about 531 [nm], about 570 [nm], about 761 [nm], about 758 [nm], etc. in the above description. However, these wavelengths can be flexibly changed according to a target to be analyzed, design, or the like. Further, these wavelengths are, for example, center wavelengths in the respective wavelength bands (but are not limited thereto). Here, the center wavelength in the wavelength band is, for example, the center of the half bandwidth (but not limited thereto). Further, the half bandwidth used in the above description is a width between wavelengths having a filter transmittance of about 50[%] (but not limited thereto).

Further, the effects described in the present specification are merely explanatory or exemplary, and are not restrictive. That is, the technology according to the present disclosure may provide other effects that are apparent to those skilled in the art from the description of the present specification, in addition to or instead of the abovementioned effects.

Note that the following configurations also belong to the technical scope of the present disclosure.

(1)
A signal processing device including:
an acquisition unit that acquires a signal of a first wavelength band in which wavelength extraction is possible in a tunable manner by means of postprocessing and a signal of a second wavelength band to be used for a special purpose; and
a signal processing unit that performs signal processing using the signal of the first wavelength band and the signal of the second wavelength band.

(2)
The signal processing device according to (1),
in which the signal processing unit extracts a signal of a desired wavelength band using the signal of the first wavelength band.

(3)
The signal processing device according to (2),
in which the signal processing unit calculates a vegetation index using at least one of the signal of the desired wavelength band or the signal of the second wavelength band.

(4)
The signal processing device according to (3),
in which the signal processing unit calculates at least any one of a normalized difference vegetation index (NDVI), a green normalized difference vegetation index (GNDVI), a photochemical reflectance index (PRI), or a sun-induced fluorescence (SIF), as the vegetation index.

(5)
A signal processing method executed by a computer, the method including:
acquiring a signal of a first wavelength band in which wavelength extraction is possible in a tunable manner by means of postprocessing and a signal of a second wavelength band to be used for a special purpose; and
performing signal processing using the signal of the first wavelength band and the signal of the second wavelength band.

(6)
An image capture device including:
a first detection unit that detects a signal of a first wavelength band in which wavelength extraction is possible in a tunable manner by means of postprocessing; and
a second detection unit that detects a signal of a second wavelength band to be used for a special purpose.

(7)
The image capture device according to (6),
in which the first detection unit and the second detection unit constitute pixels of an image sensor.

(8)
The image capture device according to (7),
in which the first detection unit and the second detection unit include, on a pixel basis, filters having different spectral characteristics.

(9)
The image capture device according to (8),
in which transmittances of the filters provided in the first detection unit and the second detection unit are determined on the basis of output sensitivities of the first detection unit and the second detection unit, respectively.

(10)
The image capture device according to (8),
in which the number of pixels in the first detection unit and the number of pixels in the second detection unit are determined on the basis of output sensitivities of the first detection unit and the second detection unit, respectively.

(11)
The image capture device according to (8), further including
an exposure control unit that controls exposure on the basis of output sensitivity of each of the first detection unit and the second detection unit.

(12)
The image capture device according to any one of (8) to (11),
in which the filter provided in the first detection unit is a plasmon resonance filter.

(13)
The image capture device according to any one of (8) to (12),
in which the filter included in the second detection unit includes an RGB sensor and a dual bandpass filter.

(14)
The image capture device according to any one of (6) to (13),
in which the first detection unit and the second detection unit are provided in different cameras or image capture mechanisms.

(15)
The image capture device according to (14), further including
a dichroic filter that separates light entering the first detection unit and the second detection unit.

(16)
The image capture device according to any one of (6) to (15),
in which the first wavelength band is a wide band.

(17)
The image capture device according to any one of (6) to (16),
in which the second wavelength band is a wide band or a narrow band.

(18)
The image capture device according to any one of (6) to (17), further including
a display control unit that displays an image generated on the basis of the signal of the first wavelength band so as to be overlaid on an image generated on the basis of the signal of the second wavelength band.

(19)
A medical image capture device including:
a first detection unit that detects a signal of a first wavelength band in which wavelength extraction is possible in a tunable manner by means of postprocessing; and
a second detection unit that detects a signal of a second wavelength band to be used for a special purpose.

(20)

The medical image capture device according to (19), further including a focusing unit that performs focusing using the signal of the second wavelength band.

REFERENCE SIGNS LIST

100 Image capture device
110 Imaging optical system
120 Exposure processing unit
130 Exposure control unit
140 Filter
150 Image sensor
160 Output unit
170 Signal processing unit
180 Storage unit
190 Communication unit
200 Information processing device
300 Microscope
310 Data processing unit

The invention claimed is:

1. A signal processing device comprising:
    an acquisition unit that acquires a signal of a first wavelength band in which wavelength extraction is possible in a tunable manner by means of postprocessing and a signal of a second wavelength band to be used for a special purpose; and
    a signal processing unit that performs signal processing using the signal of the first wavelength band or a combination of the signal of the first wavelength band and the signal of the second wavelength band,
    wherein the signal processing unit extracts a signal of a desired wavelength band using the signal of the first wavelength band,
    wherein the signal processing unit calculates a vegetation index using at least one of the signal of the desired wavelength band or the signal of the second wavelength band, and
    wherein the signal processing unit calculates at least any three of a normalized difference vegetation index (NDVI), a green normalized difference vegetation index (GNDVI), a photochemical reflectance index (PRI), or a sun-induced fluorescence (SIF), as the vegetation index.

2. A signal processing method executed by a computer, the method comprising:
    acquiring a signal of a first wavelength band in which wavelength extraction is possible in a tunable manner by means of postprocessing and a signal of a second wavelength band to be used for a special purpose; and
    performing signal processing using the signal of the first wavelength band or a combination of the signal of the first wavelength band and the signal of the second wavelength band by
    extracting a signal of a desired wavelength band using the signal of the first wavelength band, and
    calculating a vegetation index using at least one of the signal of the desired wavelength band or the signal of the second wavelength band, and
    wherein the vegetation index is at least any three of a normalized difference vegetation index (NDVI), a green normalized difference vegetation index (GNDVI), a photochemical reflectance index (PRI), or a sun-induced fluorescence (SIF).

* * * * *